United States Patent
Reisch

(10) Patent No.: US 9,315,514 B2
(45) Date of Patent: Apr. 19, 2016

(54) 1,3-DIOXANOMORPHIDES AND 1,3-DIOXANOCODIDES

(71) Applicant: Rhodes Technologies, Coventry, RI (US)

(72) Inventor: Helge A. Reisch, Westerly, RI (US)

(73) Assignee: Rhodes Technologies, Coventry, RI (US)

( * ) Notice: Subject to any disclaimer, the term of this patent is extended or adjusted under 35 U.S.C. 154(b) by 0 days.

(21) Appl. No.: 13/975,747

(22) Filed: Aug. 26, 2013

(65) Prior Publication Data

US 2014/0057932 A1 Feb. 27, 2014

Related U.S. Application Data

(60) Provisional application No. 61/693,593, filed on Aug. 27, 2012.

(51) Int. Cl.
| | | |
|---|---|---|
| A61K 31/44 | (2006.01) |
| C07D 221/22 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 489/12 | (2006.01) |
| C07D 491/18 | (2006.01) |

(52) U.S. Cl.
CPC ............ C07D 491/18 (2013.01); C07D 489/12 (2013.01)

(58) Field of Classification Search
None
See application file for complete search history.

(56) References Cited

U.S. PATENT DOCUMENTS

| | | | |
|---|---|---|---|
| 3,433,791 A | 3/1969 | Bentley | |
| 3,536,809 A | 10/1970 | Applezweig | |
| 3,560,506 A | 2/1971 | Brown et al. | |
| 3,562,279 A | 2/1971 | Brown et al. | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 3,931,187 A | 1/1976 | Langbein et al. | |
| 4,008,719 A | 2/1977 | Theeuwes et al. | |
| 4,440,931 A * | 4/1984 | Kotick et al. | 546/44 |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 5,952,495 A | 9/1999 | Huang et al. | |

| | | | |
|---|---|---|---|
| 6,723,894 B2 | 4/2004 | Fist et al. | |
| 2008/0312411 A1 | 12/2008 | Wolf et al. | |
| 2010/0081820 A1 | 4/2010 | Jarvi et al. | |

FOREIGN PATENT DOCUMENTS

| | | |
|---|---|---|
| CS | 277222 B6 | 12/1992 |
| CZ | 279 821 B6 | 7/1995 |
| CZ | 300 995 B6 | 10/2009 |
| DE | 1938 219 | 2/1970 |
| GB | 937214 | 9/1963 |
| GB | 969263 | 9/1964 |
| GB | 1260 699 | 1/1972 |
| SK | 278 715 B6 | 1/1998 |
| WO | WO 98/02033 A1 | 1/1998 |
| WO | WO 2004/039317 A2 * | 5/2004 |
| WO | WO 2006/035195 A1 | 4/2006 |
| WO | WO 2007/081506 A1 | 7/2007 |
| WO | WO 2008/048957 A1 | 4/2008 |

(Continued)

OTHER PUBLICATIONS

Kotick, MP. et al. Analgesic Narcotic Antagonists. 15. Potent Narcotic Agonist 7β-(Arylalkyl)-4,5α-epoxymorphinans. J. Med. Chem. 1983, vol. 26, p. 1051.*

(Continued)

*Primary Examiner* — Rita Desai
*Assistant Examiner* — Ben S Michelson
(74) *Attorney, Agent, or Firm* — Sterne, Kessler, Goldstein & Fox P.L.L.C.

(57) ABSTRACT

The application is directed to compounds of Formula I

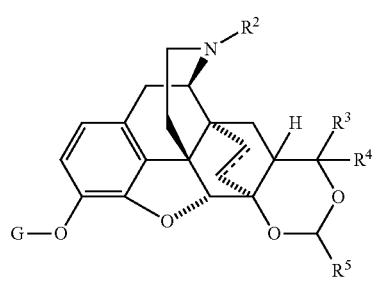

and pharmaceutically acceptable salts, prodrugs, and solvates thereof, wherein G, $R^2$-$R^5$, and ⫽ are defined as set forth in the specification. The invention is also directed to use of compounds of Formula I as synthetic intermediates or to treat disorders responsive to the modulation of one or more opioid receptors. Certain compounds of the present invention are especially useful for treating pain.

41 Claims, No Drawings

(56) References Cited

FOREIGN PATENT DOCUMENTS

| WO | WO 2012/038813 A1 * | 3/2012 |
|---|---|---|
| WO | WO 2014/033530 A1 | 3/2014 |

OTHER PUBLICATIONS

Greenwald, RB. et al. Drug Delivery Systems: Water Soluble Taxol 2'-Poly(ethylene glycol) Ester Prodrugs-Design and in Vivo Effectiveness. J. Med. Chem. 1996, vol. 39, p. 425.*

Testa, B. et al. Lessons Learned from Marketed and Investigational Prodrugs. J. Med. Chem. 2004, vol. 47(10), p. 2393.*

Kocienski, PJ. Protecting Groups. THIEME. 2005, p. 188.*

Freshney, RI. Culture of Animal Cells: A Manual of Basic Technique. John Wiley and Sons. 2005, 5th Ed., p. 8.*

Nakamura, I. et al. Transition-Metal-Catalyzed Reactions in Heterocyclic Synthesis. Chem. Rev. 2004, vol. 104, p. 2127.*

Chattopadhyay, SK. et al. Formation of medium-ring heterocycles by diene and enyne metathesis. Tetrahedron. 2007, vol. 63, p. 3919.*

Banfi L et al. Ugi Multicomponent Reaction Followed by an Intermolecular Nucleophilic Substitution: Convergent Multicomponent Synthesis of 1-sulfonyl 1,4-diazepan-5-ones and of their benzo-fuzed Derivatives. J. Org. Chem. 2007, vol. 72, p. 2151.*

Dorwald, FZ. Side Reactions in Organic Synthesis. Wiley. 2005, preface.*

Bal, B.S. and Pinnick, H.W., "Convenient Conversion of Alcohols into Formaldehyde Acetals or Ethers," *J. Org. Chem. 44*(21):3727-3728, American Chemical Society, United States (1979).

Barthó, L., et al., "Involvement of capsaicin-sensitive neurones in hyperalgesia and enhanced opioid antinociception in inflammation," *Naunyn-Schmiedeberg's Arch. Pharmacol. 342*:666-670, Springer Verlag, Germany (1990).

Barton, J.W., et al., "Diels-Alder Reactions of Thebaines with Cycloalkenones; Lithium Tetrafluoroborate as a Novel Diels-Alder Catalyst.," *Tetrahedron Letters 34*(42):6777-6778, Pergamon Press Ltd, Great Britain (1993).

Bentley, K.W. and Hardy, D.G., "Novel Analgesics and Molecular Rearrangements in the Morphine-Thebaine Group. I. Ketones Derived from 6,14-endo-Ethenotetrahydrothehaine," *J. Am. Chem. Soc. 89*(13):3267-3273, American Chemical Society, United States (1967).

Bentley, K.W., et al., "Novel Analgesics and Molecular Rearrangements in the Morphine-Thebaine Group. II. Alcohols Derived from 6,14-endo-Etheno- and 6,14-endo-Ethanotetrahydrothebaine," *J. Am. Chem. Soc. 89*(13):3273-3280, American Chemical Society, United States (1967).

Bentley, K.W. and Hardy, D.G., "Novel Analgesics and Molecular Rearrangements in the Morphine-Thebaine Group. III. Alcohols of the 6,14-endo-Ethenotetrahydrooripavine Series and Derived Analogs of N-Allylnormorphine and -norcodeine," *J. Am. Chem. Soc. 89*(13):3281-3292, American Chemical Society, United States (1967).

Bentley, K.W., et al., "Novel Analgesics and Molecular Rearrangements in the Morphine-Thebaine Group. V. Derivatives of 7,8-Dihydrocyclohexeno[1',2':8,14]codeinone," *J. Am. Chem. Soc. 89*(13):3303-3311, American Chemical Society, United States (1967).

Bingham, A.L., et al., "Over one hundred solvates of sulfathiazole," *Chem. Commun.*:603-604, The Royal Society of Chemistry, Great Britain (2001).

Breeden, S.W., et al. "6-O-Demethylation of the Thevinols with Lithium Aluminum Hydride: Selective Demethylation of a Tertiary Alkyl Methyl Ether in the Presence of an Aryl Methyl Ether," *Helvetica Chimica Acta 82*:1978-1980, Schweizerische Chemische Gesellschaft, Switzerland (1999).

Buchwald, H., et al., "Long-term, continuous intravenous heparin administration by an implantable infusion pump in ambulatory patients with recurrent venous thrombosis," *Surgery 88*(4):507-516, The C.V. Mosby Co., United States (1980).

Bundgaard, H., "(C) Means to Enhance Penetration, (1) Prodrugs as a means to improve the delivery of peptide drugs," *Advanced Drug Delivery Reviews 8*:1-38, Elsevier Science Publishers B.V., Netherlands (1992).

Caira, M.R., et al., "Preparation and Crystal Characterization of a Polymorph, a Monohydrate, and an Ethyl Acetate Solvate of the Antifungal Fluconazole," *Journal of Pharmaceutical Sciences 93*(3):601-611, Wiley-Liss, Inc. and the American Pharmacists Association, United States (2004).

Čejka, J., et al., "(5R,6R,7R,9R,13R,14S)-21-Cyclopropylmethyl-6,14-endo-ethano-2',3',4',5',7,8-hexahydro-4',4',5',5'-tetramethylfurano[2',3'6,7]normorphide hydrochloride methanol solvate," *Acta Cryst.E61*:o2274-o2276, International Union of Crystallography, Great Britain (2005).

Cone, E.J., et al., "Stability of the 6,14-endo-Ethanotetrahydrooripavine Analgesics: Acid-Catalyzed Rearrangement of Buprenorphine," *Journal of Pharmaceutical Sciences 73*(2):243-246, American Pharmaceutical Association, United States (1984).

Coop, A., et al., "Methylation of the Enolates of Thevinone and some Analogues," *Tetrahedron 51*(35):9681-9698, Elsevier Science Ltd., Great Britain (1995).

Coop, A., et al., "Ring Constrained Analogues of the Thevinones; Diels-Alder Reactions of Thebaines with 1-Indenone and Methylene Cycloalkanones," *Tetrahedron Letters 36*(10):1689-1692, Elsevier Science Ltd., Great Britain (1995).

Coop, A., et al., "Direct and Simple O-Demethylation of Thebaine to Oripavine," *J. Org. Chem. 61*:6774, American Chemical Society, United States (1996).

Coop, A. et al., "L-Selectride as a General Reagent for the O-Demethylation and N-Decarbomethoxylation of Opium Alkaloids and Derivatives," *J. Org. Chem. 63*:4392-4396, American Chemical Society, United States (1998).

Coop, A., et al., "Structural Determinants of Opioid Activity in the Orvinols and Related Structures: Ethers of Orvinol and Isoorvinol," *J. Med. Chem. 43*:1852-1857, American Chemical Society, United States (2000).

D'Amour, F.E. and Smith, D.L., "A Method for Determining Loss of Pain Sensation," *The Journal of Pharmacology and Experimental Therapeutics 72*:74-79, The American Society for Pharmacology and Experimental Therapeutics Incorporated, United States (1941).

During, M.J., et al., "Controlled Release of Dopamine from a Polymeric Brain Implant: In Vivo Characterization," *Annals of Neurology 25*(4): 351-356, American Neurological Association, United States (1989).

Fujii, H., et al., "Rational drug design and synthesis of a selective ε opioid receptor antagonist on the basis of the accessory site concept," *Bioorganic & Medicinal Chemistry Letters 14*:4241-4243, Elsevier Ltd., Great Britain (2004).

Garrett, E.R. and Chandran, V.R., "Pharmacokinetics of Morphine and Its Surrogates VI: Bioanalysis, Solvolysis Kinetics, Solubility, $pK'_a$ Values, and Protein Binding of Buprenorphine," *Journal of Pharmaceutical Sciences 74*(5):515-523, American Pharmaceutical Association, United States (1985).

Grivas, K., et al., "Acid Catalysed Rearrangements of the Thevinols: The Mechanism of Furanocodide Formation.," *Tetrahedron Letters 40*:1795-1798, Elsevier Science Ltd., Great Britain (1999).

Gu, Z-M., et al., "Determining Absolute Configurations of Stereocenters in Annonaceous Acetogenins through Formaldehyde Acetal Derivatives and Mosher Ester Methodology," *J. Org. Chem. 59*:5162-5172, American Chemical Society, United States (1994).

Hanessian, S., et al., "Chemistry of α-Alkoxy Sulfoxides. Formation of Methylene Acetals from Dimethyl Sulfoxide and Alcohols," *J. Am. Chem. Soc. 94*(25):8929-8931, American Chemical Society, United States (1972).

Hargreaves, K., et al., "A new and sensitive method for measuring thermal nociception in cutaneous hyperalgesia," *Pain 32*(1):77-88, Elsevier, Netherlands (1988).

Howard III, M.A., et al., "Intracerebral drug delivery in rats with lesion-induced memory deficits," *J. Neurosurg. 71*(1): 105-112, American Association of Neurological Surgeons, United States (1989).

(56) References Cited

OTHER PUBLICATIONS

Husbands, S.M. et al., "Ring Constrained Analogues of the Orvinols: The Furanomorphides," *Bioorganic & Medicinal Chemistry Letters* 9:831-834, Elsevier Science Ltd., Great Britain (1999).

Hutchins, C.W., "6-Demethoxythebaine and its Conversion to Analgesics of the 6, 14-Ethenomorphinan Type," *J. Med. Chem.* 24(7):773-777, American Chemical Society, United States (1981).

Hutchins, C.W. and Rapoport, H., "Analgesics of the Orvinol Type. 19-Deoxy and 6,20-Epoxy Derivatives," *J. Med. Chem.* 27:521-527, American Chemical Society, United States (1984).

János, M., et al., "6,14-Etenomorfinánok danzil-származékainak szintézise és analitikai jellemzése," *Acta Pharmaceutica Hungarica* 69:218-223, Magyar Gyogyszereszeti Tarsasag, Hungary (1999).

Kakeya, N., et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid," *Chem. Pharm. Bull.* 32(2):692-698, Pharmaceutical Society of Japan, Japan (1984).

Kim, S.H. and Chung, J.M., "An experimental model for peripheral neuropathy produced by segmental spinal nerve ligation in the rat," *Pain* 50:355-363, Elsevier Science Publishers B.V., Netherlands (1992).

Kopcho, J.J. and Schaeffer, J.C., "Selective O-Demethylation of 7α-(Aminomethyl)-6,14-endo-ethenotetrahydrothebaine," *J. Org. Chem.* 51:1620-1622, American Chemical Society, United States (1986).

Kotick, M.P., et al., "Analgesic Narcotic Antagonists. 15. Potent Narcotic Agonist 7β-(Arylalkyl)-4,5α-epoxymorphinans," *J. Med. Chem.* 26:1050-1056, American Chemical Society, United States (1983).

Langer, R. and Peppas, N., "Chemical and Physical Structure of Polymers as Carriers for Controlled Release of Bioactive Agents: A Review," *JMS-Rev. Macromol. Chem. Phys.* C23(1):61-126, Marcel Dekker, Inc., United States (1983).

Langer, R., "New Methods of Drug Delivery," *Science* 249(4976):1527-1533, American Association for the Advancement of Science, United States (1990).

Laus, G., et al., "Etorphine-Related Ferrocenyl-Substituted Morphinan Alkaloids," *Helvetica Chimica Acta* 86:3274-3280, Schweizerische Chemische Gesellschaft, Switzerland (2003).

Leland, D.L. and Kotick, M.P., "7α- or 7β-(4-Phenylbutyl)dihydrocodeine Derivatives," *J. Org. Chem.* 48:1813-1819, American Chemical Society, United States (1983).

Lever, J.R., et al., "Facile Synthesis of [$^{11}$C]Buprenorphine for Positron Emission Tomographic Studies of Opioid Receptors," *Appl. Radiat. Isot.* 41(8):745-752, Pergamon Press plc, Great Britain (1990).

Levy, R.J., et al., "Inhibition of Calcification of Bioprosthetic Heart Valves by Local Controlled-Release Diphosphate," *Science* 228(4696):190-192, American Association for the Advancement of Science, United States (1985).

Loew, G.H. and Berkowitz, D.S., "Intramolecular Hydrogen Bonding and Conformational Studies of Bridged Thebaine and Oripavine Opiate Narcotice Agonists and Antagonists," *J. Med. Chem.* 22(6):603-607, American Chemical Society, United States (1979).

Lopez-Berestein, G., "Treatment of Systemic Fungal Infections with Liposomal-Amphotericin B," *Liposomes in the Therapy of Infectious Diseases and Cancer*:317-327, Alan R. Liss, Inc., United States (1989).

Luthra, S.K., et al., "Automated Radiosyntheses of [6-O-Methyl-$^{11}$C]Diprenorphine and [6-O-Methyl-$^{11}$C]Buprenorphine From 3-O-Trityl Protected Precursors," *Appl. Rad. Isot.* 45(8):857-873, Elsevier Science Ltd., Great Britain (1994).

Machara, A. et al., "Improved Synthesis of Buprenorphine from Thebaine and/or Oripavine via Palladium-Catalyzed N-Demethylation/Acylation and/or Concomitant O-Demethylation," *Adv. Synth. Catal.* 354:613-626, Wiley-VCH Verlag GmbH & Co. KGaA, Germany (Feb. 2012).

Marton, J., et al., "Herstellung von 6, 14-Ethenomorphinan-Derivaten," *Monatshefte fur Chemie* 125:1229-1239, Springer-Verlag, Austria (1994).

Marton, J., et al., "Synthesis of N-Substituted 7β-Diprenorphine Derrivatives," *Synthetic Communications: An International Journal for Rapid Communication of Synthetic Organic Chemistry* 25(6):829-848, Marcel Dekker, Inc., United States (1995).

Nielsen, N.M., and Bundgaard, H., "Glycolamide Esters as Biolabile Prodrugs of Carboxylic Acid Agents: Synthesis, Stability, Bioconversion, and Physicochemical Properties," *Journal of Pharmaceutical Sciences* 77(4):285-298, American Pharmaceutical Association, United States (1988).

Queiroz, E.F., et al., "An Improved Method for the Formation of Formaldehyde Acetal Derivatives from Annonaceous Acetogenins," *Tetrahedron Letters* 40:697-700, Elsevier Science Ltd., Great Britain (1999).

Saudek, C.D., et al., "A Preliminary Trial of the Programmable Implantable Medication System for Insulin Delivery," *The New England Journal of Medicine* 321(9): 574-579, Massachusetts Medical Society, United States (1989).

Schütz, J., et al., "Synthesis and Pharmacological Evaluation of 18, 19-Dehydrobuprenorphine," *Heterocycles* 54(2):989-998, The Japan Institute of Heterocyclic Chemistry, Japan (2001).

Sefton, M.V., "Implantable Pumps," *Critical Reviews™ in Biomedical Engineering* 14(3):201-240, CRC Press, Inc., United States (1987).

Seltzer, Z., et al., "A novel behavioral model of meuropathic pain disorder produced in rats by partial sciatic nerve injury," *Pain* 43:205-218, Elsevier Science Publishers B.V. Netherlands (1990).

Stein, C., et al., "Unilateral Inflammation of the Hindpaw in Rats as a Model of Prolonged Noxious Stimulation: Alterations in Behavior and Nociceptive Thresholds," *Pharmacology Biochemistry & Behavior* 31:455-451, Pergamon Press plc, United States (1988).

Torbati, D., et al., "Effect of hyopthermia on ventilation in anesthetized, spontaneously breathing rats: theoretical implications for mechanical ventilation," *Intensive Care Med.* 26:585-591, Springer-Verlag, Germany (2000).

Treat, J., et al., "Liposome Encapsulated Doxorubicin Preliminary Results of Phase I and Phase II Trials," in *Liposomes in the Therapy of Infectious Diseases and Cancer*, 353-365, Alan R. Liss, Inc., United States (1989).

Uff, B.C., et al., "NMR Spectra and Sterochemistry of some 7-Substituted 6,14-Bridged Thebaine Derivatives," *Magnetic Resonance in Chemistry* 23 (6):454-459, Wiley Heyden Ltd., Great Britain (1985).

Van Tonder, E.C., et al., "Preparation and Physicochemical Characterization of 5 Niclosamide Solvates and 1 Hemisolvate," *AAPS PharmSciTech* 5(1):1-10, Article 12, Springer Science + Business Media LLC, United States (2004).

Woolfe, G. and MacDonald, A.D., "The Evaluation of the Analgesic Action of Pethidine Hydrochloride (Demerol)," *The Journal of Pharmacology and Experimental Therapeutics* 80-81300-307, The American Society for Pharmacological and Experimental Therapeutics Incorporated, United States (1944).

International Search Report for International Patent Application No. PCT/IB2013/001877, mailed on May 12, 2013, Eurpean Patent Office, Rijswijk, Netherlands.

English language Abstract of CS 277222 B6, Chemical Abstracts Service, STN International, Access No. 120:323980, entered STN on Jun. 25, 1994 (Accessed online on Sep. 11, 2014).

English language Abstract of CZ 279 821 B6, Espacenet, European Patent Office, accessed on Sep. 11, 2014.

English language Abstract of SK 278 715 B6, Espacenet, European Patent Office, accessed on Sep. 11, 2014.

English language Abstract of CZ 300 995 B6, Espacenet, European Patent Office, accessed on Sep. 10, 2014.

\* cited by examiner

1,3-DIOXANOMORPHIDES AND 1,3-DIOXANOCODIDES

BACKGROUND OF THE INVENTION

1. Field of the Invention

This application is in the field of medicinal chemistry. The application relates to novel 1,3-dioxanomorphides and 1,3-dioxanocodides, and pharmaceutical compositions comprising any of these compounds. The application also relates to methods of making 1,3-dioxanomorphides and 1,3-dioxanocodides, and their use.

2. Description of the Related Art

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone, oxymorphone, or buprenorphine).

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Buprenorphine, (2S)-2-[17-cyclopropylmethyl-4,5$\alpha$-epoxy-3-hydroxy-6-methoxy-6$\alpha$,14$\alpha$-ethanomorphinan-7$\alpha$-yl]-3,3-dimethylbutan-2-ol, a semi-synthetic opioid having the structure:

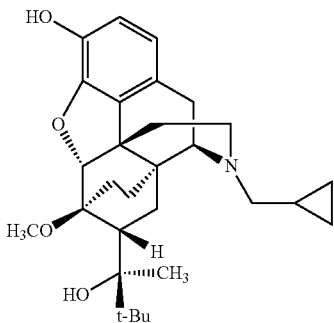 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

is used to treat opioid addiction, to control moderate acute pain in non-opioid tolerant individuals, and to control moderate chronic pain. Buprenorphine is classified both as an orvinol and as a thevinol, which means that it can be derived from either oripavine or thebaine. K. W. Bentley discovered buprenorphine using thebaine as the initial backbone structure. Thebaine is one of the main alkaloids in the Iranian poppy (*Papaver bracteatum*). Thebaine can also be isolated from *Papaver somniferum* which is also a source for oripavine (U.S. Pat. No. 6,723,894).

Buprenorphine has an extremely high binding affinity at the $\mu$- and $\kappa$-opioid receptors. It has partial agonist activity at the $\mu$-opioid receptor, partial or full agonist activity at the ORL-1/nociceptin and $\delta$-opioid receptors, and competitive antagonist activity at the $\kappa$-opioid receptor. Buprenorphine exhibits an analgesic effect approximately 25 to 40 times more potent than morphine (by weight of equivalent low doses). Buprenorphine is marketed as oral formulations (tablets, sublingual tablets, and sublingual films), parenteral preparations, and transdermal patches.

Buprenorphine differs from the majority of morphinane alkaloids by the presence of an additional 6,14-ethano bridge and a carbinol (tertiary alcohol) in the side-chain. This tertiary alcohol gives rise to an acid catalyzed decomposition of buprenorphine, which, depending on the conditions, either results in dehydration and formation of EP Impurity F (compound 2 in Garrett, E. R., et al., *Journal of Pharmaceutical Sciences* 74:515-523 (1985)) or in rearrangement with the loss of methanol and formation of a furanomorphide (demethoxy-buprenorphine, EP Impurity I) (compound I in Cone, E. J. et al., *Journal of Pharmaceutical Sciences* 73:243-246 (1984) and compound 3 in Garrett, E. R., et al., supra). EP Impurity I has been further studied with other ring constrained furanomorphides (Husbands, S. M., et al., *Bioorganic & Medical Chemistry Letters* 9:831-834 (1999); Čejka, J., et al., *Acta Cryst.* E61:2274-2276 (2005)).

There is a need for buprenorphine derivatives that have a decreased sensibility towards acids while maintaining the pharmacological activity.

BRIEF SUMMARY OF THE INVENTION

In one aspect, the present disclosure provides compounds represented by Formulae I-XVIII, below, and the pharmaceutically acceptable salts, prodrugs and solvates thereof, collectively referred to herein as "Compounds of the Invention" (each is individually referred to hereinafter as a "Compound of the Invention").

In another aspect, the present invention provides the use of Compounds of the Invention as synthesis intermediates.

In another aspect, the present disclosure provides the use of Compounds of the Invention as modulators of one or more opioid receptors. Specifically, the present disclosure provides the use of Compounds of the Invention as modulators of $\mu$, $\delta$, and/or $\kappa$ opioid receptors, and especially modulators of $\mu$ and/or $\kappa$ opioid receptors.

In another aspect, the present disclosure provides a method for treating a disorder responsive to the modulation of one or more opioid receptors in a patient, comprising administering to the patient an effective amount of a Compound of the Invention.

In another aspect, the present disclosure provides a use of a Compound of the Invention as an analgesic to treat pain; or as an agent to treat withdrawal from alcohol or drug addiction; or as an agent to treat constipation; or an agent to treat diarrhea (each of pain, alcohol withdrawal, drug withdrawal, constipation, and diarrhea being a "Condition").

The present invention further provides methods for treating or preventing a Condition, comprising administering to a subject in need thereof a therapeutically effective amount of a Compound of the Invention. In certain embodiments, the Condition is pain (including acute pain, chronic pain (which includes but is not limited to, neuropathic pain, postoperative pain, and inflammatory pain), and surgical pain). The Compounds of the Invention are particularly useful for treating or preventing chronic pain.

In another aspect, the present disclosure provides a pharmaceutical composition comprising a therapeutically effective amount of a Compound of the Invention and one or more pharmaceutically acceptable carriers.

In another aspect, the present disclosure provides a pharmaceutical composition for treating a disorder responsive to the modulation of one or more opioid receptors, wherein the pharmaceutical composition comprises a therapeutically effective amount of a Compound of the Invention in a mixture with one or more pharmaceutically acceptable carriers.

In another aspect, the present disclosure provides a method of modulating one or more opioid receptors in a patient in need of said modulation, comprising administering to the patient a therapeutically effective amount of at least one Compound of the Invention.

In another aspect, the present disclosure provides Compounds of the Invention for use in treating one or more Conditions in a patient in need of said treatment.

In another aspect, the present disclosure provides Compounds of the Invention for use in treating pain in a mammal, such as acute pain, chronic pain (which includes but is not limited to, neuropathic pain, postoperative pain, and inflammatory pain), or surgical pain.

In another aspect, the present disclosure provides a Compound of the Invention for use in the manufacture of a medicament for treating or preventing a Condition in a patient.

In another aspect, the present disclosure provides a Compound of the Invention for use in the manufacture of a medicament for treating pain in a patient, such as acute pain, chronic pain, or surgical pain.

The present invention further provides methods for preparing a pharmaceutical composition, comprising admixing a Compound of the Invention and a pharmaceutically acceptable carrier to form the pharmaceutical composition.

A further aspect of the present invention is to provide radiolabeled Compounds of the Invention and the use of such compounds as radioligands for their binding to an opioid receptor in screening assays.

A further aspect of the present invention is to provide a method for screening a candidate compound for the ability to bind to an opioid receptor, comprising a) introducing a fixed concentration of the radio-labeled Compound of the Invention to the receptor under conditions that permit binding of the radio-labeled compound to the receptor to form a complex; b) titrating the complex with a candidate compound; and c) determining the binding of the candidate compound to said receptor.

The invention still further relates to a kit, comprising a container containing an effective amount of a Compound of the Invention and instructions for therapeutic use.

A further aspect of the present invention is to provide a method of making Compounds of the Invention.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

One aspect of the present invention is based on the use of Compounds of the Invention as modulators of opioid receptors.

Certain Compounds of the Invention are useful for modulating a pharmacodynamic response from one or more opioid receptors (μ, δ, κ) either centrally or peripherally, or both. The pharmacodynamic response may be attributed to the compound either stimulating (agonizing) or inhibiting (antagonizing) the one or more receptors. Certain Compounds of the Invention may inhibit (or antagonize) one opioid receptor, while also stimulating (or agonizing) one or more other receptors. Compounds of the Invention having agonist activity may be either full or partial agonists. Certain Compounds of the Invention also modulate the opioid receptor-like (ORL-1) receptor.

One aspect of the invention is based on the use of certain Compounds of the Invention as synthesis intermediates.

In one embodiment, Compounds of the Invention are compounds represented by Formula I:

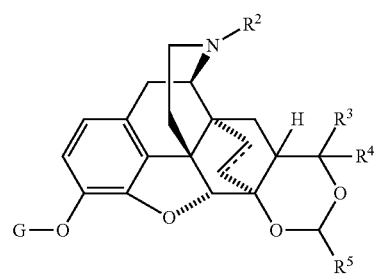

and the pharmaceutically acceptable salts, prodrugs, and solvates thereof, wherein:

G is $R^1$ or a hydroxyl protecting group PG;

$R^1$ is hydrogen, alkyl, alkenyl, alkynyl, (cycloalkyl)alkyl, (heterocyclo)alkyl, arylalkyl, or heteroarylalkyl, wherein the cycloalkyl, heterocyclo, aryl, and heteroaryl portions thereof are optionally substituted with 1, 2, or 3 substituents, each independently selected from the group consisting of hydroxy, halo, haloalkyl, amino, alkylamino, dialkylamino, carboxy, and alkoxycarbonyl;

$R^2$ is (a) hydrogen, cyano, carboxy, alkoxycarbonyl, or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, halo, haloalkyl, amino, alkylamino, dialkylamino, carboxy, and alkoxycarbonyl;

$R^3$ and $R^4$ are each independently selected from the group consisting of hydrogen, alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl;

$R^5$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl; and ⫸ is a single bond or a double bond.

When G is other than methyl, Compounds of the Invention are within the group of 1,3-dioxanomorphides.

When G is methyl, Compounds of the Invention are within the group of 1,3-dioxanocodides.

In another embodiment, Compounds of the Invention are compounds represented by Formula II:

II

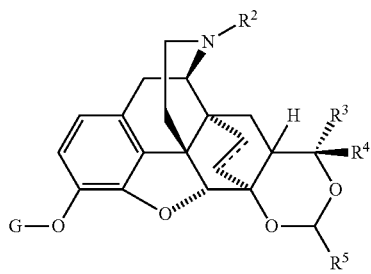

and the pharmaceutically acceptable salts, prodrugs, and solvates thereof, wherein $R^3$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl;

$R^4$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl; and G, $R^1$, $R^2$, $R^5$ and ⫸ are as defined above for Formula I.

In another embodiment, Compounds of the Invention are compounds represented by Formula III:

III

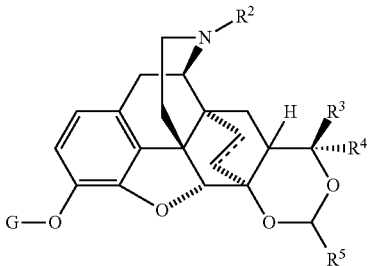

and the pharmaceutically acceptable salts, prodrugs, and solvates thereof, wherein $R^3$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl;

$R^4$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein any of which, when other than hydrogen, is optionally substituted with 1, 2, or 3 substituents, each independently selected from the group consisting of hydroxy, halo, haloalkyl, amino, alkylamino, dialkylamino carboxy, and alkoxycarbonyl; and G, $R^1$, $R^2$, $R^5$ and ⫸ are as defined above for Formula I.

In another embodiment, Compounds of the Invention are compounds represented by Formula IV:

IV

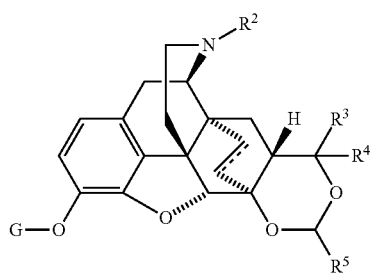

and the pharmaceutically acceptable salts, prodrugs, and solvates thereof, wherein G, $R^1$-$R^5$ and ⫸ are as defined for Formula I.

In another embodiment, Compounds of the Invention are compounds represented by Formula V:

V

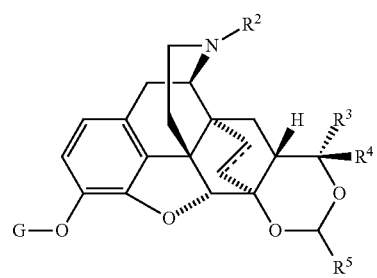

and the pharmaceutically acceptable salts, prodrugs, and solvates thereof, wherein G, $R^1$-$R^5$ and ⫸ are as defined for Formula II.

In another embodiment, Compounds of the Invention are compounds represented by Formula VI:

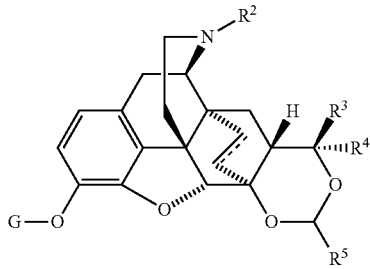

VI and the pharmaceutically acceptable salts, prodrugs, and solvates thereof, wherein G, $R^1$-$R^5$ and ⫽ are as defined for Formula III.

In another embodiment, Compounds of the Invention are compounds represented by Formula VII:

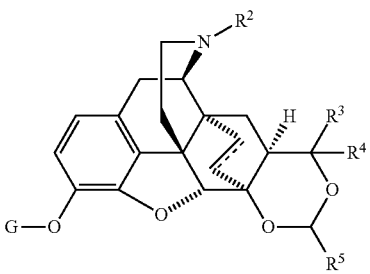

VII and the pharmaceutically acceptable salts, prodrugs, and solvates thereof, wherein G, $R^1$-$R^5$ and ⫽ are as defined for Formula I.

In another embodiment, Compounds of the Invention are compounds represented by Formula VIII:

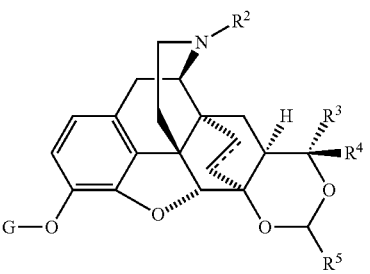

VIII and the pharmaceutically acceptable salts, prodrugs, and solvates thereof, wherein G, $R^1$-$R^5$ and ⫽ are as defined for Formula II.

In another embodiment, Compounds of the Invention are compounds represented by Formula IX:

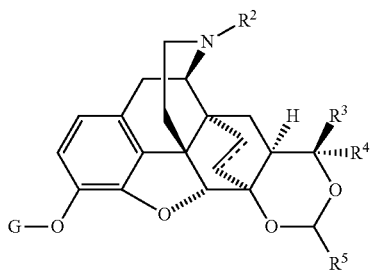

IX and the pharmaceutically acceptable salts, prodrugs, and solvates thereof, wherein G, $R^1$-$R^5$ and ⫽ are as defined for Formula III.

In another embodiment, Compounds of the Invention are compounds of any one of Formulae I-IX, wherein G is $R^1$.

In another embodiment, Compounds of the Invention are compounds of any one of Formulae I-IX, wherein G is $R^1$ and $R^1$ is hydrogen.

In another embodiment, Compounds of the Invention are compounds of any one of Formulae I-IX, wherein G is $R^1$ and $R^1$ is alkyl, alkenyl, or alkynyl. In one embodiment, $R^1$ is $C_{1-4}$ alkyl, $C_{2-4}$ alkenyl, or $C_{2-4}$ alkynyl. In another embodiment, $R^1$ is methyl, ethyl, n-propyl, iso-propyl, n-butyl, tert-butyl, iso-butyl, or sec-butyl, and advantageously $R^1$ is methyl. In another embodiment, $R^1$ is ethenyl, propenyl, isopropenyl, butenyl, or sec-butenyl. In another embodiment, $R^1$ is ethynyl, propynyl, butynyl, or 2-butynyl.

In another embodiment, Compounds of the Invention are compounds of any one of Formulae I-IX, wherein G is $R^1$ and $R^1$ is (cycloalkyl)alkyl, (heterocyclo)alkyl, arylalkyl, or heteroarylalkyl, wherein the cycloalkyl, heterocyclo, aryl, or heteroaryl portions thereof are optionally substituted with 1, 2, or 3 substituents, each independently selected from the group consisting of hydroxy, halo, haloalkyl, amino, alkylamino, dialkylamino, carboxy, and alkoxycarbonyl.

Suitable (cycloalkyl)alkyl groups for $R^1$ include $C_{3-7}$ cycloalkyl($C_{1-4}$)alkyl groups. In certain embodiment, $R^1$ is a $C_{3-6}$ cycloalkyl($C_{1-4}$)alkyl group, wherein the cycloalkyl portion is optionally substituted with 1, 2, or 3 substituents, each independently selected from the group consisting of hydroxy, halo, haloalkyl, amino, alkylamino, dialkylamino, carboxy, and alkoxycarbonyl. In another embodiment, $R^1$ is cyclopropyl($C_{1-4}$)alkyl, cyclopentyl($C_{1-4}$)alkyl, or cyclohexyl($C_{1-4}$)alkyl, wherein the cycloalkyl portion is optionally substituted with 1 or 2 substituents, each independently selected from the group consisting of hydroxy, halo, halo($C_{1-4}$)alkyl, amino, ($C_{1-4}$) alkylamino, di($C_{1-4}$)alkylamino, carboxy, and $C_{1-4}$ alkoxycarbonyl. In another embodiment, $R^1$ is unsubstituted (cyclopropyl)methyl, 2-(cyclopropyl)ethyl or 3-(cyclopropyl)propyl.

Suitable (heterocyclo)alkyl groups for $R^1$ include 5- or 6-membered heterocyclo($C_{1-4}$)alkyl, wherein the heterocyclo portion is optionally substituted with 1, 2, or 3 substituents, each independently selected from the group consisting of hydroxy, halo, haloalkyl, amino, alkylamino, dialkylamino, carboxy, and alkoxycarbonyl; and preferably optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl. In another embodiment, $R^1$ is unsubstituted 5- or 6-membered heterocyclo($C_{1-4}$)alkyl, such as 4-morpholinyl($C_{1-4}$)alkyl.

Suitable arylalkyl groups for $R^1$ include aryl($C_{1-4}$)alkyl groups wherein the aryl portion is optionally substituted with 1, 2, or 3 substituents, each independently selected from the group consisting of hydroxy, halo, haloalkyl, amino, alkylamino, dialkylamino, carboxy, and alkoxycarbonyl; and preferably optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl. In another embodiment, $R^1$ is $C_{6-10}$ aryl($C_{1-4}$)alkyl substituted with one or two substituents each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl. In another embodiment, $R^1$ is benzyl, phenethyl, or naphthylmethyl substituted with 1 or 2 substituents, each independently selected from the group consisting of hydroxy, fluorine, bromine, iodine, chlorine, trifluoromethyl, amino, methylamino, dimethylamino, carboxy, methoxycarbonyl, and ethoxycarbonyl. In another embodiment, $R^1$ is unsubstituted $C_{6-10}$ aryl$(C_{1-4})$alkyl, such as benzyl, phenethyl, 3-phenylpropyl, 4-phenylbutyl, naphthylmethyl, 2-naphthylethyl, 3-naphthylpropyl, and 4-naphthylbutyl; typically benzyl and phenethyl, and especially benzyl.

Suitable heteroarylalkyl groups for $R^1$ include heteroaryl $(C_{1-4})$alkyl groups wherein the heteroaryl portion is optionally substituted with 1, 2, or 3 substituents, each independently selected from the group consisting of hydroxy, halo, haloalkyl, amino, alkylamino, dialkylamino, carboxy, and alkoxycarbonyl; and preferably optionally substituted with 1 or 2 substituents, each independently selected from the group consisting of hydroxy, halo, halo$(C_{1-4})$alkyl, amino, $C_{1-4}$ alkylamino, di$(C_{1-4})$alkylamino, carboxy, and $C_{1-4}$ alkoxycarbonyl. In another embodiment, $R^1$ is 5- or 6-membered heteroaryl$(C_{1-4})$alkyl substituted with 1 or 2 substituents, each independently selected from the group consisting of hydroxy, halo, halo$(C_{1-4})$alkyl, amino, $C_{1-4}$ alkylamino, di$(C_{1-4})$alkylamino, carboxy, and $C_{1-4}$alkoxycarbonyl; and typically each independently selected from the group consisting of hydroxy, halo, halo$(C_{1-2})$alkyl, amino, $C_{1-2}$ alkylamino, di$(C_{1-2})$alkylamino, carboxy, and $C_{1-2}$alkoxycarbonyl. In another embodiment, $R^1$ is 5- or 6-membered, N-containing heteroaryl$(C_{1-4})$alkyl, and especially heteroaryl$(C_{1-2})$alkyl, such as pyridinylmethyl (pyridin-2-ylmethyl, pyridin-3-ylmethyl or pyridin-4-ylmethyl), wherein the heteroaryl portion is substituted with 1 or 2 substituents, each independently selected from the group consisting of hydroxy, fluorine, bromine, iodine, chlorine, trifluoromethyl, amino, methylamino, dimethylamino, carboxy, methoxycarbonyl, and ethoxycarbonyl. In another embodiment, $R^1$ is unsubstituted 5- or 6-membered, N-containing heteroaryl $(C_{1-4})$alkyl, and especially heteroaryl$(C_{1-2})$alkyl, such as pyridinylmethyl (pyridin-2-ylmethyl, pyridin-3-ylmethyl or pyridin-4-ylmethyl).

In another embodiment, Compounds of the Invention are compounds of any one of Formulae I-IX, wherein $R^2$ is hydrogen, cyano, carboxy, alkoxycarbonyl, or carboxamido. In this aspect of the invention, preferably $R^2$ is hydrogen, cyano, $C_{1-4}$ alkoxycarbonyl, —CONH$_2$, —CON(H)C$_{1-4}$ alkyl, —CON(C$_{1-4}$ alkyl)$_2$, or —CON(H)Ph.

In another embodiment, Compounds of the Invention are compounds of any one of Formulae I-IX, wherein $R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, halo, haloalkyl, amino, alkylamino, dialkylamino, carboxy, and alkoxycarbonyl. Useful compounds include those where $R^2$ is $C_{1-6}$ alkyl, $C_{2-6}$ alkenyl, $C_{2-6}$ alkynyl, $C_{3-7}$ cycloalkyl, $C_{3-7}$ cycloalkenyl, 5- or 6-membered heterocyclo, aryl, 5- or 6-membered heteroaryl, $C_{3-7}$ cycloalkyl$(C_{1-4})$alkyl, $C_{3-7}$ cycloalkenyl$(C_{1-4})$ alkyl, 5- or 6-membered heterocyclo $(C_{1-4})$alkyl, aryl$(C_{1-4})$alkyl, 5- or 6-membered heteroaryl $(C_{1-4})$alkyl, aryl$(C_{1-4})$alkoxycarbonyl, or 5- or 6-membered heteroaryl$(C_{1-4})$ alkoxycarbonyl, any of which is optionally substituted with 1, 2, or 3 substituents, each independently selected from the group consisting of hydroxy, halo, haloalkyl, amino, alkylamino, dialkylamino, carboxy, and alkoxycarbonyl. In another embodiment, $R^2$ is $C_{1-6}$ alkyl, $C_{2-6}$ alkenyl, $C_{2-6}$ alkynyl, $C_{3-7}$ cycloalkyl, $C_{3-7}$ cycloalkenyl, 5- or 6-membered heterocyclo, $C_{6-10}$ aryl, 5- or 6-membered heteroaryl, $C_{3-7}$ (cycloalkyl)$(C_{1-4})$alkyl, $C_{3-7}$ (cycloalkenyl) $(C_{1-4})$alkyl, 5- or 6-membered heterocyclo$(C_{1-4})$alkyl, $C_{6-10}$ aryl$(C_{1-4})$alkyl, 5- or 6-membered heteroaryl$(C_{1-4})$alkyl, $C_{6-10}$ aryl$(C_{1-4})$alkoxycarbonyl, or 5- or 6-membered heteroaryl$(C_{1-4})$alkoxycarbonyl, any of which is optionally substituted with 1, 2, or 3 substituents, each independently selected from the group consisting of hydroxy, halo, halo $(C_{1-4})$alkyl, amino, $C_{1-4}$ alkylamino, di$(C_{1-4})$alkylamino, carboxy, and $C_{1-4}$ alkoxycarbonyl, and preferably optionally substituted with 1 or 2 substituents, each independently selected from the group consisting of hydroxy, halo, trifluoromethyl, amino, methylamino, ethylamino, dimethylamino, diethylamino, carboxy, methoxycarbonyl, and ethoxycarbonyl. In another embodiment, $R^2$ is $C_{3-7}$ (cycloalkyl)$(C_{1-4})$ alkyl or $C_{3-7}$ (cycloalkenyl)$(C_{1-4})$alkyl, and especially $C_{3-7}$ (cycloalkyl)$(C_{1-4})$alkyl, such as cyclopropyl$(C_{1-4})$alkyl, cyclopentyl$(C_{1-4})$alkyl, or cyclohexyl$(C_{1-4})$alkyl, optionally substituted with 1, 2, or 3 substituents, each independently selected from the group consisting of hydroxy, halo, halo $(C_{1-4})$alkyl, amino, $C_{1-4}$ alkylamino, di$(C_{1-4})$alkylamino, carboxy, and $C_{1-4}$ alkoxycarbonyl, and preferably optionally substituted with 1 or 2 substituents, each independently selected from the group consisting of hydroxy, halo, trifluoromethyl, amino, methylamino, ethylamino, dimethylamino, diethylamino, carboxy, methoxycarbonyl, and ethoxycarbonyl. In another embodiment, $R^2$ is unsubstituted (cyclopropyl)methyl, 2-(cyclopropyl)ethyl or 3-(cyclopropyl)propyl.

In another embodiment, Compounds of the Invention are compounds of any one of Formulae I, IV, and VII, wherein $R^3$ and $R^4$ are each independently selected from the group consisting of hydrogen, $C_{1-6}$ alkyl, $C_{2-6}$ alkenyl, $C_{2-6}$ alkynyl, $C_{3-7}$ cycloalkyl, $C_{3-7}$ cycloalkenyl, heterocyclo, aryl, heteroaryl, $C_{3-7}$ cycloalkyl$(C_{1-4})$alkyl, $C_{3-7}$ cycloalkenyl$(C_{1-4})$ alkyl, heterocyclo$(C_{1-4})$alkyl, aryl$(C_{1-4})$alkyl, and heteroaryl $(C_{1-4})$alkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl. In this aspect of the invention, preferably $R^3$ and $R^4$ are each independently selected from the group consisting of hydrogen, $C_{1-6}$ alkyl, and $C_{2-6}$alkenyl, wherein the $C_{1-6}$ alkyl and $C_{2-6}$ alkenyl groups are optionally substituted with 1, 2, or 3 substituents, each independently selected from the group consisting of hydroxy, halo, haloalkyl, amino, alkylamino, dialkylamino, carboxy, and alkoxycarbonyl; and more typically $R^3$ and $R^4$ are both unsubstituted $C_{1-6}$ alkyl.

In another embodiment, Compounds of the Invention are compounds of any one of Formulae II, II, V, VI, VIII, and IX, wherein $R^3$ is selected from the group consisting of hydrogen, $C_{1-6}$ alkyl, $C_{2-6}$ alkenyl, $C_{2-6}$alkynyl, $C_{3-7}$ cycloalkyl, $C_{3-7}$ cycloalkenyl, heterocyclo, aryl, heteroaryl, $C_{3-7}$ cycloalkyl $(C_{1-4})$alkyl, $C_{3-7}$ cycloalkenyl$(C_{1-4})$alkyl, heterocyclo$(C_{1-4})$ alkyl, aryl$(C_{1-4})$alkyl, and heteroaryl$(C_{1-4})$alkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl; and $R^4$ is selected from the group consisting of hydrogen, $C_{1-6}$ alkyl, $C_{2-6}$ alkenyl, $C_{2-6}$alkynyl, $C_{3-7}$ cycloalkyl, $C_{3-7}$ cycloalkenyl, heterocyclo, aryl, heteroaryl, $C_{3-7}$ cycloalkyl$(C_{1-4})$alkyl, $C_{3-7}$ cycloalkenyl$(C_{1-4})$alkyl, heterocyclo$(C_{1-4})$alkyl, aryl$(C_{1-4})$ alkyl, and heteroaryl$(C_{1-4})$alkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl. In one embodiment, $R^3$ and $R^4$ are the same. In another embodiment, $R^3$ and $R^4$ are different. In another embodiment, Compounds of the Invention are compounds of any one of Formulae II, III, V, VI, VIII, and IX, wherein $R^3$ is methyl and $R^4$ is tert-butyl.

In another embodiment, Compounds of the Invention are compounds of any one of Formulae I-IX, wherein $R^5$ is selected from the group consisting of hydrogen, $C_{1-6}$ alkyl, $C_{2-6}$ alkenyl, $C_{2-6}$ alkynyl, $C_{3-7}$ cycloalkyl, $C_{3-7}$ cycloalkenyl, heterocyclo, aryl, heteroaryl, $C_{3-7}$ cycloalkyl($C_{1-4}$)alkyl, $C_{3-7}$ cycloalkenyl($C_{1-4}$)alkyl, heterocyclo($C_{1-4}$)alkyl, aryl($C_{1-4}$) alkyl, and heteroaryl($C_{1-4}$)alkyl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl. In another embodiment, $R^5$ is selected from the group consisting of hydrogen, $C_{1-6}$, alkyl, $C_{2-6}$ alkenyl, $C_{2-6}$ alkynyl, $C_{3-7}$ cycloalkyl, $C_{3-7}$ cycloalkenyl, heterocyclo, aryl, and heteroaryl, wherein any of which, when other than hydrogen, is optionally substituted with 1, 2, or 3 substituents, each independently selected from the group consisting of hydroxy, halo, haloalkyl, amino, alkylamino, dialkylamino, carboxy, and alkoxycarbonyl. Preferably, $R^5$ is hydrogen, $C_{1-6}$ alkyl, $C_{2-6}$ alkenyl, $C_{3-7}$ cycloalkenyl, 5- or 6-membered heterocyclo, phenyl, naphthyl, or 5- or 6-membered heteroaryl, wherein any of which, when other than hydrogen, is optionally substituted with 1, 2, or 3, substituents each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl; and more preferably $R^5$ is hydrogen, $C_{1-6}$ alkyl, or phenyl.

In another embodiment, Compounds of the Invention are compounds of any one of Formulae I-IX, wherein ⫽ is a single bond.

In another embodiment, Compounds of the Invention are compounds of any one of Formulae I-IX, wherein ⫽ is a double bond.

In another embodiment, Compounds of the Invention are compounds of Formula V, wherein G is $R^1$, $R^3$ is methyl and $R^4$ is tert-butyl, represented by Formula X:

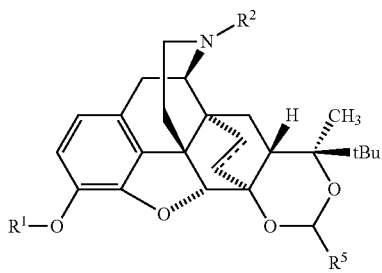

X and the pharmaceutically acceptable salts, prodrugs, and solvates thereof, wherein $R^1$, $R^2$, $R^5$ and ⫽ are as defined for Formula V.

In another embodiment, Compounds of the Invention are compounds of Formula X, wherein ⫽ is a single bond, represented by Formula XI:

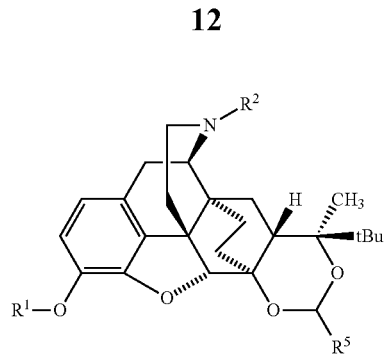

XI and the pharmaceutically acceptable salts, prodrugs, and solvates thereof.

In another embodiment, Compounds of the Invention are compounds of Formula X, wherein ⫽ is a double bond, represented by Formula XII:

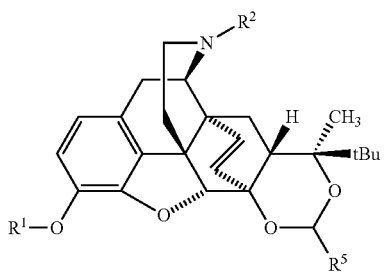

XII and the pharmaceutically acceptable salts, prodrugs, and solvates thereof.

In another embodiment, Compounds of the Invention are compounds of any one of Formulae X-XII, wherein:
$R^1$ is hydrogen, $C_{1-6}$ alkyl, or benzyl;
$R^2$ is $C_{2-6}$alkenyl, cyclopropyl($C_{1-4}$)alkyl, cyclopentyl ($C_{1-4}$)alkyl, or cyclohexyl($C_{1-4}$)alkyl, optionally substituted with 1, 2, or 3 substituents each, independently selected from the group consisting of hydroxy, halo, halo($C_{1-4}$)alkyl, amino, $C_{1-4}$alkylamino, di($C_{1-4}$)alkylamino, carboxy, and $C_{1-4}$ alkoxycarbonyl; and
$R^5$ is hydrogen, $C_{1-6}$ alkyl, or phenyl.

In another embodiment, Compounds of the Invention are compounds of any one of Formulae X-XII, wherein $R^2$ is unsubstituted $C_{2-6}$ alkenyl or unsubstituted cyclopropyl ($C_{1-4}$)alkyl, and $R^1$ and $R^5$ are as defined above for Formulae X-XII.

In another embodiment, Compounds of the Invention are compounds of Formula X, wherein $R^2$ is (cyclopropyl)methyl represented by Formula XIII:

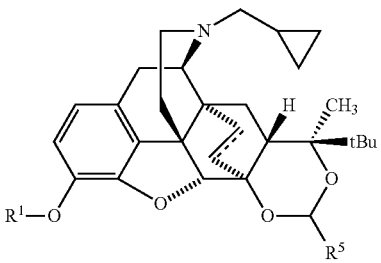

XIII and the pharmaceutically acceptable salts, prodrugs, and solvates thereof, wherein $R^1$, $R^5$, and ⫽ are as defined for Formula X.

In another embodiment, Compounds of the Invention are compounds of Formula XIII, wherein ⫽ is a single bond represented by Formula XIV:

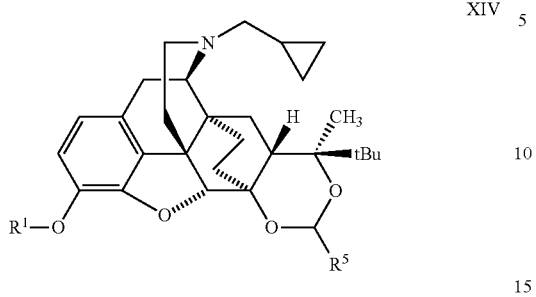

XIV and the pharmaceutically acceptable salts, prodrugs, and solvates thereof, wherein $R^1$ and $R^5$ are as defined for Formula XIII.

In another embodiment, Compounds of the Invention are compounds of Formula XIII, wherein ⫽ is a double bond, represented by Formula XV:

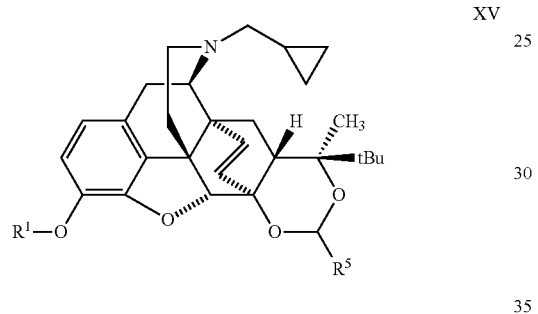

XV and the pharmaceutically acceptable salts, prodrugs, and solvates thereof, wherein $R^1$ and $R^5$ are as defined for Formula XIII.

In another embodiment, Compounds of the Invention are compounds of any one of Formulae XIII-XV, wherein $R^1$ is hydrogen, $C_{1-6}$ alkyl, or benzyl; and $R^5$ is hydrogen, $C_{1-6}$ alkyl, or phenyl; and the pharmaceutically acceptable salts, prodrugs, and solvates thereof.

In another embodiment, Compounds of the Invention are compounds of any one of Formulae XIII-XV, wherein $R^2$ is unsubstituted $C_{2-6}$ alkenyl or unsubstituted cyclopropyl $(C_{1-4})$alkyl, and $R^1$ and $R^5$ are as defined above for Formulae XIII-XV.

In another embodiment, Compounds of the Invention include:

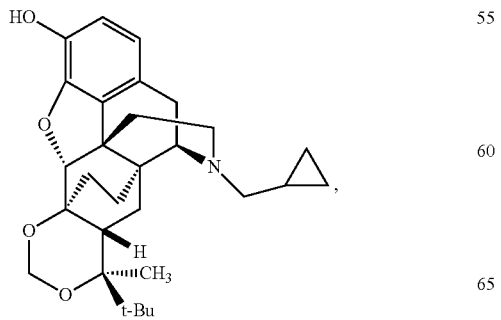

-continued

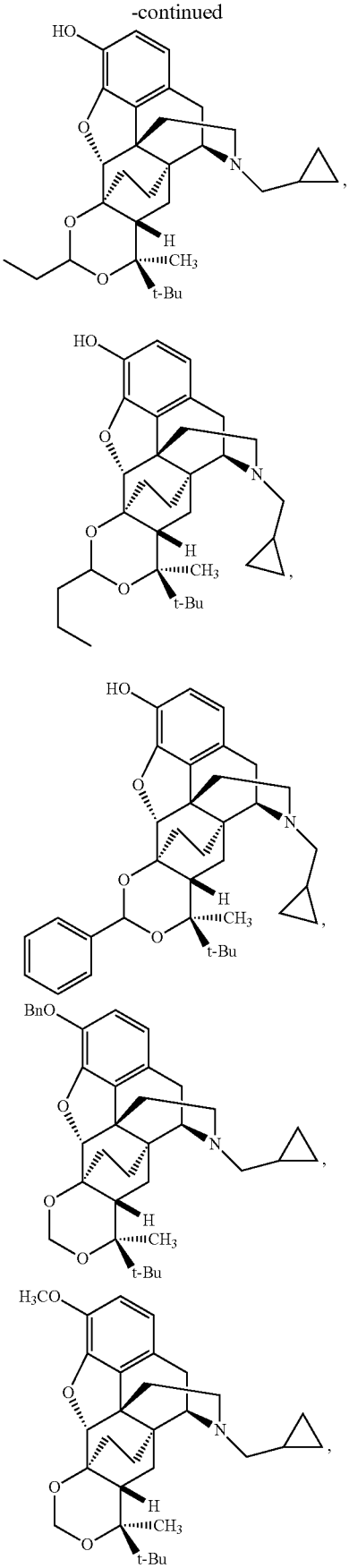

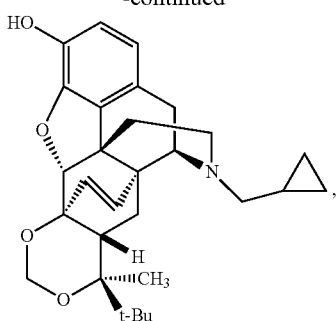,
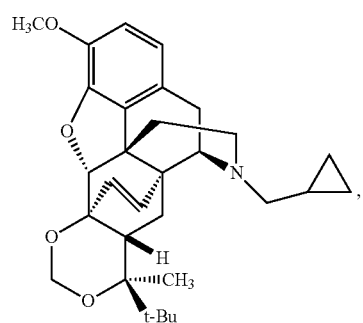,
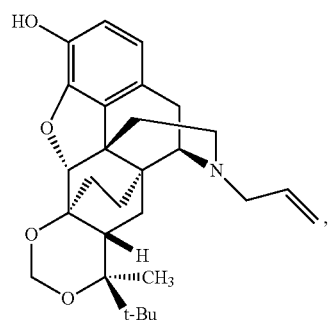,
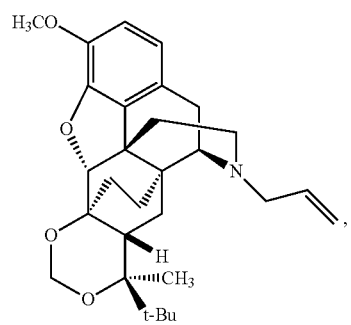,
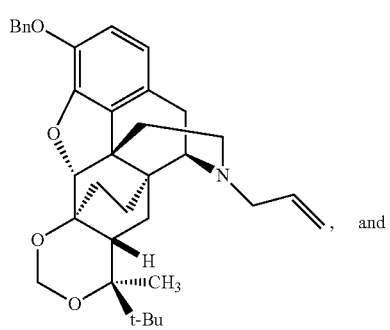, and
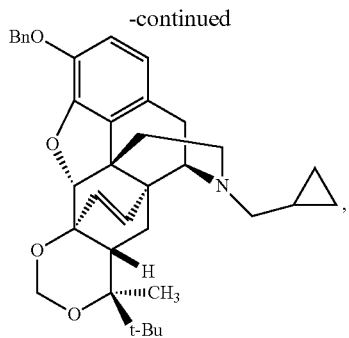,
the pharmaceutically acceptable salts, prodrugs, and solvates thereof.
In another embodiment, Compounds of the Invention include:
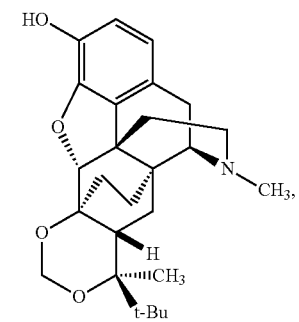,
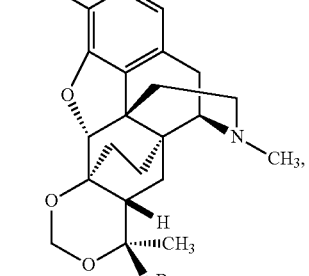,
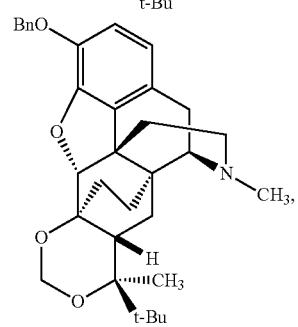,
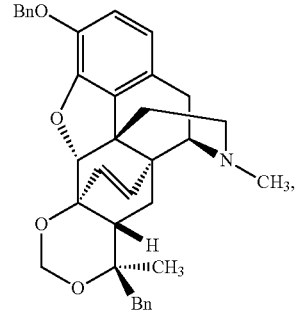,

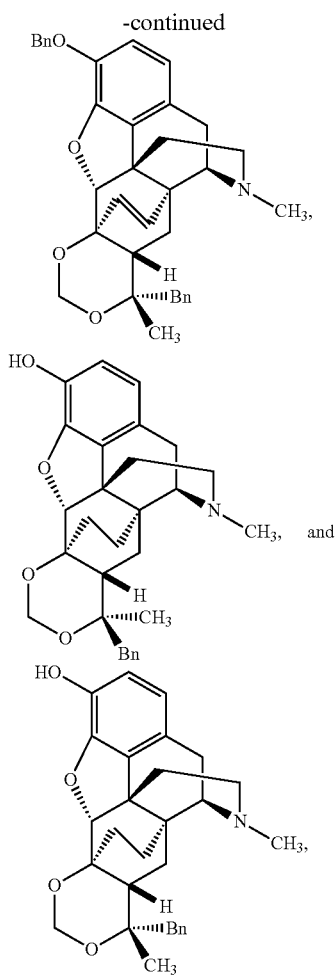

and the pharmaceutically acceptable salts, prodrugs, and solvates thereof.

In another embodiment, Compounds of the Invention are compounds of any one of Formulae I-IX, wherein G is a hydroxyl protecting group PG.

In another embodiment, Compounds of the Invention are represented by Formula XVI:

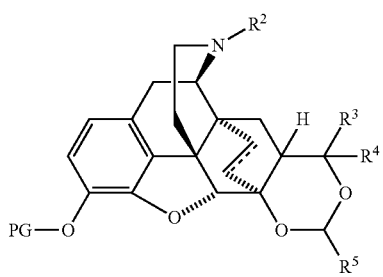

XVI wherein $R^2$-$R^5$ and ⫽ are as defined for Formula I above and PG is a hydroxyl protecting group. Suitable and preferable definitions for $R^2$-$R^5$ are those described above for compounds of any one of Formulae I-IX.

In another embodiment, Compounds of the Invention are represented by Formula XVII:

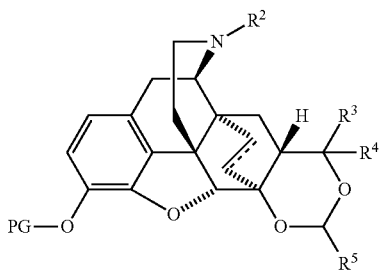

XVII wherein $R^2$-$R^5$ and ⫽ are as defined for Formula I above and PG is a hydroxyl protecting group. Suitable and preferable definitions for $R^2$-$R^5$ are those described above for compounds of any one of Formulae I-VI.

In another embodiment, Compounds of the Invention are represented by Formula XVIII:

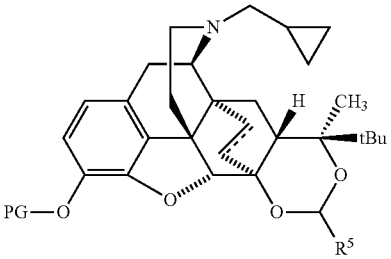

XVIII wherein $R^5$ and ⫽ are as defined for Formula I above and PG is a hydroxyl protecting group. Suitable and preferable definitions for $R^5$ are those described above for compounds of any one of Formulae I-VI and XII-XV.

Suitable hydroxyl protecting groups for PG are well known and include, for example, any suitable hydroxyl protecting group disclosed in Wuts, P. G. M. & Greene, T. W., *Greene's Protective Groups in Organic Synthesis,* 4rd Ed., pp. 16-430 (J. Wiley & Sons, 2007), herein incorporated by reference in its entirety. The term "hydroxy protecting group" as used herein refers to a group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular synthetic scheme planned. Suitable hydroxy protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Greene, T. W. and Wuts, P. G. M., above. Additional hydroxy protecting groups can be found, for example, in U.S. Pat. No. 5,952,495, U.S. Patent Appl. Pub. No. 2008/0312411, WO 2006/035195, and WO 98/02033, which are herein incorporated in their entireties. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

It will be apparent to a person of ordinary skill in the art in view of this disclosure that certain groups included in the definitions of $R^1$ and PG are overlapping, such as tert-butyl, benzyl, etc., and, thus, certain Compounds of the Invention having $R^1$ groups that act as hydroxyl protecting groups can be pharmaceutically active as described herein.

In one embodiment, the hydroxyl protecting group PG is selected from the group consisting of alkyl, arylalkyl, heterocyclo, (heterocyclo)alkyl, acyl, silyl, and carbonate, any of which are optionally substituted.

In another embodiment, the hydroxyl protecting group PG is an alkyl group, typically an optionally substituted $C_{1-6}$ alkyl group, and suitably unsubstituted methyl or tert-butyl.

In another embodiment, the hydroxyl protecting group PG is an arylalkyl group. Suitable arylalkyl groups include, for example, an unsubstituted benzyl group, substituted benzyl groups, such as p-methoxybenzyl, and naphthylmethyl.

In another embodiment, the hydroxyl protecting group PG is a heterocyclo group, such as unsubstituted tetrahydropyranyl or optionally substituted tetrahydropyranyl.

In another embodiment, the hydroxyl protecting group PG is a (heterocyclo)alkyl group. Suitable (heterocyclo)alkyl groups include, for example, 4-morpholinyl($C_{1-4}$)alkyl groups, such as, 2-(4-morpholinyl)ethyl.

In another embodiment, the hydroxyl protecting group PG is a silyl group. The term "silyl" as employed herein refers to the group having the following structure:

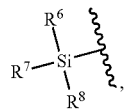

wherein $R^6$, $R^7$, and $R^8$ are each independently selected from the group consisting of alkyl, cycloalkyl, aryl, (cycloalkyl)alkyl, or arylalkyl, any of which is optionally substituted. In one embodiment, the silyl group is trimethyl silyl, tert-butyldimethyl silyl, tert-butyldiphenyl silyl, or tri-isopropyl silyl.

In another embodiment, the hydroxyl protecting group PG is an acyl group. The term "acyl" as employed herein refers to the following structure:

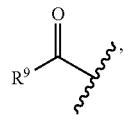

wherein $R^9$ is alkyl, cycloalkyl, aryl, (cycloalkyl)alkyl, or arylalkyl, any of which is optionally substituted. The acyl group can be, for example, $C_{1-4}$ alkylcarbonyl (such as, for example, acetyl), arylcarbonyl (such as, for example, benzoyl), levulinoyl, or pivaloyl. In another embodiment, the acyl group is benzoyl.

In another embodiment, the hydroxyl protecting group is a carbonate group. The term "carbonate" as employed herein refers to the following structure:

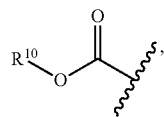

wherein $R^{10}$ is alkyl, alkenyl, cycloalkyl, aryl, (cycloalkyl)alkyl, or arylalkyl, any of which is optionally substituted. Typically, $R^{10}$ is $C_{1-10}$ alkyl (e.g., 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl. In one embodiment, the carbonate group is benzyloxycarbonyl.

The present invention also pertains to the preparation of Compounds of the Invention. Accordingly, the present invention is directed to a process for preparing compounds of any one of Formulae I-XV, comprising reacting the corresponding diol, such as a compound of Formula XIX

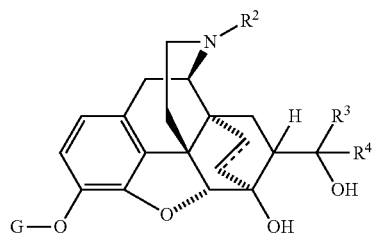

XIX wherein G and $R^2$-$R^4$ are as defined above, with $(R^5CH_2)_2SO$, wherein $R^5$ is as defined for any of the Formulae I-XV, in the presence of a trialkylsilyl halide and an aprotic solvent, to give compounds of any one of Formulae I-XV.

In one embodiment, $R^5$ in $(R^5CH_2)_2SO$ is hydrogen, $C_{1-6}$ alkyl, $C_{2-6}$ alkenyl, $C_{3-7}$ cycloalkenyl, 5- or 6-membered heterocyclo, phenyl, naphthyl, or 5- or 6-membered heteroaryl, wherein any of which, when other than hydrogen, is optionally substituted with 1, 2, or 3 substituents, each independently selected from the group consisting of hydroxy, halo, halo($C_{1-4}$)alkyl, amino, $C_{1-4}$alkylamino, di($C_{1-4}$)alkylamino, carboxy, and $C_{1-4}$ alkoxycarbonyl. In another embodiment, $R^5$ is hydrogen, $C_{1-6}$ alkyl, or phenyl.

In another embodiment, said $(R^5CH_2)_2SO$ is selected from the group consisting of dimethyl sulfoxide, di(n-propyl)sulfoxide, di(n-butyl)sulfoxide, and dibenzyl sulfoxide.

Typically, the trialkylsilyl halide is a tri($C_{1-6}$ alkyl)silyl halide, and more typically a tri($C_{1-4}$ alkyl)silyl halide. In one embodiment, the trialkylsilyl halide is selected from the group consisting of trimethylsilyl chloride, trimethylsilyl bromide, trimethylsilyl iodide, or a combination thereof.

The aprotic solvent can be any solvent that is incapable of acting as a proton donor. Suitable aprotic solvents include, for example, tetrahydrofuran (THF), methylene chloride ($CH_2Cl_2$), chloroform ($CH_3Cl$), toluene, and acetonitrile. In one embodiment, the aprotic solvent is tetrahydrofuran.

The process of the present invention can be carried out at a temperature of from about 0° C. to about 40° C., and typically the process is conducted at an ambient temperature. Preferably, the process of the present invention is conducted at room temperature, i.e., at a temperature from about 20° C. to about 25° C.

In another embodiment, $R^2$ in the compound of Formula XIX is cyclopropyl($C_{1-4}$) alkyl, cyclopentyl($C_{1-4}$)alkyl, or cyclohexyl($C_{1-4}$)alkyl, any of which are optionally substituted with 1, 2, or 3 substituents, each independently selected from the group consisting of hydroxy, halo, halo($C_{1-4}$)alkyl, amino, $C_{1-4}$alkylamino, di($C_{1-4}$)alkylamino, carboxy, and $C_{1-4}$ alkoxycarbonyl. In another embodiment, $R^3$ and $R^4$ in the compound of Formula XIX are each independently selected from the group consisting of hydrogen, $C_{1-6}$ alkyl, and $C_{2-6}$ alkenyl, wherein the $C_{1-6}$ alkyl and $C_{2-6}$ alkenyl groups are optionally substituted with 1, 2, or 3 substituents, each independently selected from the group consisting of hydroxy, halo, haloalkyl, amino, alkylamino, dialkylamino, carboxy, and alkoxycarbonyl.

In another embodiment, the process of the present invention provides Compounds of the Invention where G is $R^1$. In another embodiment, the process of the prevent invention provides Compounds of the Invention represented by Formula XV:

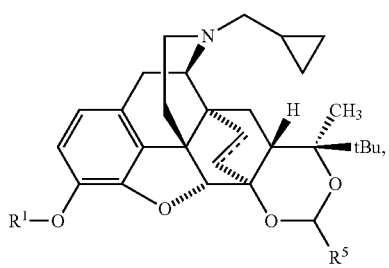

XV wherein $R^1$ and $R^5$ are as defined above. Advantageously, $R^1$ is hydrogen.

Optional substituents attached to aryl, phenyl and heteroaryl rings each take the place of a hydrogen atom that would otherwise be present in any position on the aryl, phenyl or heteroaryl rings.

Useful halo or halogen groups include fluorine, chlorine, bromine and iodine.

Useful alkyl groups are selected from straight-chain and branched-chain $C_{1-10}$ alkyl groups. Typical $C_{1-10}$ alkyl groups include methyl, ethyl, propyl, isopropyl, butyl, sec-butyl, tert-butyl, iso-butyl, pentyl, 3-pentyl, hexyl, heptyl, octyl, nonyl and decyl, among others. In one embodiment, useful alkyl groups are selected from straight chain $C_{1-6}$ alkyl groups and branched chain $C_{3-6}$alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain $C_{2-6}$ alkyl groups and branched chain $C_{3-6}$ alkyl groups. Typical $C_{2-6}$ alkyl groups include ethyl, propyl, isopropyl, butyl, sec-butyl, tert-butyl, iso-butyl, pentyl, 3-pentyl, hexyl among others. In one embodiment, useful alkyl groups are selected from straight chain $C_{1-4}$ alkyl groups and branched chain $C_{3-4}$alkyl groups. Typical $C_{1-4}$ alkyl groups include methyl, ethyl, propyl, isopropyl, butyl, sec-butyl, tert-butyl, iso-butyl.

Useful cycloalkyl groups are selected from saturated cyclic hydrocarbon groups containing one to three rings having from three to twelve carbon atoms (i.e., $C_3$-$C_{12}$ cycloalkyl) or the number of carbons designated. In one embodiment, the cycloalkyl has one or two rings. In another embodiment, the cycloalkyl is a $C_3$-$C_8$ cycloalkyl. Exemplary cycloalkyl groups include cyclopropyl, cyclobutyl, cyclopentyl, cyclohexyl, cycloheptyl, cyclooctyl, norbornyl, decalin, and adamantyl.

Useful cycloalkenyl groups are selected from partially unsaturated (i.e., containing one or two double bonds) cyclic hydrocarbon groups containing one to three rings having from four to twelve carbon atoms (i.e., $C_4$-$C_{12}$ cycloalkenyl) or the number of carbons designated. In one embodiment, the cycloalkenyl has one or two rings. In another embodiment, the cycloalkenyl is a $C_3$-$C_8$ cycloalkenyl. In one embodiment, the cycloalkenyl group contains one double bond. Exemplary cycloalkenyl groups containing one double bond include cyclobutenyl, cyclopentenyl, cyclohexenyl, cycloheptenyl, cyclooctenyl, cyclononenyl, and cyclodecenyl. In another embodiment, the cycloalkenyl group contains two double bonds. Preferably, the cycloalkenyl groups containing two double bonds have from five to twelve carbon atoms (i.e., $C_5$-$C_{12}$ cycloalkadienyl). Exemplary cycloalkenyl groups having two double bonds include cyclopentadienyl, cyclohexadienyl, cycloheptadienyl, cyclooctadienyl, cyclononadienyl, and cyclodecadienyl.

Useful alkenyl groups are selected from straight-chain and branched-chain $C_{2-6}$ alkenyl groups, preferably $C_{2-4}$alkenyl. Typical $C_{2-6}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl.

Useful alkynyl groups are selected from straight-chain and branched-chain $C_{2-6}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups.

Useful haloalkyl groups include any of the above-mentioned $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful hydroxyalkyl groups include any of the above-mentioned $C_{1-10}$ alkyl groups substituted by one or more hydroxy groups, such as monohydroxyalkyl and dihydroxyalkyl groups (e.g., hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 2,3-dihydroxypropyl, 3-hydroxybutyl, 4-hydroxybutyl, 2-hydroxy-1-methylpropyl, and 1,3-dihydroxyprop-2-yl).

Useful alkoxy groups include oxygen substituted by one of the $C_{1-10}$ alkyl groups mentioned above (e.g., methoxy, ethoxy, propoxy, iso-propoxy, butoxy, tert-butoxy, iso-butoxy, sec-butoxy, pentyloxy, hexyloxy, heptyloxy, octyloxy, nonyloxy and decyloxy).

Useful alkoxyalkyl groups include any of the above-mentioned $C_{1-10}$ alkyl groups substituted with any of the above-mentioned alkoxy groups (e.g., methoxymethyl, methoxyethyl, methoxypropyl, methoxybutyl, ethoxymethyl, 2-ethoxyethyl, 3-ethoxypropyl, 4-ethoxybutyl, propoxymethyl, iso-propoxymethyl, 2-propoxyethyl, 3-propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups mentioned above (e.g., fluoromethoxy, difluoromethoxy, trifluoromethoxy, and 2,2,2-trifluoroethoxy).

Useful (cycloalkyl)alkyl groups include any of the above-mentioned $C_{1-10}$ alkyl groups substituted with any of the above-mentioned cycloalkyl groups (e.g., (cyclopropyl)methyl, 2-(cyclopropyl)ethyl, (cyclopropyl)propyl, (cyclobutyl)methyl, (cyclopentyl)methyl, and (cyclohexyl)methyl).

Useful (cycloalkenyl)alkyl groups include any of the above-mentioned $C_{1-10}$ alkyl groups substituted with any of the above-mentioned cycloalkenyl groups (e.g., (cyclobutenyl)methyl, 2-(cyclobutenyl)ethyl, (cyclobutenyl)propyl, (cyclopentenyl)methyl, (cyclohexenyl)methyl, and (cyclopentadienyl)methyl).

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

Useful aryloxy groups include oxygen substituted by one of the aryl groups mentioned above (e.g., phenoxy).

Useful arylalkyl groups include any of the above-mentioned $C_{1-10}$ alkyl groups substituted by any of the above-mentioned aryl groups (e.g., benzyl and phenethyl).

Useful aralkyloxy or arylalkoxy groups include oxygen substituted by one of the above-mentioned arylalkyl groups (e.g., benzyloxy).

Useful (arylalkoxy)carbonyl groups include a carbonyl group substituted by any of the above-mentioned arylalkoxy groups (e.g., (benzyloxy)carbonyl).

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., pyrrol-1-yl, 1H-pyrrol-2-yl and 1H-pyrrol-3-yl), imidazolyl (e.g., imidazol-1-yl, 1H-imidazol-2-yl and 1H-imidazol-4-yl), tetrazolyl (e.g., tetrazol-1-yl and tetrazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl).

Useful heteroarylalkyl groups include any of the above-mentioned $C_{1-10}$ alkyl groups substituted by any of the above-mentioned heteroaryl groups (e.g., (thien-2-yl)methyl, 2-furylmethyl, (pyrrol-1-yl)methyl, and 2-(1H-pyrrol-2-yl)ethyl).

Useful heteroarylalkoxy groups include oxygen substituted by one of the above-mentioned heteroaryl groups.

Useful (heteroarylalkoxy)carbonyl groups include a carbonyl group substituted by any of the above-mentioned heteroarylalkoxy groups.

The terms "heterocyclic" and "heterocyclo" are used herein to mean saturated or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. In one embodiment, the 3- to 7-membered monocyclic heterocyclic ring is either a saturated, or unsaturated non-aromatic ring. A 3-membered heterocyclo can contain up to 1 heteroatom, a 4-membered heterocyclo can contain up to 2 heteroatoms, a 5-membered heterocyclo can contain up to 4 heteroatoms, a 6-membered heterocyclo can contain up to 4 heteroatoms, and a 7-membered heterocyclo can contain up to 5 heteroatoms. Each heteroatom is independently selected from nitrogen, which can be quaternized; oxygen; and sulfur, including sulfoxide and sulfone. The 3- to 7-membered heterocyclo can be attached via a nitrogen or carbon atom. A 7- to 10-membered bicyclic heterocyclo contains from 1 to 4 heteroatoms independently selected from nitrogen, which can be quaternized; oxygen; and sulfur, including sulfoxide and sulfone. The 7- to 10-membered bicyclic heterocyclo can be attached via a nitrogen or carbon atom. Examples of the heterocyclic rings include, but are not limited to, pyrrolidinyl, piperidinyl, piperazinyl, morpholinyl, imidazolinyl, pyrazolidinyl, tetrahydrofuranyl, oxazolidinyl, 2-oxooxazolidinyl, tetrahydrothienyl, imidazolidinyl, hexahydropyrimidinyl, and benzodiazepines.

Useful (heterocyclo)alkyl groups include any of the above-mentioned $C_{1-10}$ alkyl groups substituted by any of the above-mentioned heterocyclic groups (e.g., (pyrrolidin-2-yl)methyl, (pyrrolidin-1-yl)methyl, (piperidin-1-yl)methyl, (morpholin-1-yl)methyl, (2-oxooxazolidin-4-yl)methyl, 2-(2-oxooxazolidin-4-yl)ethyl, (2-oxo-imidazolidin-1-yl) methyl, (2-oxo-imidazolidin-1-yl)ethyl, and (2-oxo-imidazolidin-1-yl)propyl).

As used herein, the term "amino" or "amino group" refers to —$NH_2$.

Useful aminoalkyl groups include any of the above-mentioned $C_{1-10}$ alkyl groups substituted with one or more amino group.

Useful diaminoalkyl groups include any of the above-mentioned $C_{1-10}$ alkyl groups substituted with two amino groups.

Useful alkylamino and dialkylamino groups are —$NHR^{11}$ and —$NR^{11}R^{12}$, respectively, wherein $R^{11}$ and $R^{12}$ are each independently selected from a $C_{1-10}$ alkyl group.

As used herein, the term "aminocarbonyl" refers to —$C(=O)NH_2$.

Useful alkylcarbonyl groups include a carbonyl group, i.e., —$C(=O)$—, substituted by any of the above-mentioned $C_{1-10}$ alkyl groups.

Useful alkoxycarbonyl groups include a carbonyl group substituted by any of the above-mentioned alkoxy groups (e.g., methoxycarbonyl, ethoxycarbonyl, propoxycarbonyl, iso-propoxycarbonyl, butoxycarbonyl, tert-butoxycarbonyl, iso-butoxycarbonyl, sec-butoxycarbonyl, and pentyloxycarbonyl).

Useful arylcarbonyl groups include a carbonyl group substituted by any of the above-mentioned aryl groups (e.g., benzoyl).

Useful alkylcarbonyloxy or acyloxy groups include oxygen substituted by one of the above-mentioned alkylcarbonyl groups.

Useful alkylcarbonylamino or acylamino groups include any of the above-mentioned alkylcarbonyl groups attached to an amino nitrogen, such as methylcarbonylamino.

As used herein, the term "carboxamido" refers to a radical of formula —$C(=O)NR^{13}R^{14}$, wherein $R^{13}$ and $R^{14}$ are each independently hydrogen, optionally substituted $C_{1-10}$ alkyl, or optionally substituted aryl. Exemplary carboxamido groups include —$CONH_2$, —$CON(H)CH_3$, —$CON(CH_3)_2$, and —$CON(H)Ph$.

Useful alkylaminocarbonyl and dialkylaminocarbonyl groups are any of the above-mentioned carboxamido groups, where $R^{13}$ is H and $R^{14}$ is $C_{1-10}$ alkyl or where $R^{13}$ and $R^{14}$ are each independently selected from a $C_{1-10}$ alkyl group, respectively.

As used herein, the term "sulfonamido" refers to a radical of formula —$SO_2NR^{15}R^{16}$, wherein $R^{15}$ and $R^{16}$ are each independently hydrogen, optionally substituted $C_{1-10}$ alkyl, or optionally substituted aryl. Exemplary sulfonamido groups include —$SO_2NH_2$, —$SO_2N(H)CH_3$, and —$SO_2N$(H)Ph.

Useful mercaptoalkyl groups include any of the above-mentioned $C_{1-10}$ alkyl groups substituted by a —SH group.

As used herein, the term "carboxy" refers to —COOH.

Useful carboxyalkyl groups include any of the above-mentioned $C_{1-10}$ alkyl groups substituted by —COOH.

As used herein, the terms "hydroxyl" or "hydroxy" refer to —OH.

As used herein, the term "cyano" refers to —CN.

As used herein, the term "ureido" refers to —NH—C(=O)—$NH_2$.

As used herein, the term "azido" refers to —$N_3$.

The term "ambient temperature" as used herein means the temperature of the surroundings. The ambient temperature indoors is the same as room temperature, which is from about 20° C. to about 25° C.

The term "about," as used herein in connection with a measured quantity, refers to the normal variations in that measured quantity, as expected by the skilled artisan making the measurement and exercising a level of care commensurate with the objective of measurement and the precision of the measuring equipment. Typically, the term "about" includes the recited number ±10%. Thus, "about 10" means 9 to 11.

As used herein, the term "optionally substituted" refers to a group that may be unsubstituted or substituted.

Optional substituents on optionally substituted groups, when not otherwise indicated, include one or more groups, typically 1, 2, or 3 groups, independently selected from the group consisting of halo, halo($C_{1-6}$)alkyl, aryl, heterocycle, cycloalkyl, $C_{1-6}$ alkyl, $C_{2-6}$alkenyl, $C_{2-6}$ alkynyl, aryl($C_{1-6}$) alkyl, aryl($C_{2-6}$)alkenyl, aryl($C_{2-6}$)alkynyl, cycloalkyl($C_{1-6}$) alkyl, heterocyclo($C_{1-6}$)alkyl, hydroxy($C_{1-6}$)alkyl, amino ($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, aryloxy, ar($C_{1-6}$)alkyloxy, carboxamido, sulfonamido, azido, $C_{1-6}$ alkoxy, halo($C_{1-6}$)alkoxy, carboxy, aminocarbonyl, (=O), and mercapto($C_{1-6}$) alkyl groups mentioned above. Preferred optional substituents include halo, halo($C_{1-6}$) alkyl, hydroxy($C_{1-6}$)alkyl, amino($C_{1-6}$)alkyl, hydroxy, nitro, $C_{1-6}$ alkyl, $C_{1-6}$ alkoxy, halo($C_{1-6}$)alkoxy, and amino.

Compounds of the Invention encompass all the salts of the disclosed compounds of Formulae I-XVIII. The present invention preferably includes all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

Compounds of the Invention also encompass solvates of any of the disclosed compounds of Formulae I-XVIII. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Invention may be present as solvated forms with a pharmaceutically acceptable solvent, such as water, methanol, ethanol, and the like, and it is intended that the invention includes both solvated and unsolvated forms of compounds of any of Formulae I-XVIII. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*: 603-604 (2001). A typical, non-limiting, process of preparing a solvate would involve dissolving a compound of any of Formulae I-XVIII in a desired solvent (organic, water, or a mixture thereof) at temperatures above about 20° C. to about 25° C., such as about 30° C. to about 70° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the Invention also encompass prodrugs of any of the disclosed compounds of Formulae I-XVIII. As used herein, prodrugs are considered to be any covalently bonded carriers that release the active parent drug in vivo. In general, such prodrugs will be a functional derivative of a compound of Formula I-XVIII which is readily convertible in vivo, e.g., by being metabolized, into the required compound of Formula I-XVIII. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds of any of Formulae I-XVIII having hydroxyalkyl or aminoalkyl as a substituent, and these may be prepared by reacting such parent compounds with anhydrides such as succinic anhydride.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Isotopically labeled Compounds of the Invention, as well as the pharmaceutically acceptable salts, prodrugs and solvates thereof, can be used as radioligands to test for the binding of compounds to an opioid receptor. For example, a radio-labeled Compound of the Invention can be used to characterize specific binding of a test or candidate compound to the receptor. Binding assays utilizing such radio-labeled compounds can provide an in vitro alternative to animal testing for the evaluation of chemical structure-activity relationships. For example, the receptor assay may be performed at a fixed concentration of a labeled compound of the invention and at increasing concentrations of a test compound in a competition assay. In a non-limiting embodiment, the present invention provides a method for screening a candidate compound for the ability to bind to an opioid receptor, comprising a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centres present in the respective molecular entities.

The term "streogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

Open terms such as "include," "including," "contain," "containing" and the like mean "comprising."

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^h$ Ed. (J. G. Hardman, L.E. Limbird and A. Goodman-Gilman eds., 2001)).

In certain embodiments, the Compound of the Invention is an agonist at one or more of the μ, δ and/or κ receptor. In certain non-limiting embodiments, the Compound of the Invention produces fewer side effects and/or less severe side effects than currently available analgesic opioid compounds when administered at doses producing equivalent levels of analgesia and/or anti-hyperalgesia.

In certain embodiments, Compounds of the Invention can be used in combination with at least one other therapeutic agent. The other therapeutic agent can be, but is not limited to, μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

Compounds of the Invention potently bind to the μ and/or κ and/or δ opioid receptors. Compounds of the Invention can be modulators at the μ and/or κ and/or δ opioid receptors, and therefore Compounds of the Invention can be used/administered to treat, or ameliorate, or for the prophylaxis of, pain.

In some embodiments, Compounds of the Invention are antagonists of the μ and/or κ opioid receptors.

In some embodiments, Compounds of the Invention are partial agonists of the μ and/or κ opioid receptors.

In another embodiments, Compounds of the Invention are agonists of the μ and/or κ opioid receptors.

Compounds of the Invention that are antagonists of the μ-opioid receptor or agonists of κ-opioid receptor, or both, can be used/administered to treat or ameliorate constipation. Compounds of the Invention that are agonists of μ-opioid receptor can be used/administered to treat or ameliorate diarrhea.

Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources. Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic pain or neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes but is not limited to pain caused by nerve injury such as, for example, the pain from which diabetics suffer.

Compounds of the Invention can also be used as an agent to treat withdrawal from alcohol addiction or drug addiction; and in treating or ameliorating constipation and diarrhea.

The present invention is also directed to the use of a compound represented by any of defined Formulae I-XV, or a pharmaceutically acceptable salt, prodrug or solvate thereof, in the manufacture of a medicament for treating a disorder responsive to the modulation of one or more opioids receptors (e.g., any of the disorders listed above) in an animal suffering from said disorder.

Furthermore, the present invention is directed to a method of modulating, in particular activating, one or more opioid receptors in an animal in need thereof, said method comprising administering to the animal at least one compound represented by any defined Formulae I-XV, or a pharmaceutically acceptable salt, prodrug or solvate thereof.

The present invention is also directed to the use of a compound represented by any of defined Formulae I-XV, or a pharmaceutically acceptable salt, prodrug or solvate thereof, in the manufacture of a medicament, in particular a medicament for modulating, in particular activating, one or more opioid receptors, in an animal in need thereof.

The tertiary alcohol group in buprenorphine is sensitive to acidic conditions. Therefore, buprenorphine decomposes in acidic environment forming EP Impurity F (Garret, E. R., et al., supra) or demethoxy-buprenorphine, EP Impurity I (Cone, E. J., et al., supra) It has been found that Compounds of the Invention are stable in certain conditions where buprenorphine would decompose. The rate of decomposition of buprenorphine and compound 3, prepared in Example 1 below, in acidic conditions was measured after having each of the compounds dissolved in water in the presence of 9 mol equivalents of HCl at 45° C. The decomposition was followed for 1 and 7 days. It was discovered that compound 3 remained essentially stable under conditions where 9% of buprenorphine decomposed after day 1 and 20% after day 7, thus, indicating that compound 3 has a decreased sensitivity towards acids when compared to buprenorphine.

Synthesis of Compounds

Compounds of the Invention can be prepared using methods known to those skilled in the art in view of this disclosure. For example, compounds of Formulae I-XVIII can be prepared as shown in the schemes below. Additional methods of synthesis are described and illustrated in the working examples set forth below.

The synthesis of the compounds usually starts with a Diels-Alder reaction of thebaine or oripavine with, for example, a vinyl ketone under formation of two epimers of the starting materials for preparing Compounds of the Invention, A-2 and A'-2 (Scheme 1).

Scheme 1
Synthesis of α-epimers A-2 and β-epimers A'-2 of starting materials for preparing Compounds of the Invention

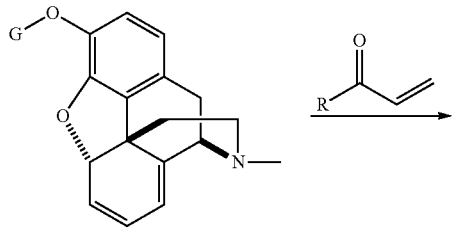

Thebaine (G = Me)
Oripavine (G = H)
A-1

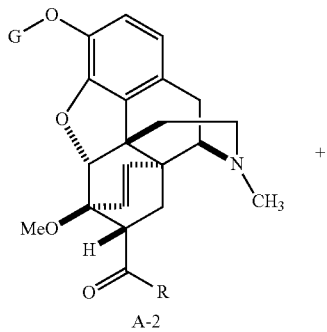

A-2

-continued

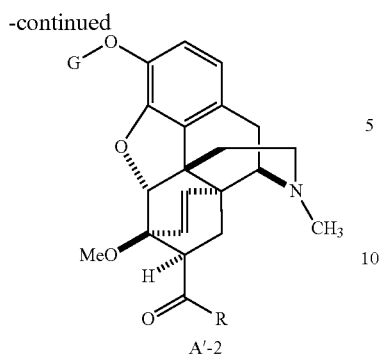

A'-2

In Scheme 1, G is $R^1$ or a hydroxyl protecting group as defined above for Formula I, and R is as defined above for $R^3$ or a group that can be converted to $R^3$.

The epimers A-2 and A'-2 can be synthesized and separated by methods described in the art, for example, in Marton J., et al., *Synthetic Communications* 25(6):829-848 (1995), and Bentley, K. W., *Journal of American Chemical Society* 89(13):3267-3273 (1967). Usually, the alpha (α) epimer A-2 is formed as the major component. The ketone A-2 or A'-2 can then be converted further through a series of transformations, which may include hydrogenation, N- and/or O-demethylation, Grignard or lithium alkyl addition as shown in Scheme 2 below, as described, for example, in Bentley, K. W., et al., *Journal of American Chemical Society* 89(13):3273-3280 (1967); Bentley, K. W., and Hardy, D. G., *Journal of American Chemical Society* 89(13):3281-3292 (1967); and Marton, J., et al., *Monatshefte für Chemie* 125:1229-1239 (1994).

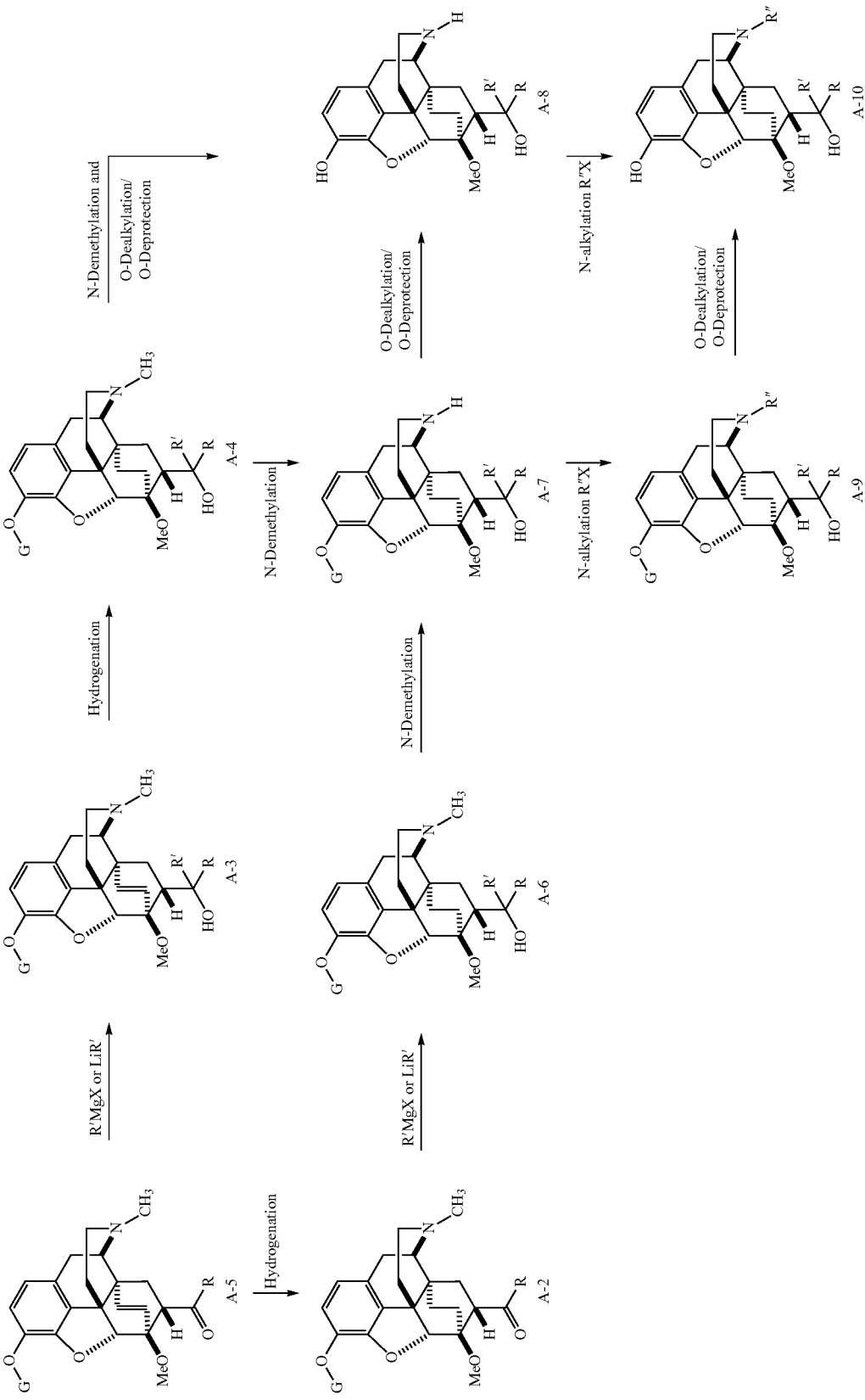

In Scheme 2, G is $R^1$ or a hydroxyl protecting group PG as defined above for Formula I, R and R' are as defined above for $R^3$ and $R^4$, respectively, or are functional groups that can be converted to $R^3$ or $R^4$. R" is as defined above for $R^2$ or a group that can be converted to $R^2$. X is halogen or tosylate. The corresponding beta (β) epimers can be prepared analogously starting from compound A'-2. The order of the steps described in Scheme 2 can be changed as desired. For example, the N-demethylation step can be conducted first prior to the hydrogenation step or the Grignard reaction. The corresponding unsaturated compounds can be prepared according to Scheme 2 omitting the hydrogenation step. The corresponding N-alkyl compounds, and especially N-methyl compounds, can be prepared according to Scheme 2, for example, by omitting the N-demethylation step and the N-alkylation step.

Scheme 3 describes a general synthesis of Compounds of the Invention:

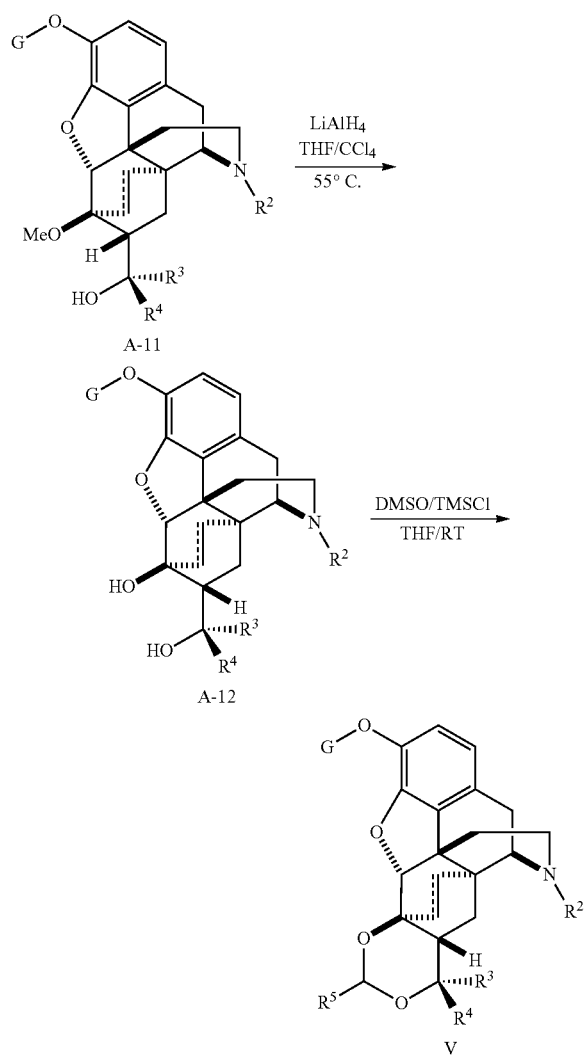

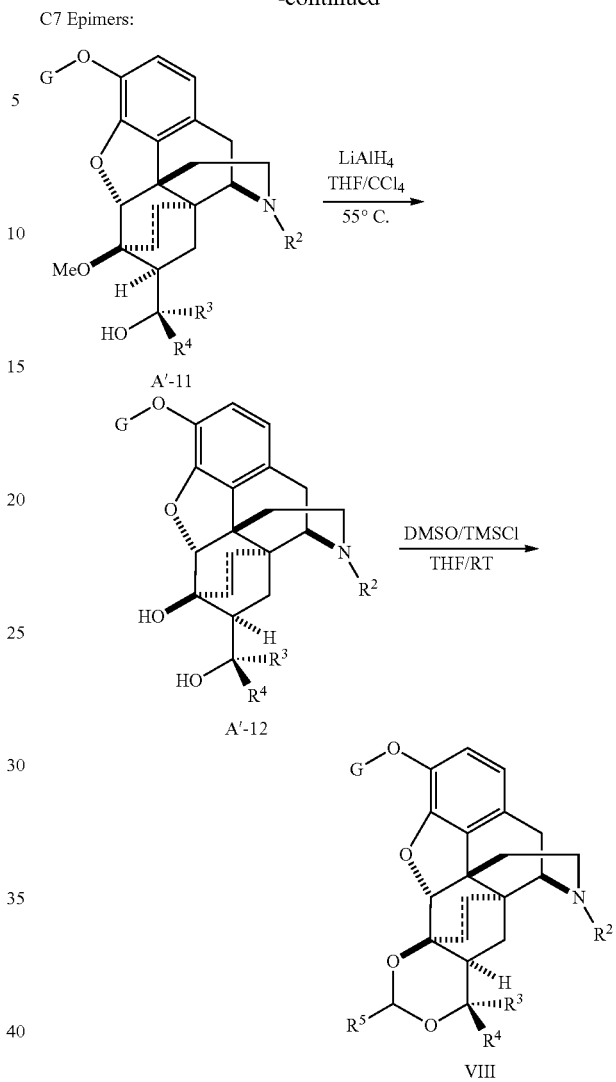

In Scheme 3, G, $R^2$-$R^5$, and ⫽ are as defined above for Formula I. DMSO provides compounds of Formulae V and VIII, where $R^5$ is hydrogen. When $(R^5CH_2)_2SO$, where $R^5$ is other than hydrogen, is used in place of DMSO, compounds of Formulae V and VIII are obtained, where $R^5$ is as defined above for Formula I. Instead of TMSCl, N-bromosuccinimide (NBS), phosphonyl chloride ($POCl_3$), and thionyl chloride ($SOCl_2$) can be used. Also, the reaction with TMSCl may optionally be conducted in the presence of a base, such as triethylamine or pyridine. The protecting group can be easily removed as desired as described above.

Compounds of Formulae V and VIII, and the intermediates A-11, A'-11, A-12, and A'-12, can be optionally modified by subsequent chemical transformations, for example, as shown in Scheme 4 below. The diols A-12 and A-14 can be prepared from buprenorphine derivatives by demethylation of the methoxy group at the 6-position of the morphinan ring by methods known in the art, for example, as described in Breeden, S. W., et al., *Helvetica Chimica Acta* 82:1978-1980 (1999). The acetals (A-15 and V) can be prepared from the diols following procedures described in the art, for example, in Hanessian, S., et al., *Journal of American Chemical Society* 94(25):8929-8931 (1972); Bal, B. S, and Pinnick, H. W., *J.*

*Org. Chem.* 44:3727-3728 (1979); Gu, Z.-M., et al., *J. Org. Chem.* 59:5162-5172 (1994); and Queiroz, E. F., et al., *Tetrahedron Letters* 40:697-700 (1999). It has been found that the tertiary alcohol is acid-labile and, therefore, the diols are preferably reacted in non-acidic conditions, such as with DMSO, or other sulfoxide, and TMSCl. Under standard acetal forming conditions, which are usually acidic, the starting material diol would decompose analogous to the decomposition of buprenorphine under acidic conditions.

quently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data:

Scheme 4

Examples of modifications of the G group

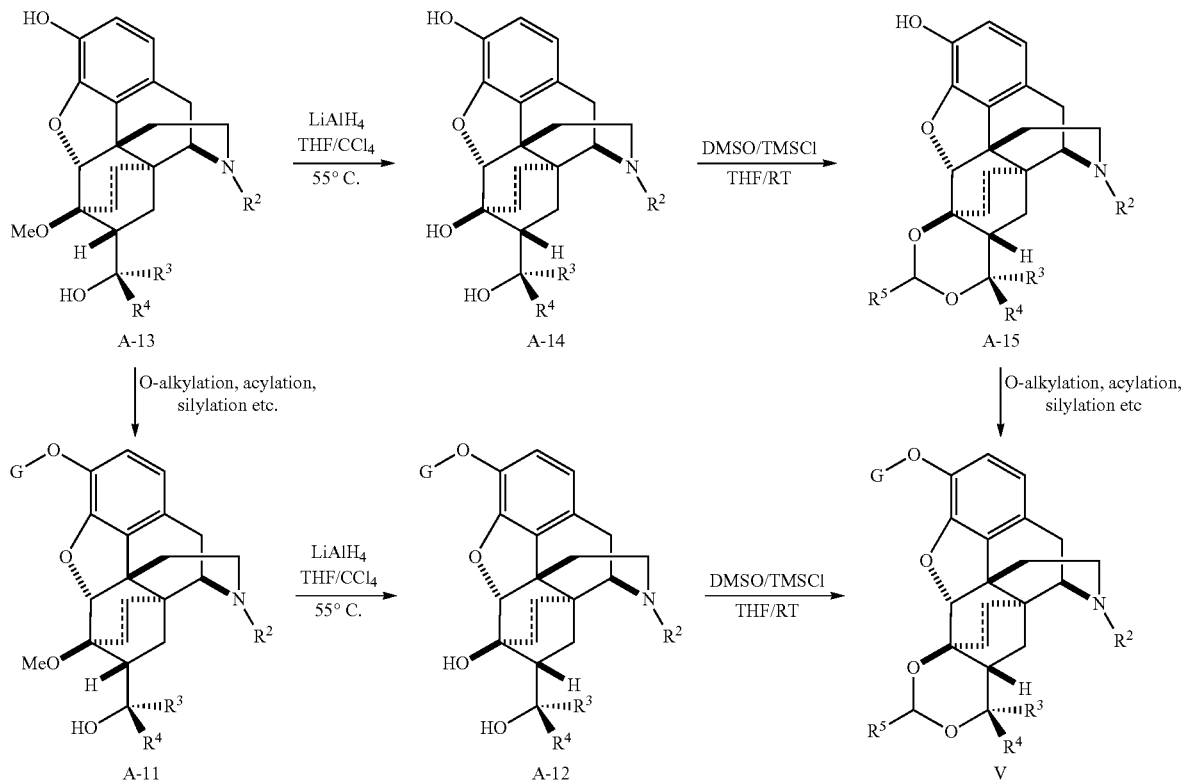

In Scheme 4, G, $R^2$-$R^5$, and ⫽ are as defined above for Formula I. The O-alkylation acylation, silylation, etc., modifications can be performed by methods known in the art. The corresponding beta (β) epimers can be prepared analogously starting from compound A'-12.

In Vitro Assay Protocols

μ-Opioid Receptor Binding Assay Procedures:

Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hours at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subse- Generally, the lower the $K_i$ value, the more effective Compounds of the Invention will be at treating or preventing pain or another Condition. Typically, Compounds of the Invention exhibit a $K_i$ (nM) of about 1000 or less for binding to μ-opioid receptors. In one embodiment, Compounds of the Invention exhibit a $K_i$ (nM) of about 300 or less for binding to μ-opioid receptors. In another embodiment, Compounds of the Invention exhibit a $K_i$ (nM) of about 100 or less for binding to μ-opioid receptors. In another embodiment, Compounds of the Invention exhibit a $K_i$ (nM) of about 10 or less for binding to μ-opioid receptors. In still another embodiment, Compounds of the Invention exhibit a $K_i$ (nM) of about 1 or less for binding to μ-opioid receptors. In still another embodiment, Compounds of the Invention exhibit a $K_i$ (nM) of about 0.1 or less for binding to μ-opioid receptors.

μ-Opioid Receptor Functional Assay Procedures:

[$^{35}$S]GTPγS functional assays were conducted using freshly thawed μ-receptor membranes prepared in-house from a cell line expressing recombinant μ opioid receptor in a HEK293 background or purchased from a commercial source (Perkin Elmer, Shelton, Conn.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hours. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data:

μ GTP $EC_{50}$ is the concentration of a compound providing 50% of the maximal response for the compound at a μ-opioid receptor. Typically, Compounds of the Invention exhibit a μ GTP $EC_{50}$ (nM) of about 5000 or less. In certain embodiments, Compounds of the Invention exhibit a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention exhibit a μ GTP $E_{max}$ (%) of greater than about 10%; or greater than about 20%. In certain embodiments, Compounds of the Invention exhibit a μ GTP Emax (%) of greater than about 50%; or greater than about 65%; or greater than about 75%; or greater than about 85%; or greater than about 100%.

κ-Opioid Receptor Binding Assay Procedures:

Membranes from HEK-293 cells expressing the recombinant human kappa opioid receptor (κ) or a cell line naturally expressing kappa opioid receptor were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hour at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data:

In certain embodiments, Compounds of the Invention exhibit a $K_i$ (nM) for κ receptors of about 10,000 or more (which, for purposes of this invention, is interpreted as having no binding to the κ receptors). Certain Compounds of the Invention exhibit a $K_i$ (nM) of about 20,000 or less for κ receptors. In certain embodiments, Compounds of the Invention exhibit a $K_i$ (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less for κ receptors.

κ-Opioid Receptor Functional Assay Procedures:

Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data:

κ GTP $EC_{50}$ is the concentration of a compound providing 50% of the maximal response for the compound at a κ receptor. Certain Compounds of the Invention exhibit a κ GTP $EC_{50}$ (nM) of about 20,000 or less to stimulate κ opioid receptor function. In certain embodiments, Compounds of the Invention exhibit a κ GTP $EC_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention exhibit a κ GTP $E_{max}$ (%) of greater than about 1%; or greater than about 5%; or greater than about 10%; or greater than about 20%. In certain embodiments, Compounds of the Invention exhibit a κ GTP $E_{max}$ (%) of greater than about 50%; or greater than about 75%; or greater than about 90%; or greater than about 100%.

δ-Opioid Receptor Binding Assay Procedures:

δ-Opioid Receptor Binding Assay Procedures can be conducted as follows. Radioligand dose-displacement assays can be 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM $MgCl_2$, 5% DMSO, 50 mM Trizma base, pH 7.4). Non-specific binding is determined in the presence of 25 μM unlabeled naloxone. All reactions are performed in 96-deep well polypropylene plates for 1 hour at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 µl ice-cold binding buffer. Filter plates are subsequently dried at 50° C. for 1-2 hours. Fifty µl/well scintillation cocktail (Perkin Elmer, Shelton, Conn.) is added and plates are counted in a Packard Top-Count for 1 min/well.

δ-Opioid Receptor Binding Data:

In certain embodiments, Compounds of the Invention can exhibit a $K_i$ (nM) for δ receptors of about 10,000 or more (which, for the purposes of this invention, is interpreted as having no binding to the δ receptors). Certain Compounds of the Invention can exhibit a $K_i$ (nM) of about 20,000 or less for δ receptors. In one embodiment, Compounds of the Invention can exhibit a Ki (nM) of about 10,000 or less; or of about 9000 or less for δ receptors. In another embodiment, Compounds of the Invention can exhibit a $K_i$ (nM) of about 7500 or less; or of about 6500 or less; or of about 5000 or less; or of about 3000 or less; or of about 2500 or less for δ receptors. In another embodiment, Compounds of the Invention can exhibit a $K_i$ (nM) of about 1000 or less; or of about 500 or less; or of about 350 or less; or of about 250 or less; or of about 100 or less; or of about 10 or less for δ receptors.

δ-Opioid Receptor Functional Assay Procedures:

Functional [$^{35}$S]GTPγS binding assays can be conducted as follows. δ opioid receptor membrane solution is prepared by sequentially adding final concentrations of 0.026 µg/µl δ membrane protein (Perkin Elmer, Shelton, Conn.), 10 µg/mL saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) is transferred to 96-shallow well polypropylene plates containing 10 µl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM NaH$_2$PO$_4$, 10 mM Na$_2$HPO$_4$, pH 7.4). Filter plates are subsequently dried at 50° C. for 1-2 hours. Fifty µl/well scintillation cocktail (Perkin Elmer, Shelton, Conn.) is added and plates were counted in a Packard Top-count for 1 min/well.

δ-Opioid Receptor Functional Data:

δ GTP EC$_{50}$ is the concentration of a compound providing 50% of the maximal response for the compound at a δ receptor. Certain Compounds of the Invention can exhibit a δ GTP EC$_{50}$ (nM) of about 20,000 or less; or about 10,000 or less. In certain embodiments, Compounds of the Invention can exhibit a δ GTP EC$_{50}$ (nM) of about 3500 or less; or of about 1000 or less; or of about 500 or less; or of about 100 or less; or of about 90 or less; or of about 50 or less; or of about 25 or less; or of about 10 or less.

δ GTP E$_{max}$ (%) is the maximal effect elicited by a compound relative to the effect elicited by met-enkephalin. Certain Compounds of the Invention can exhibit a δ GTP E$_{max}$ (%) of greater than about 1%; or of greater than about 5%; or of greater than about 10%. In one embodiment, Compounds of the Invention can exhibit a δ GTP E$_{max}$ (%) of greater than about 30%. In another embodiment, Compounds of the Invention can exhibit a δ GTP E$_{max}$ (%) of greater than about 50%; or of greater than about 75%; or of greater than about 90%. In another embodiment, Compounds of the Invention can exhibit a δ GTP E$_{max}$ (%) of greater than about 100%.

ORL-1 Receptor Binding Assay Procedure:

Membranes from recombinant HEK-293 cells expressing the human opioid receptor-like receptor (ORL-1) (Perkin Elmer, Shelton, Conn.) can be prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, Conn.; 87.7 Ci/mmole) with 12 µg membrane protein in a final volume of 500 µl binding buffer (10 mM MgCl$_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 µl ice-cold binding buffer. Filter plates are subsequently dried at 50° C. for 2-3 hours. Fifty µl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data:

Certain Compounds of the Invention can have a $K_i$ (nM) of about 5000 or less. In one embodiment, certain Compounds of the Invention can have a $K_i$ (nM) of about 1000 or less. In one embodiment, certain Compounds of the Invention can have a $K_i$ (nM) of about 500 or less. In other embodiments, the Compounds of the Invention can have a $K_i$ (nM) of about 300 or less; or of about 100 or less; or of about 50 or less; or of about 20 or less. In yet other embodiments, the Compounds of the Invention can have a $K_i$ (nM) of about 10 or less; or of about 1 or less; or of about 0.1 or less.

ORL-1 Receptor Functional Assay Procedure:

Membranes from recombinant HEK-293 cells expressing the human opioid receptor-like (ORL-1) (Perkin Elmer, Shelton, Conn.) can be prepared by lysing cells in ice-cold hypotonic buffer (2.5 mM Mg Cl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the Bio-Rad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 µg/µl ORL-1 membrane protein, 10 µg/ml saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) is transferred to 96-shallow well polypropylene plates containing 10 µl of 20× concentrated stock solutions of agonist/nociceptin prepared in DMSO.

Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 2-3 hours. Fifty μl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data:

ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) can have an ORL-1 GTP $EC_{50}$ (nM) of greater than about 10,000 (i.e. will not stimulate at therapeutic concentrations) In certain embodiments Compounds of the Invention can have an ORL-1 GTP $EC_{50}$ (nM) of about 20,000 or less. In one embodiment, the Compounds of the Invention can have an ORL-1 GTP $EC_{50}$ (nM) of about 10,000 or less; or of about 5000 or less; or of about 1000 or less. In still other embodiments, the Compounds of the Invention can have an ORL-1 GTP $EC_{50}$ (nM) of about 100 or less; or of about 10 or less; or of about 1 or less; or of about 0.1 or less.

ORL-1 GTP $E_{max}$ % is the maximal effect elicited by a compound relative to the effect elicited by nociceptin, a standard ORL-1 agonist. In certain embodiments, Compounds of the Invention can have an ORL-1 GTP $E_{max}$ of less than 10% (which, for the purposes of this invention, is interpreted as having antagonist activity at ORL-1 receptors). Certain Compounds of the Invention can have an ORL-1 GTP $E_{max}$ (%) of greater than 1%; or of greater than 5%; or of greater than 10%. In other embodiments, Compounds of the Invention can have an ORL-1 GTP $E_{max}$ of greater than 20%; or of greater than 50%; or of greater than 75%; or of greater than 88%; or of greater than 100%.

In Vivo Assays for Pain

Test Animals:

Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain:

To assess the actions of a Compound of the Invention for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% \, MPE = \frac{[(\text{post administration latency}) - (\text{pre-administration latency})]}{(20 \, \text{s} - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rats is placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) excape or attempted escape from the testing device; or 4) vocalization. Data are expressed as response latency(s) and the percentage of the maximal possible effect is calculated as described above for the tail flick test. The hot plate test is described in G. Woolfe and A. D. MacDonald, *J. Pharmacol. Exp. Ther.* 80:300-307 (1944).

Inflammatory Pain:

To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \, Reversal = \frac{[(\text{post administration } PWT) - (\text{pre-administration } PWT)]}{[(\text{baseline } PWT) - (\text{pre-administration } PWT)]} \times 100$$

Neuropathic Pain:

To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 3/8 curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat is gently restrained, its hindpaw is placed on a small round platform, and punctate pressure is applied to the dorsal surface of the hindpaw in a graded manner. The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus applied to the plantar surface of the hindpaw are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., *Intensive Care Med.* (26): 585-591 (2000).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in a patient in need thereof. The Compounds of the Invention can be administered to any patient requiring modulation of the opioid receptors. The term "patient" as used herein refers to any animal that may experience the beneficial effects of a Compound of the Invention. Foremost such animals are mammals, e.g., humans and companion animals, although the invention is not intended to be so limited.

When administered to a patient, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, suppositories, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., $16^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocalne to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially immediately release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release*, Vol. 2, Applications and Evaluation, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each patient's circumstances. Variations in dosing may occur depending upon typical factors such as the weight, age, gender and physical condition (e.g., hepatic and renal function) of the patient being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the patient per day, although they are typically from about 0.01 mg/kg of body weight to about 2500 mg/kg of body weight of the patient per day or from about 0.01 mg/kg of body weight to about 1000 mg/kg of body weight of the patient per day. In one embodiment, the effective dosage amount is about 100 mg/kg of body weight of the patient per day or less. In another embodiment, the effective dosage amount ranges from about 0.01 mg/kg of body weight to about 100 mg/kg of body weight of the patient per day of a Compound of the Invention, in another embodiment, about 0.02 mg/kg of body weight to about 50 mg/kg of body weight of the patient per day, and in another embodiment, about 0.025 mg/kg of body weight to about 20 mg/kg of body weight of the patient per day.

Administration can be as a single dose or as a divided dose. In one embodiment, an effective dosage amount is administered about every 24 hours until the Condition is abated. In another embodiment, an effective dosage amount is administered about every 12 hours until the Condition is abated. In another embodiment, an effective dosage amount is administered about every 8 hours until the Condition is abated. In another embodiment, an effective dosage amount is administered about every 6 hours until the Condition is abated. In another embodiment, an effective dosage amount is administered about every 4 hours until the Condition is abated. The effective dosage amounts described herein refer to total amounts administered; that is, if more than one Compound of the Invention is administered, the effective dosage amounts correspond to the total amount administered.

Where a cell capable of expressing the μ-opioid receptors is contacted with a Compound of the Invention in vitro, the amount effective for inhibiting or activating the μ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the δ-opioid receptors is contacted with a Compound of the Invention in vitro, the amount effective for inhibiting or activating the δ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the κ-opioid receptors is contacted with a Compound of the Invention in vitro, the amount effective for inhibiting or activating the κ-opioid receptors function in a cell can typically range from about $10^{-12}$ mol/L to about $10^{-4}$ mol/L, or from about $10^{-12}$ mol/L to about $10^{5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the ORL-1 receptor is contacted with a Compound of the Invention in vitro, the amount effective for inhibiting or activating the ORL-1 receptor function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Compounds of the Invention can be assayed in vitro or in vivo for the desired therapeutic or prophylactic activity prior to use in humans. Animal model systems can be used to demonstrate safety and efficacy. Certain Compounds of the Invention are expected to have an $ED_{50}$ for treating inflammatory pain ranging from about 0.5 mg/kg to about 20 mg/kg. Certain Compounds of the Invention are expected to produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the present invention, methods for treating or preventing a Condition in a patient in need thereof can further comprise co-administering to the patient an effective amount of a second therapeutic agent in addition to a Compound of the Invention (i.e., a first therapeutic agent). An effective amount of the second therapeutic agent can be known or determinable by a medical practitioner in view of this disclosure and published clinical studies. In one embodiment of the invention, where a second therapeutic agent is administered to a animal patient for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

A composition of the invention is prepared by a method comprising admixing a Compound of the Invention with a pharmaceutically acceptable carrier or excipient. Admixing can be accomplished using methods known for admixing a compound (or derivative) and a pharmaceutically acceptable carrier or excipient. In one embodiment, the Compound of the Invention is present in the composition in an effective amount.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

The compounds are named according to the IUPAC system. For purposes of illustration, the ring atoms of the compounds are numbered as diagrammed below:

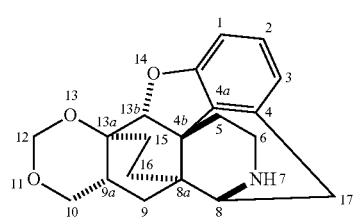

(4bS,8R,8aS,9aR,13aR,13bR)-5,6,7,8,9,9a,10,13b-octahydro-8a,13a-ethano-4,8-methanobenzofuro[3,2-e][1,3]dioxino[4,5-g]isoquinoline

EXAMPLES

Example 1

Preparation of (4bS,8R,8aS,9aR,10S,13aR,13bR)-10-tert-butyl-7-cyclopropylmethyl-5,6,7,8,9,9a,10,13b-octahydro-10-methyl-8a,13a-ethano-4,8-methanobenzofuro[3,2-e][1,3]dioxino[4,5-g]isoquinolin-1-ol (3)

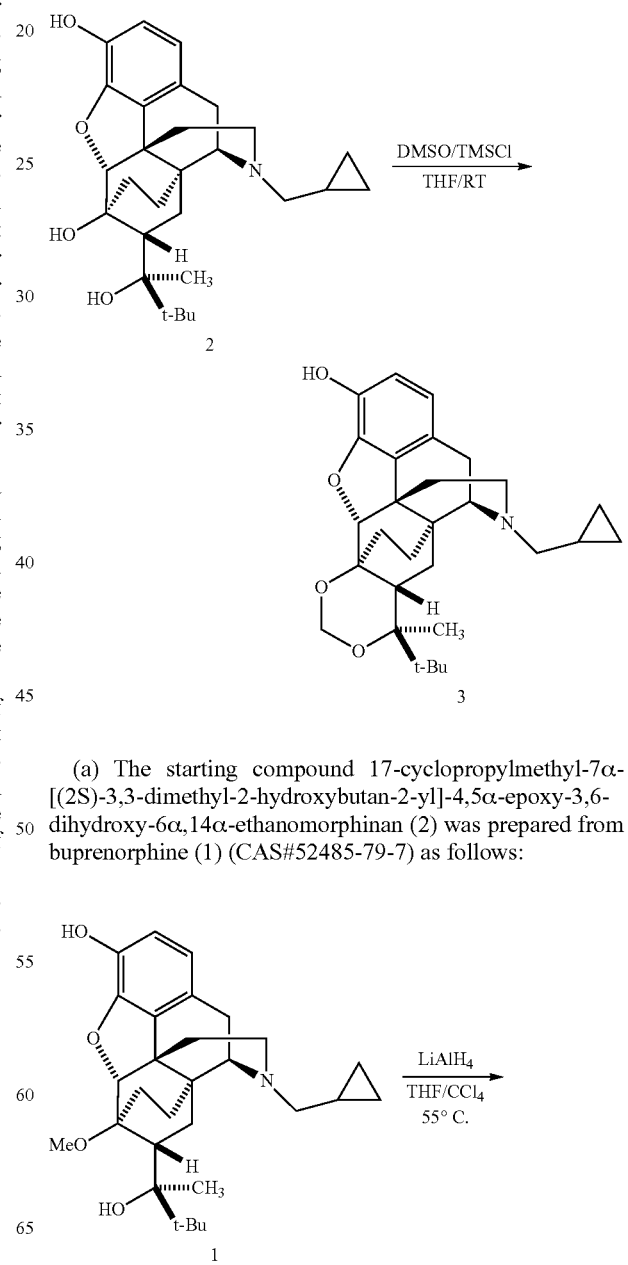

(a) The starting compound 17-cyclopropylmethyl-7α-[(2S)-3,3-dimethyl-2-hydroxybutan-2-yl]-4,5α-epoxy-3,6-dihydroxy-6α,14α-ethanomorphinan (2) was prepared from buprenorphine (1) (CAS#52485-79-7) as follows:

-continued

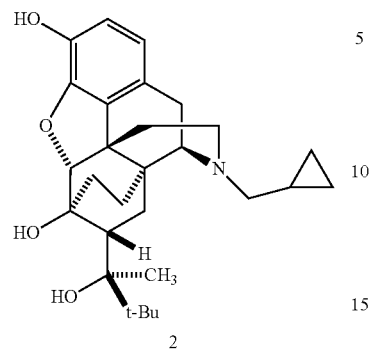

2

To a solution of buprenorphine (1) (10.0 g, 21.58 mMol) in CCl$_4$ (21.7 ml, 224.5 mMol) and THF (200 ml) was added at 0° C. LiAlH$_4$ (320 ml, 1.0 M, 320 mMol) in THF. The reaction mixture was heated to 55° C. for 24 h. The resulting reaction mixture was cooled to 0° C. and the reaction was quenched by slow, portion-wise addition of Na$_2$SO$_4$·10H$_2$O (103 g), followed by addition of EtOAc (400 ml). After 20 minutes agitation, the resulting slurry was filtered through the pre-packed Solka Floc-40 (18 g). The resulting wet cake was washed thoroughly with EtOAc (2×100 ml). The combined filtrate was concentrated to dryness, affording 13.5 g of crude compound 2 which was subsequently purified by column chromatography on silica gel to afford 6.03 g of compound 2 (62.2% yield) as a white solid with a purity of >99%.

$^1$H NMR δ (300 MHz, CDCl$_3$): 6.71 (d, 1H), 6.48 (d, 1H), 6.20 (bs, 1H), 5.14 (bs, 1H). 4.17 (s, 1H), 2.96-2.91 (m, 2H), 2.83 (dd, 1H), 2.54 (dd, 1H), 2.31-2.09 (m, 5H), 1.92-1.80 (m, 2H), 1.48-1.4 (m, 5H), 1.31-1.24 (m, 2H), 1.04 (s, 9H), 0.99-0.94 (m, 1H), 0.81-0.76 (m, 1H), 0.64-0.58 (m, 1H), 0.51-0.47 (m, 2H), 0.10-0.08 (m, 2H).

LC/MS (ESI), m/z=454.16 [M=H]$^+$ (Calc: 453.6).

Buprenorphine (1) is commercially available as a free base (e.g., American Custom Chemicals Corp.,) and as a hydrochloride salt (Aldrich), or it can be prepared as described in, for example, WO 2007/081506 or Machara, A., et al., *Adv. Synth. Catal* 354:613-626 (2012).

(b) To a solution of DMSO (2.1 ml, 28.7 mMol) in THF (10 ml), at ambient temperature, was added trimethylsilyl chloride (TMSCl) (2.7 ml, 20.8 mMol). After 30 minute agitation, a solution of compound 2 (1.5 g, 3.3 mMol) in THF (12.5 ml) was added and the mixture was stirred at ambient temperature. After 24 h reaction time at ambient temperature, the reaction conversion was about 85% at which point the reaction was quenched by addition of saturated aqueous NaHCO$_3$ solution (100 ml). The resulting mixture was extracted with EtOAc (2×100 ml). The combined organic extracts were dried over MgSO$_4$, filtered, and concentrated to give 2.7 g of crude product. After purification by column chromatography on silica gel, 0.52 g of the title compound 3 (34.4% yield) was obtained with a purity of >99%.

$^1$H NMR δ (300 MHz, CDCl$_3$): 6.70 (d, 1H), 6.51 (d, 1H), 5.03 (d, 1H). 4.78 (d, 1H), 4.25 (d, 1H), 3.01-2.95 (m, 1H), 2.89-2.80 (m, 1H), 2.63-2.62 (m, 1H), 2.37-2.01 (m, 8H), 1.75-1.70 (m, 1H), 1.45-1.23 (m, 5H), 1.15-1.02 (m, 11H), 0.81-0.73 (m, 2H), 0.51-0.46 (m, 2H), 0.11-0.08 (m, 2H).

LC/MS (ESI), m/z=466.2 [M=H]$^+$ (Calc: 465.6).

Example 2

Preparation of (4bS,8R,8aS,9aR,10S,13aR,13bR)-10-tert-butyl-7-cyclopropylmethyl-12-ethyl-5,6,7,8,9,9a,10,13b-octahydro-10-methyl-8a,13a-ethano-4,8-methanobenzofuro[3,2-e][1,3]dioxino[4,5-g]isoquinolin-1-ol (4)

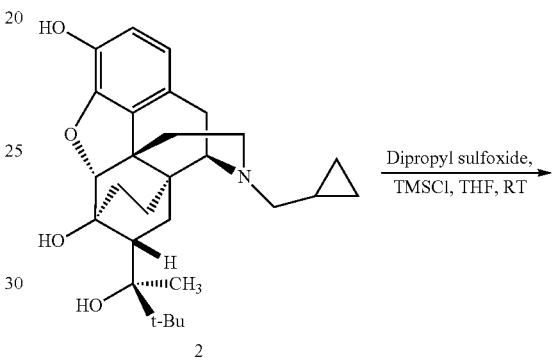

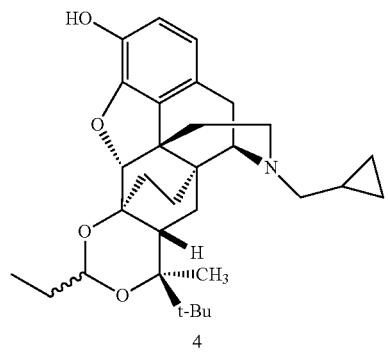

The title compound 4 was prepared similar to the procedure described in Example 1 for compound 3 using dipropyl sulfoxide instead of DMSO. After column chromatography, 117 mg (53.7% yield, >99.9 purity) of compound 4 was isolated as an off-white solid as a mixture of two epimers in a 96.1:3.9 ratio.

$^1$H NMR δ (300 MHz, CDCl$_3$): 6.68 (d, 1H), 6.50 (d, 1H), 4.91 (bs, 1H), 4.79 (t, 1H), 4.20 (d, 1H), 3.01-2.95 (m, 2H), 2.89-2.83 (m, 1H), 2.65-2.61 (m, 1H), 2.34-1.99 (m, 7H), 1.73-1.57 (m, 3H), 1.43-1.24 (m, 5H), 1.14-1.01 (m, 10H), 0.96-0.88 (m, 3H), 0.80-0.75 (m, 2H), 0.51-0.46 (m, 2H), 0.10-0.07 (m, 2H).

LC/MS (ESI), m/z=494.2 [M=H]$^+$ (Calc: 493.7).

Example 3

Preparation of (4bS,8R,8aS,9aR,10S,13aR,13bR)-10-tert-butyl-7-cyclopropylmethyl-5,6,7,8,9,9a,10,13b-octahydro-10-methyl-12-propyl-8a,13a-ethano-4,8-methanobenzofuro[3,2-e][1,3]dioxino[4,5-g]isoquinolin-1-ol (5)

Example 4

Preparation of (4bS,8R,8aS,9aR,10S,13aR,13bR)-10-tert-butyl-7-cyclopropylmethyl-5,6,7,8,9,9a,10,13b-octahydro-10-methyl-12-phenyl-8a,13a-ethano-4,8-methanobenzofuro[3,2-e][1,3]dioxino[4,5-g]isoquinolin-1-ol (6)

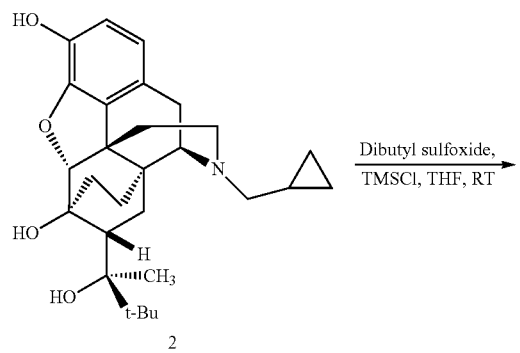

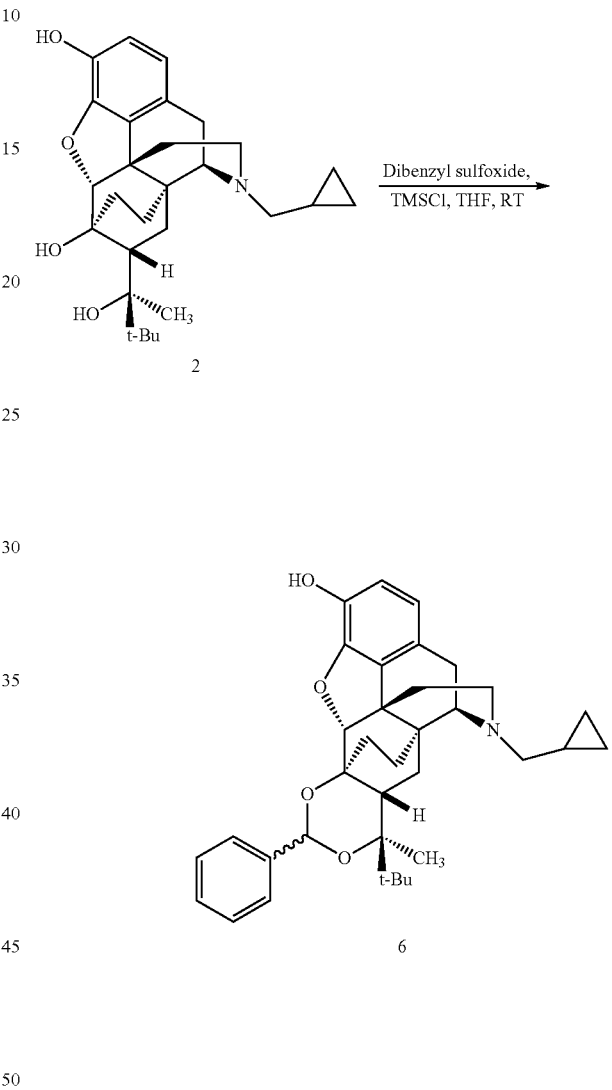

The title compound 5 was synthesized similar to the procedure described in Example 1 for compound 3 using dibutyl sulfoxide instead of DMSO. After column chromatography, 227 mg (86.3% yield, 99.4 purity) of compound 5 was isolated as an off-white solid as a mixture of two epimers in a 95.4:4.6 ratio.

$^1$H NMR δ (300 MHz, CDCl$_3$): 6.68 (d, 1H), 6.49 (d, 1H), 4.50 (bs, 1H), 4.86 (t, 1H), 4.20 (d, 1H), 3.00-2.95 (m, 2H), 2.88-2.79 (m, 1H), 2.69-2.59 (m, 1H), 2.34-1.95 (m, 7H), 1.72-1.68 (m, 1H), 1.58-1.52 (m, 2H), 1.47-1.24 (m, 6H), 1.13-0.98 (m, 11H), 0.92-0.87 (m, 3H), 0.79-0.75 (m, 2H), 0.50-0.45 (m, 2H), 0.11-0.09 (m, 2H).

LC/MS (ESI), m/z=508.3 [M=H]$^+$ (Calc: 507.7).

The title compound 6 was synthesized similar to the procedure described in Example 1 for compound 3 using dibenzyl sulfoxide instead of DMSO. After column chromatography, 197 mg (70.4% yield, >99.9 purity) of compound 6 was isolated as an off-white solid as a mixture of two epimers in a 90.8:9.2 ratio.

$^1$H NMR δ (300 MHz, CDCl$_3$): 7.50 (d, 1H), 7.48 (d, 1H), 7.37-7-26 (m, 3H), 6.69 (d, 1H), 6.51 (d, 1H), 5.82 (s, 1H), 4.90 (bs, 1H), 4.28 (d, 1H), 3.72-3.66 (m, 1H), 3-61-3.57 (m, 1H), 3.02-2.85 (m, 3H), 2.69-2.62 (m, 1H), 2.34-2.21 (m, 5H), 2.08-1.98 (m, 5H), 1.92-1.83 (m, 1H), 1.75-1.69 (m, 1H), 1.55 (s, 3H), 1.54-1.43 (m, 1H), 1.07 (s, 9H), 0.82-0.79 (m, 2H), 0.51-0.47 (m, 2H), 0.12-0.10 (m, 2H).

LC/MS (ESI), m/z=542.2 [M=H]$^+$ (Calc: 541.7).

Example 5

Preparation of (4bS,8R,8aS,9aR,10S,13aR,13bR)-1-benzyloxy-10-tert-butyl-7-cyclopropylmethyl-5,6,7,8,9,9a,10,13b-octahydro-10-methyl-8a,13a-ethano-4,8-methanobenzofuro[3,2-e][1,3]dioxino[4,5-g]isoquinoline (7)

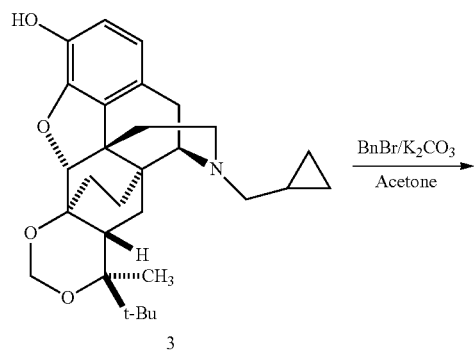

3

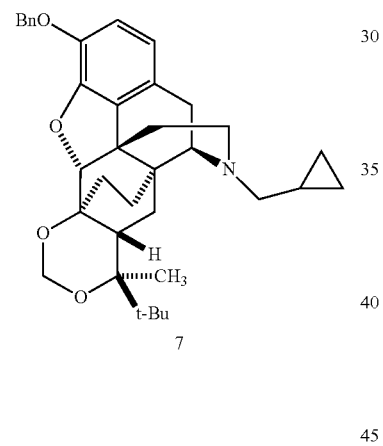

7

To a suspension of compound 3 (1.0 g, 2.15 mMol) and K$_2$CO$_3$ (0.88 g, 6.45 mMol) in acetone (10 ml) was added benzyl bromide (0.31 mL, 2.15 mMol). The resulting suspension was stirred at ambient temperature for 24 h. All volatiles were removed by vacuum distillation. The crude product was purified by column chromatography on silica to give 0.66 g of the title compound 7 (54.5% yield) in a purity of 96.9% as a white solid.

$^1$H NMR δ (300 MHz, CDCl$_3$): 7.45-7.42 (m, 2H), 7.35-7.26 (m, 3H), 6.71 (d, 1H), 6.48 (d, 1H), 5.25-5.13 (m, 2H), 5.02 (d, 1H), 4.78 (d, 1H), 4.23 (d, 1H), 2.97 (dd, 2H), 2.88-2.80 (m, 1H), 2.62 (dd, 1H), 2.36-1.96 (m, 7H), 1.69 (dd, 1H), 1.44 (s, 3H), 1.40-1.35 (m, 1H), 1.14-0.99 (m, 11H), 0.81-0.74 (m, 2H), 0.51-0.46 (m, 2H), 0.12-0.08 (m, 2H).

LC/MS (ESI), m/z=556.3 [M=H]$^+$ (Calc: 555.8).

Example 6

Preparation of (4bS,8R,8aS,9aR,10S,13aR,13bR)-10-tert-butyl-7-cyclopropylmethyl-5,6,7,8,9,9a,10,13b-octahydro-1-methoxy-10-methyl-8a,13a-ethano-4,8-methanobenzofuro[3,2-e][1,3]dioxino[4,5-g]isoquinoline (8)

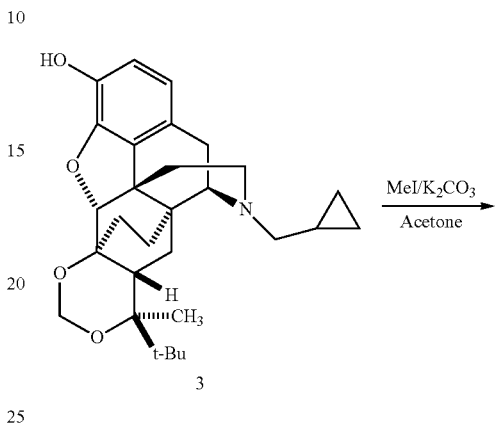

3

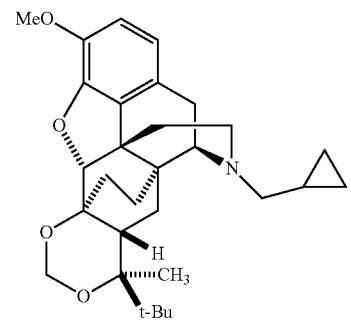

8

The title compound 8 was synthesized similar to the procedure described in Example 5 for compound 7 using methyl iodide instead of benzyl bromide. After column chromatography, 418 mg (49.4% yield) of compound 8 was isolated in a purity of 98.8% as an white solid.

$^1$H NMR δ (300 MHz, CDCl$_3$): 6.70 (d, 1H), 6.55 (d, 1H), 5.00 (d, 1H), 4.76 (d, 1H), 4.22 (d, 1H), 3.79 (s, 3H), 3.01 (d, 1H), 2.97 (d, 1H), 2.83 (dd, 1H), 2.63 (dd, 1H), 2.33-2.00 (m, 7H), 1.70 (dd, 1H), 1.44 (s, 3H), 1.40-1.35 (m, 1H), 1.14-1.02 (m, 11H), 0.81-0.77 (m, 2H), 0.51-0.46 (m, 2H), 0.11-0.09 (m, 2H).

LC/MS (ESI), m/z=480.2 [M=H]$^+$ (Calc: 479.7).

Example 7

Preparation of (4bS,8R,8aR,9aR,10S,13aR,13bR)-10-tert-butyl-7-cyclopropylmethyl-5,6,7,8,9,9a,10,13b-octahydro-10-methyl-8a,13a-etheno-4,8-methanobenzofuro[3,2-e][1,3]dioxino[4,5-g]isoquinolin-1-ol (11)

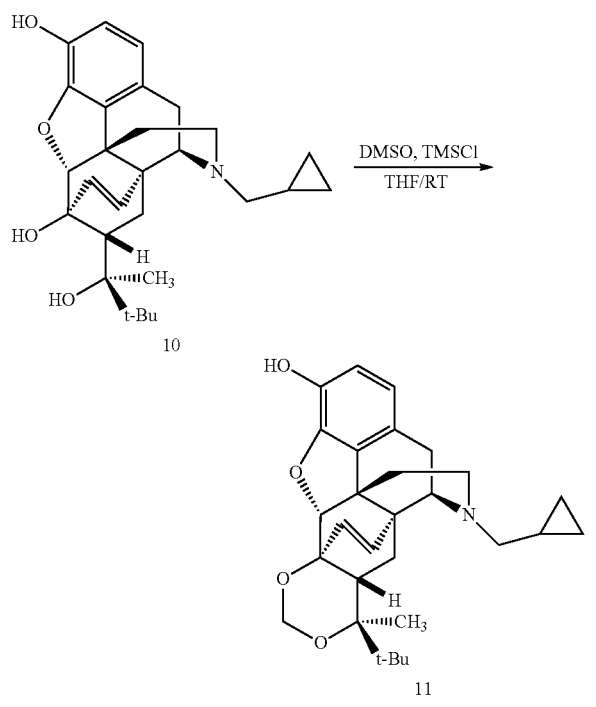

(a) The starting material, 17-cyclopropylmethyl-7α-[(2S)-3,3-dimethyl-2-hydroxybutan-2-yl]-4,5α-epoxy-3,6-dihydroxy-6α,14α-ethenomorphinan (10), was prepared as follows:

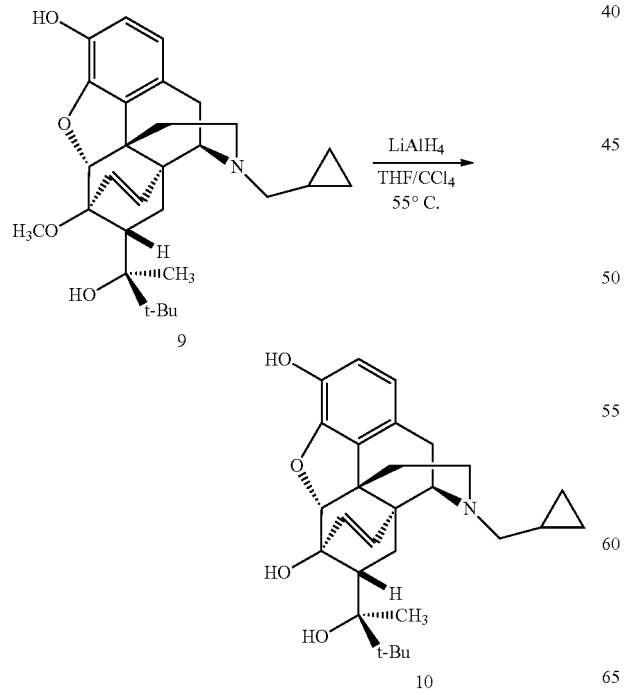

Compound 10 was synthesized similar to the procedure described in Example 1 for compound 2 using compound 9 (CAS#155203-05-7) (can be prepared as described in Schütz et al., *Heterocycles* 54:989-998 (2001)) rather than compound 1 (buprenorphine). After column chromatography, 2.6 g of compound 10 (89.7%) was obtained with a purity of >99%.

$^1$H NMR δ (300 MHz, CDCl$_3$): 6.76 (bs, 1H), 6.60 (d, 1H), 6.43 (d, 1H), 5.74 (d, 1H), 5.28 (d, 1H), 4.46 (bs, 1H), 4.34 (s, 1H), 3.47 (d, 1H), 3.06 (d, 1H), 2.93 (dd, 1H), 2.62 (dd, 1H), 2.42-2.25 (m, 4H), 2.16-2.10 (m, 1H), 1.85-1.68 (m, 2H), 1.72-1.68 (m, 1H), 1.13 (s, 3H), 1.01 (s, 9H), 0.99-0.94 (m, 1H), 0.83-0.81 (m, 1H), 0.54-0.48 (m, 2H), 0.15-0.13 (m, 2H).

LC/MS (ESI), m/z=452.2 [M=H]$^+$ (Calc: 451.6).

(b) The title compound 11 was synthesized similar to the procedure described in Example 1 for compound 3 using compound 10 rather than compound 2. After column chromatography, 1.36 g (50.9% yield) of compound 11 was isolated in a purity of >99% as a white solid.

$^1$H NMR δ (300 MHz, CDCl$_3$): 6.60 (d, 1H), 6.44 (d, 1H), 5.94 (d, 1H), 5.42 (d, 1H), 5.05 (d, 1H), 4.91 (d, 1H), 4.66 (bs, 1H), 4.39 (d, 1H), 3.48 (d, 1H), 3.09 (d, 1H), 2.95 (dd, 1H), 2.71 (dd, 1H), 2.43-2.37 (m, 4H), 2.18-2.12 (m, 1H), 2.04-1.87 (m, 2H), 1.13 (s, 3H), 0.99 (s, 9H), 0.91-0.81 (m, 2H), 0.55-0.49 (m, 21H), 0.17-0.13 (m, 2H).

LC/MS (ESI), m/z=464.2 [M=H]$^+$ (Calc: 463.6).

Example 8

Preparation of (4bS,8R,8aR,9a,10S,13aR,13bR)-10-tert-butyl-7-cyclopropylmethyl-5,6,7,8,9,9a,10,13b-octahydro-1-methoxy-10-methyl-8a,13a-etheno-4,8-methanobenzofuro[3,2-e][1,3]dioxino[4,5-g]isoquinoline (12)

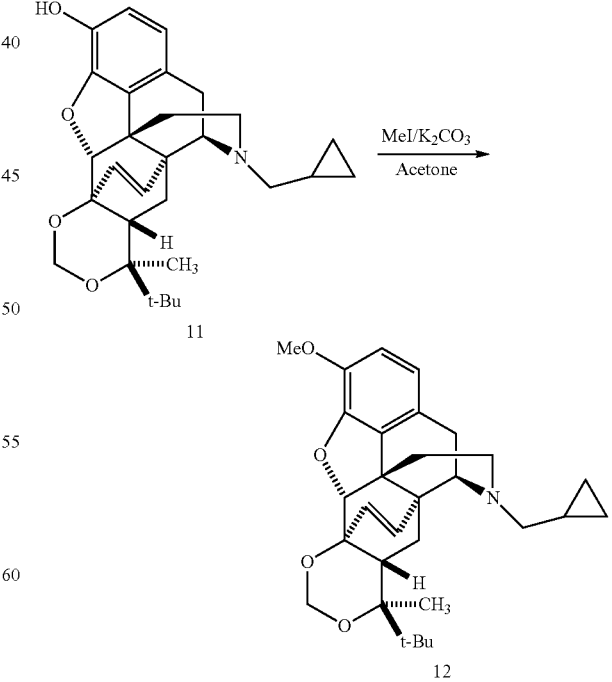

Compound 12 was synthesized similar to the procedure described in Example 5 for compound 7 using methyl iodide rather than benzyl bromide and compound 11 prepared in Example 7 rather than compound 3. After column chromatography, 360 mg (87.4% yield) of compound 12 was isolated in a purity of >99% as a white solid.

¹H NMR δ (300 MHz, CDCl₃): 6.60 (d, 1H), 6.48 (d, 1H), 5.98 (d, 1H), 5.42 (d, 1H), 5.02 (d, 1H), 4.89 (d, 1H), 4.37 (d, 1H), 3.79 (s, 3H), 3.48 (d, 1H), 3.10 (d, 1H), 2.93 (dd, 1H), 2.70 (dd, 1H), 2.43-2.30 (m, 4H), 2.14 (dd, 1H), 2.00-1.84 (m, 2H), 1.12 (s, 3H), 0.98 (s, 9H), 0.88-0.82 (m, 2H), 0.55-0.49 (m, 2H), 0.17-0.13 (m, 2H).

LC/MS (ESI), m/z=478.2 [M=H]⁺ (Calc: 477.6).

Example 9

Preparation of (4bS,8R,8aR,9aR,10S,13aR,13bR)-1-benzyloxy-10-tert-butyl-7-cyclopropylmethyl-5,6,7,8,9,9a,10,13b-octahydro-10-methyl-8a,13a-etheno-4,8-methanobenzofuro[3,2-e][1,3]dioxino[4,5-g]isoquinoline (13)

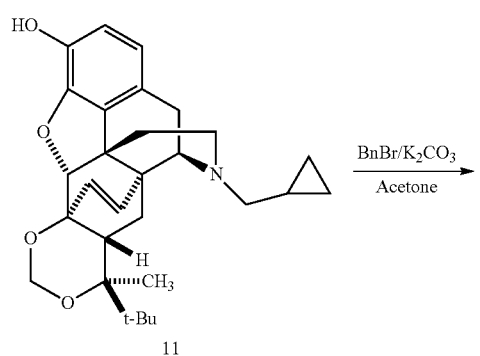

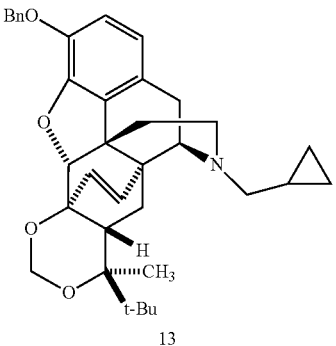

Compound 13 was synthesized similar to the procedure described in Example 5 for compound 7 using compound 11 prepared in Example 7 rather than compound 3. After column chromatography, 420 mg (87.7% yield) of compound 13 was isolated in a purity of >99% as a white solid.

¹H NMR δ (300 MHz, CDCl₃): 7.42-7.40 (m, 2H), 7.34-7.25 (m, 3H), 6.61 (d, 1H), 6.42 (d, 1H), 5.95 (d, 1H), 5.41 (d, 1H), 5.19-5.03 (m, 3H), 4.90 (d, 1H), 4.38 (s, 1H), 3.47 (d, 1H), 3.08 (d, 1H), 2.94 (dd, 1H), 2.69 (dd, 1H), 2.43-2.290 (m, 4H), 2.17-2.11 (m, 1H), 2.03-1.85 (m, 2H), 1.12 (s, 3H), 0.98 (s, 9H), 0.91-0.82 (m, 2H), 0.54-0.48 (m, 2H), 0.11-0.12 (m, 2H).

LC/MS (ESI), m/z=554.3 [M=H]⁺ (Calc: 553.7).

Example 10

Preparation of (4bS,8R,8aR,9aR,10S,13aR,13bR)-7-allyl-10-tert-butyl-5,6,7,8,9,9a,10,13b-octahydro-10-methyl-8a,13a-ethano-4,8-methanobenzofuro[3,2-e][1,3]dioxino[4,5-g]isoquinolin-1-ol (17)

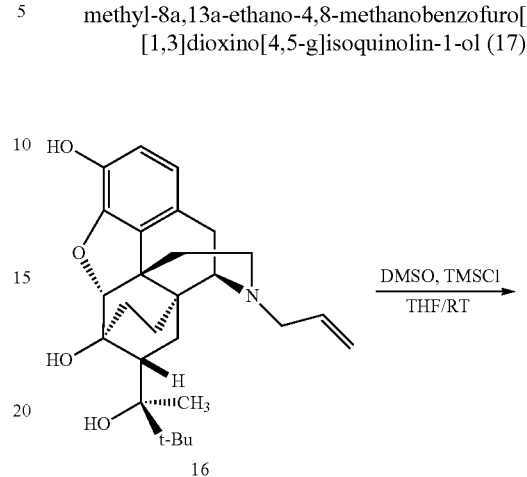

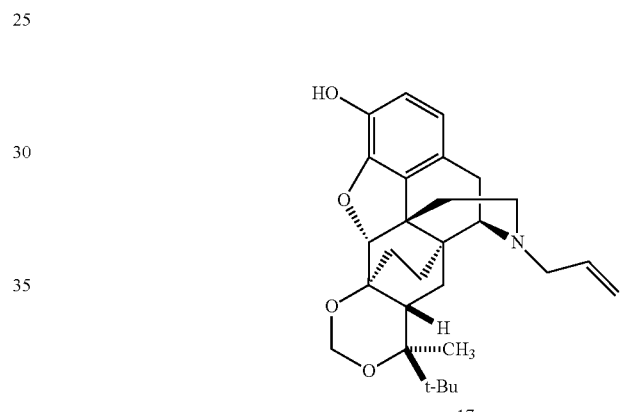

The starting material, 17-allyl-7α-[(2S)-3,3-dimethyl-2-hydroxybutan-2-yl]-4,5α-epoxy-3,6-dihydroxy-6α,14α-ethanomorphinan (16), was prepared in two steps starting from norbuprenorphine as follows:

(a) Synthesis of 17-allyl-7α-[(2S)-3,3-dimethyl-2-hydroxybutan-2-yl]-4,5α-epoxy-3-hydroxy-6-methoxy-6α,14α-ethanomorphinan (15):

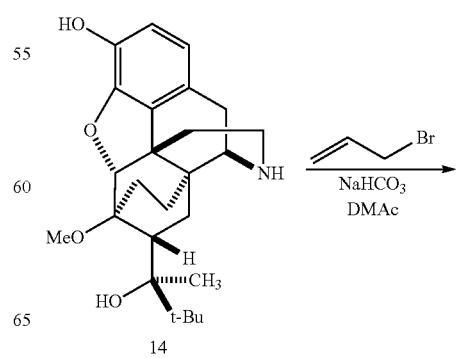

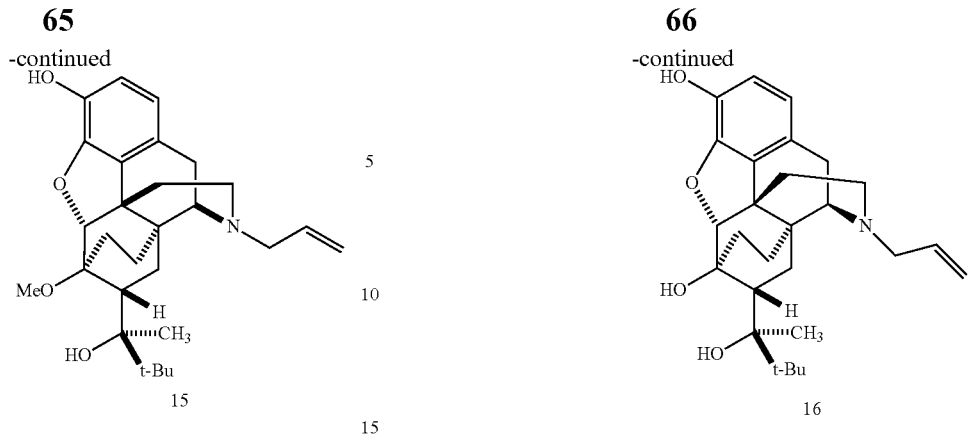

To a mixture of norbuprenorphine (14) (5.6 g, 13.5 mMol) and NaHCO₃ (3.4 g, 40.6 mMol) in DMAc (60 ml) was added dropwise at ambient temperature allyl bromide (1.4 ml, 16.3 mMol). The progress of the N-allylation was monitored by HPLC. After 5 h stirring at 60° C., the reaction was complete. The reaction mixture was added into water (100 ml). The pH of the resultant white suspension was adjusted to 9.0 with aqueous NH₄OH (5 ml, 29 wt %). After aging at ambient temperature for 2 h, the suspension was filtered. The wet cake was washed with water (2×10 ml), dried in an oven at 50° C. under vacuum with N₂-bleed to afford 5.97 g of compound 15 (Marton, J., et al., supra) (97.2% yield) as an off-white solid with a purity of 96.5%.

¹H NMR δ (300 MHz, CDCl₃): 6.69 (d, 1H), 6.52 (d, 1H), 5.85 (s, 1H), 5.82-5.70 (m, 1H), 5.20 (dd, 1H), 5.10 (dd, 1H), 4.68 (bs, 1H), 4.46 (d, 1H), 3.53 (s, 3H), 3.07-2.99 (m, 3H), 2.86-2.80 (m, 1H), 2.77 (d, 1H), 2.53 (dd, 1H), 2.33 (dt, 1H), 2.26-2.11 (m, 1H), 2.04-1.92 (m 1H), 1.84-1.66 (m, 3H), 1.35 (s, 3H), 1.34-1.26 (m, 1H), 1.08-1.05 (m, 1H), 1.03 (s, 9H), 0.74-0.62 (m, 1H).

LC/MS (ESI), m/z=454.2 [M=H]⁺ (Calc: 453.3).

Norbuprenorphine (14) (CAS#78715-23-8) can be prepared as described in the literature, for example, in WO 2007/081506 or Machara, A., et al., supra.

(b) Synthesis of 17-allyl-7α-[(2S)-3,3-dimethyl-2-hydroxybutan-2-yl]-4,5α-epoxy-3,6-dihydroxy-6α,14α-ethanomorphinan (16):

Compound 16 was synthesized similar to the procedure described in Example 1 for the preparation of compound 2 using compound 15 rather than compound 1. After column chromatography, 4.0 g of compound 16 (75.8%) was obtained with a purity of 98.5%.

¹H NMR δ (300 MHz, CDCl₃): 6.75 (d, 1H), 6.48 (d, 1H), 5.82-5.68 (m, 1H), 5.16 (dd, 1H), 5.08 (dd, 1H), 4.13-4.09 (m, 1H), 3.02-2.92 (m, 3H), 2.77-2.70 (m, 2H), 2.39 (dd, 1H), 2.21-2.05 (m, 2H), 1.92-1.84 (m, 1H), 1.81-1.72 (m, 1H), 1.58-1.46 (m, 1H), 1.41 (s, 3H), 1.28-1.16 (m, 3H), 1.01 (s, 9H), 0.98-0.91 (m, 1H), 0.63-0.54 (m, 1H).

LC/MS (ESI), m/z=440.1 [M=H]⁺ (Calc: 439.2).

(c) The title compound 17 was synthesized similar to the procedure described in Example 1 for preparing compound 3 using compound 16 rather than compound 2. After column chromatography, 1.29 g (49.0% yield) of compound 17 was isolated in a purity of >99% as a-white solid.

¹H NMR δ (300 MHz, CDCl₃): 6.71 (d, 1H), 6.53 (d, 1H), 5.82-5.73 (m, 1H), 5.18 (dd, 1H), 5.10 (dd, 1H), 5.03 (d, 1H), 4.77 (d, 1H), 4.25 (d, 1H), 3.07-3.00 (m, 3H), 2.88-2.82 (m, 1H), 2.78-2.77 (m, 1H), 2.54 (dd, 1H), 2.39-2.34 (dd, 1H), 2.31-2.28 (m, 2H), 2.24-1.95 (m, 4H), 1.73 (dd, 1H), 1.43 (s, 3H), 1.39-1.35 (m, 1H), 1.15-1.04 (m, 1H), 1.02 (s, 9H), 0.81-0.70 (m, 1H).

LC/MS (ESI), m/z=452.1 [M=H]⁺ (Calc: 451.2).

Example 11

Preparation of (4bS,8R,8aR,9aR,10S,13aR,13bR)-7-allyl-10-tert-butyl-5,6,7,8,9,9a,10,13b-octahydro-1-methoxy-10-methyl-8a,13a-ethano-4,8-methanobenzofuro[3,2-e][1,3]dioxino[4,5-g]isoquinoline (18)

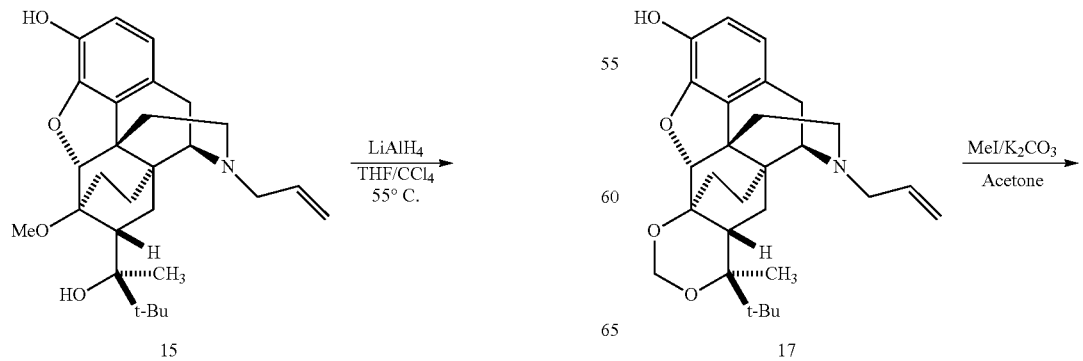

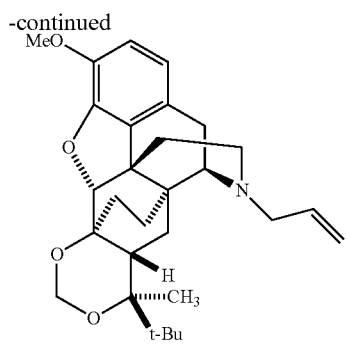

18

The title compound 18 was synthesized similar to the procedure described in Example 5 for preparing compound 7 using methyl iodide rather than benzyl bromide and compound 17 rather than compound 3. After column chromatography, 300 mg (58% yield) of compound 18 was isolated in a purity of >99% as a white solid.

$^1$H NMR δ (300 MHz, CDCl$_3$): 6.70 (d, 1H), 6.56 (d, 1H), 5.83-5.71 (m, 1H), 5.18 (dd, 1H), 5.09 (dd, 1H), 5.00 (d, 1H), 4.75 (d, 1H), 4.22 (d, 1H), 3.85 (s, 3H), 3.07-3.01 (m, 3H), 2.86-2.81 (m, 1H), 2.77 (d, 1H), 2.54 (dd, 1H), 2.28-1.94 (m, 5H), 1.71 (dd, 1H), 1.43 (s, 3H), 1.41-1.32 (m, 1H), 1.14-1.05 (m, 2H), 1.02 (s, 9H), 0.82-0.71 (m, 1H).

LC/MS (ESI), m/z=466.1 [M=H]$^+$ (Calc: 465.3).

Example 12

Preparation of (4bS,8R,8aR,9aR,10S,13aR,13bR)-7-allyl-1-benzyloxy-10-tert-butyl-5,6,7,8,9,9a,10,13b-octahydro-10-methyl-8a,13a-ethano-4,8-methanobenzofuro[3,2-e][1,3]dioxino[4,5-g]isoquinoline (19)

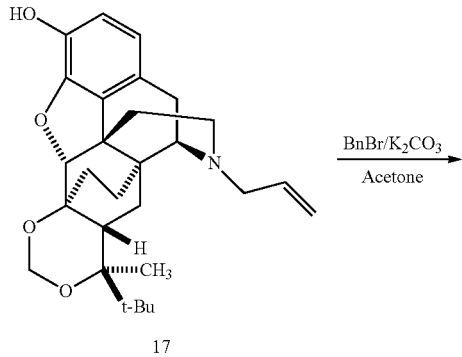

The title compound 19 was synthesized similar to the procedure described in Example 5 for preparing compound 7 using compound 17 rather than 3. After column chromatography, 590 mg (98% yield) of compound 19 was isolated in a purity of 97.7% as a white solid.

$^1$H NMR δ (300 MHz, CDCl$_3$): 7.45-7.42 (m, 2H), 7.35-7.28 (m, 3H), 6.72 (d, 1H), 6.49 (d, 1H), 5.78-5.72 (m, 1H), 5.25-5.07 (m, 4H), 5.01 (d, 1H), 4.77 (d, 1H), 4.22 (d, 1H), 3.06-2.99 (m, 3H), 2.93 (dd, 1H), 2.76 (d, 1H), 2.35-1.96 (m, 5H), 1.71 (dd, 1H), 1.56 (bs, 2H), 1.43 (s, 3H), 4.41-1.32 (m, 1H), 1.13-1.05 (m, 1H), 1.02 (s, 9H), 0.80-0.74 (m. 1H).

LC/MS (ESI), m/z=542.2 [M=H]$^+$ (Calc: 541.3).

Example 13

Preparation of (4bS,8R,8aR,9aR,10S,13aR,13bR)-10-tert-butyl-5,6,7,8,9,9a,10,13b-octahydro-7,10-dimethyl-8a,13a-ethano-4,8-methanobenzofuro[3,2-e][,3]dioxino[4,5-g]isoquinolin-1-ol (22)

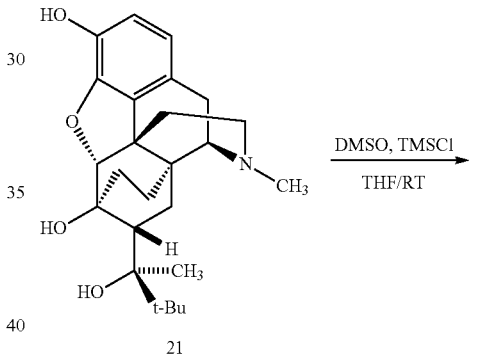

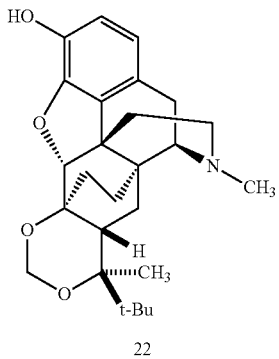

22

The starting material, 7α-[(2S)-3,3-dimethyl-2-hydroxybutan-2-yl]-4,5α-epoxy-3,6-dihydroxy-7-methyl-6α,14α-ethanomorphinan (21), was prepared in two steps starting from norbuprenorphine (14) as follows:

(a) Synthesis of 17-allyl-7α-[(2S)-3,3-dimethyl-2-hydroxybutan-2-yl]-4,5α-epoxy-3-hydroxy-6-methoxy-6α,14α-ethanomorphinan (CAS#228550-34-3) (20):

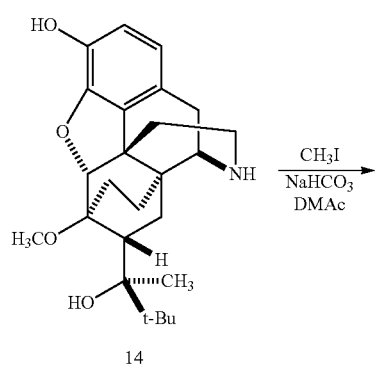

14

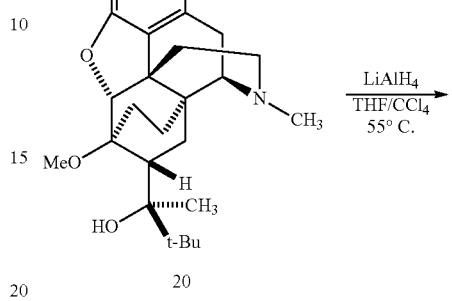

20

(b) Synthesis of 7α-[(2S)-3,3-dimethyl-2-hydroxybutan-2-yl]-4,5α-epoxy-3,6-dihydroxy-17-methyl-6α,14α-ethanomorphinan (21):

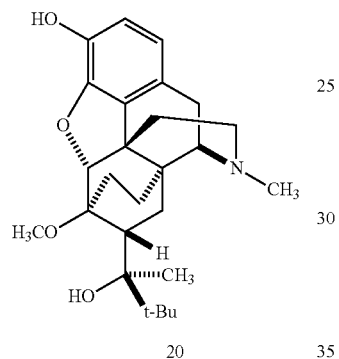

20

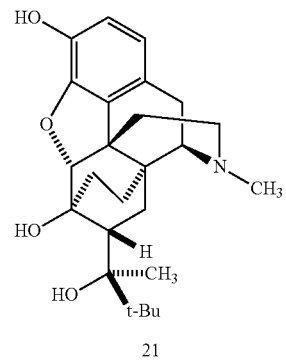

21

To a solution of norbuprenorphine (14) (5.6 g, 13.5 mMol) in DMAc (60 ml) was added NaHCO₃ (3.4 g, 40.6 mMol) followed by methyl iodide (0.93 ml, 14.85 mMol) at ambient temperature. The progress of the N-methylation was monitored by HPLC. After 24 h stirring, the starting material was consumed and the reaction was deemed completed. The reaction mixture was added into water (100 ml) and the pH of the resultant white suspension was adjusted to 9.0 with aqueous NH₄OH (5 ml, 29 wt %). After aging at ambient temperature for 2 h, the suspension was filtered. The wet cake was washed with water (2×10 ml), dried in an oven at 50° C. under vacuum with a N₂-bleed to afford 5.21 g of compound 20 ((Husbands, S. M., et al., supra) (90.0% yield) as an off-white solid with a purity of 98.9%. A sample (500 mg) was further purified by column chromatography to afford 374 mg (74% yield) of compound 20 as a white solid in a purity of >99%.

¹H NMR δ (300 MHz, CDCl₃): 6.69 (d, 1H), 6.53 (d, 1H), 5.89 (s, 1H), 4.45 (d, 1H), 3.53 (s, 3H), 3.10 (d, 1H), 2.81-2.75 (m, 1H), 2.64 (d, 1H), 2.43 (dd, 1H), 2.33-2.15 (m, 6H), 2.05-1.94 (m, 1H), 1.85-1.22 (m 4H), 1.35 (s, 3H), 1.32-1.26 (m, 1H), 1.17-1.05 (m, 1H), 1.02 (s, 9H), 0.77-0.68 (m, 1H).

LC/MS (ESI), m/z=428.2 [M=H]⁺ (Calc: 427.3).

Compound 21 was synthesized similar to the procedure described in Example 1 for the preparation of compound 2 using compound 20 rather than compound 1. After isolation, 3.76 g of compound 21 (82.5%) was obtained with a purity of 92.7% as an off-white solid A sample was further purified by column chromatography to afford compound 21 in >99% purity as a white solid.

¹H NMR δ (300 MHz, CDCl₃): 6.72 (d, 1H), 6.46 (d, 1H), 5.48 (bs, 1H), 4.11 (s, 1H), 3.04 (d, 1H), 2.75-2.70 (m, 1H), 2.61-2.59 (m, 1H), 2.38-2.31 (m, 1H), 2.26 (s, 6H), 2.19-1.79 (m, 6H), 1.49-1.43 (m, 1H), 1.41 (s, 3H), 1.32-1.24 (m, 2H), 1.01 (s, 9H), 0.98-0.91 (m, 1H), 0.63-0.54 (m, 1H).

LC/MS (ESI), m/z=414.2 [M=H]⁺ (Calc: 413.3).

(c) The title compound 22 was synthesized similar to the procedure described in Example 1 for preparing compound 3 using compound 21 rather than compound 2. After column chromatography purification, 0.45 g (14.4% yield) of compound 21 was isolated in a purity of 98.3% as a-white solid.

¹H NMR δ (300 MHz, CDCl₃): 6.71 (d, 1H), 6.54 (d, 1H), 5.02 (d, 1H), 4.77 (d, 1H), 4.24 (d, 1H), 3.10 (d, 1H), 2.82-2.72 (m, 1H), 2.65 (d, 1H), 2.44 (dd, 1H), 2.35-2.30 (m, 1H), 2.29 (s, 3H), 2.27-1.86 (m, 4H), 1.72 (dd, 1H), 1.43 (s, 3H), 1.36-1.26 (m, 2H), 1.17-1.1.06 (m, 2H), 1.01 (s, 9H), 0.84-0.70 (m, 1H).

LC/MS (ESI), m/z=425.9 [M=H]⁺ (Calc: 425.3).

Example 14

Preparation of (4bS,8R,8aR,9aR,10S,13aR,13bR)-10-tert-butyl-5,6,7,8,9,9a,10,13b-octahydro-1-methoxy-7,10-dimethyl-8a,13a-ethano-4,8-methanobenzofuro[3,2-e][1,3]dioxino[4,5-g]isoquinoline (23)

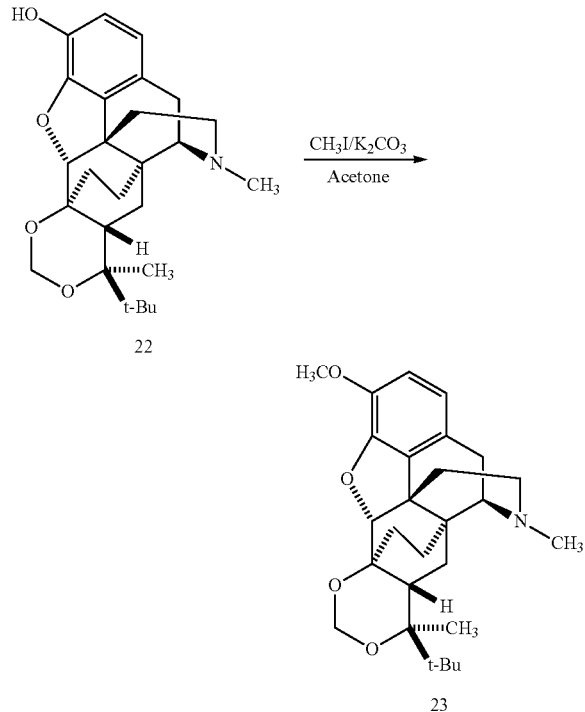

The title compound 23 was synthesized similar to the procedure described in Example 5 for preparing compound 7 using methyl iodide rather than benzyl bromide and compound 22 rather than compound 3. After column chromatography, 168 mg (81.3% yield) of compound 23 was isolated in a purity of >99% as a white solid.

$^1$H NMR δ (300 MHz, CDCl$_3$): 6.70 (d, 1H), 6.56 (d, 1H), 5.01 (d, 1H), 4.75 (d, 1H), 4.20 (d, 1H), 3.85 (s, 3H), 3.12 (d, 1H), 2.80-2.71 (m, 1H), 2.64 (d, 1H), 2.41 (dd, 1H), 2.35-1.95 (m, 8H), 1.70 (dd, 1H), 1.43 (s, 3H), 1.41-1.32 (m, 1H), 1.16-1.06 (m, 2H), 1.02 (s, 9H), 0.82-0.71 (m, 1H).
LC/MS (ESI), m/z=440.0 [M=H]$^+$ (Calc: 439.3).

Example 15

Preparation of (4bS,8R,8aR,9aR,10S,13aR,13bR)-1-benzyloxy-10-tert-butyl-5,6,7,8,9,9a,10,13b-octahydro-7,10-dimethyl-8a,13a-ethano-4,8-methanobenzofuro[3,2-e][1,3]dioxino[4,5-g]isoquinoline (24)

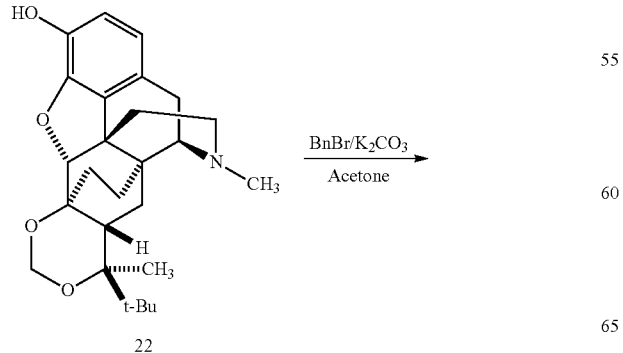

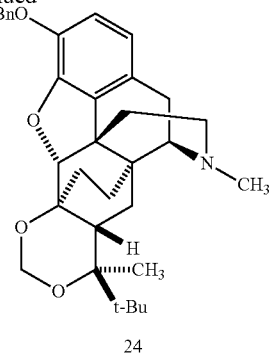

The title compound 24 was synthesized similar to the procedure described in Example 5 for preparing compound 7 using compound 22 rather than 3. After column chromatography, 590 mg (98% yield) of compound 24 was isolated in a purity of 97.7% as a white solid.

$^1$H NMR δ (300 MHz, CDCl$_3$): 7.45-7.42 (m, 2H), 7.35-7.28 (m, 3H), 6.72 (d, 1H), 6.49 (d, 1H), 5.78-5.72 (m, 1H), 5.25-5.07 (m, 4H), 5.01 (d, 1H), 4.77 (d, 1H), 4.22 (d, 1H), 3.06-2.99 (m, 3H), 2.93 (dd, 1H), 2.76 (d, 1H), 2.35-1.96 (m, 5H), 1.71 (dd, 1H), 1.56 (bs, 2H), 1.43 (s, 3H), 4.41-1.32 (m, 1H), 1.13-1.05 (m, 1H), 1.02 (s, 9H), 0.80-0.74 (m, 1H).
LC/MS (ESI), m/z=542.2 [M=H]$^+$ (Calc: 541.3).

Example 16

Preparation of (4bS,8R,8aR,9aR,10R,13aR,13bR)-10-benzyl-1-benzyloxy-5,6,7,8,9,9a,10,13b-octahydro-7,10-dimethyl-8a,13a-etheno-4,8-methanobenzofuro[3,2-e][,3]dioxino[4,5-J]isoquinoline (29)

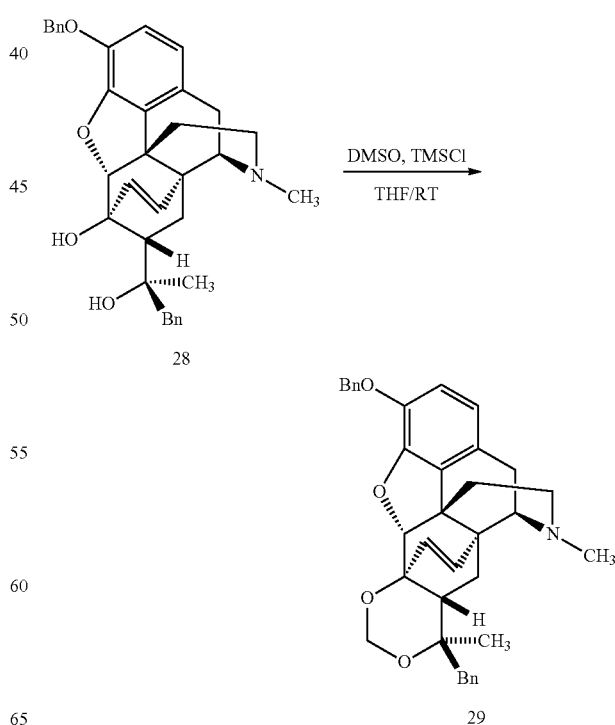

The starting material, (R)-2-(1-benzyloxy-17-methyl-4,5α-epoxy-6-hydroxy-6α,14α-ethenomorphinan-7α-yl)-1-phenylpropan-2-ol (27), was prepared in two steps starting from 3-benzyloxy-4,5α-epoxy-7α-(ethanon-2-yl)-6-methoxy-17-methyl-6α,14α-ethenomorphinan (25) (CAS#1020267-11-1) as follows:

(a) Synthesis of (R)-2-[3-benzyloxy-4,5α-epoxy-6-hydroxy-17-methyl-6α,14α-ethenomorphinan-7α-yl]-1-phenylpropan-2-ol (26) and (S)-2-[3-benzyloxy-4,5α-epoxy-6-hydroxy-17-methyl-6α,14α-ethenomorphinan-7α-yl]-1-phenylpropan-2-ol (27):

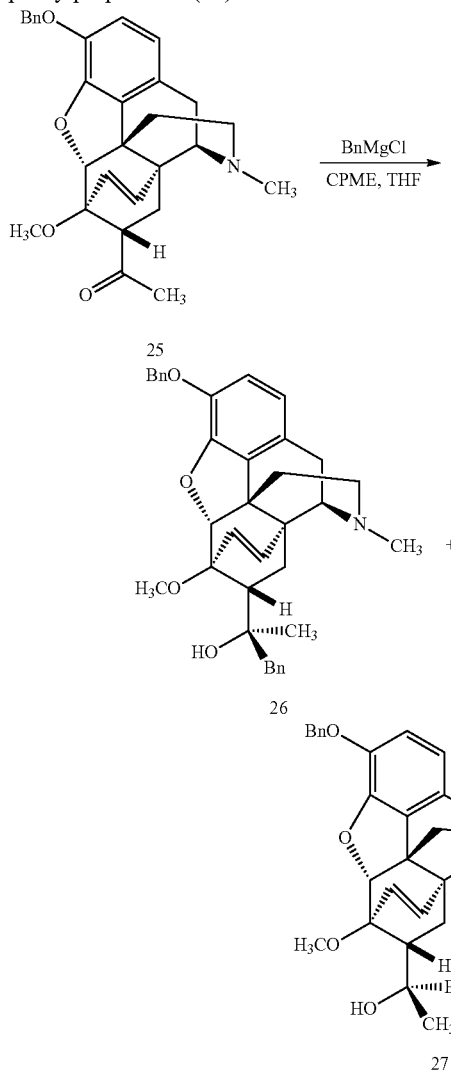

To a mixture of cyclopentyl methyl ether (CPME) 187 mL) and benzyl magnesium, chloride (393 mL, 1.0 M, 0.39 mol) in diethyl ether was added THF (51 mL) and the resulting mixture was stirred at ambient temperature. After 1 hour, a precipitate formed and the mixture was cooled to about 0° C. and a solution of compound 25 (60.0 g, 0.13 ml) in CPME (100 mL) was added in three portions with about 30 minutes reaction time between additions. The progress of the reaction was monitored by HPLC. After the third addition, compound 25 was consumed and the reaction was deemed completed.

The reaction mixture was poured at 0° C. into a mixture of water (375 mL) and saturated NH$_4$Cl solution and the layers were separated. The aqueous layer was extracted with CPME (750 mL). The combined organic layers were concentrated to afford the crude reaction product as an amber oil. After purification by column chromatography on silica gel, eluting with ethyl acetate/hexane, and after removal of the eluent under vacuum, 35.0 g (48.6% yield) of crude compound 26 (R$_f$=0.5; 30% ethyl aceate/hexane) and 24.1 g (33.5 yield) of crude compound 27 (R$_f$=0.2; 30% ethyl aceate/hexane) was obtained.

Crude compound 26 was purified by recrystallization from ethanol (1.2 L) to afford 18.5 g of compound 26 as a white solid with a purity of >99%. $^1$H NMR δ (400 MHz, CDCl$_3$): 7.39-7.20 (m, 10H), 6.65 (d, 1H), 6.47 (d, 1H), 5.97 (d, 1H), 5.47 (d, 1H), 5.14 (s, 1H), 5.10-5.05 (m, 2H), 4.53 (d, 1H). 3.71 (s, 3H), 3.22 (d, 1H), 3.17 (d, 1H), 3.00 (dd, 1H), 2.70 (d, 1H), 2.60 (dd, 1H), 2.51 (d, 1H), 2.39-2.34 (m, 5H), 1.99-1.96 (m, 1H), 1.93-1.89 (m, 1H), 1.82-1.79 (m, 1H), 0.98-0.93 (m, 4H). LC/MS (ESI), m/z=550.2 [M=H]$^+$ (Calc: 549.3). The stereochemistry of compound 26 was also confirmed by X-ray analysis.

Crude compound 27 (7.5 g) was purified by recrystallization from ethanol (0.25 L) to afford 3.8 of compound 27 as a white solid with a purity of >99%. $^1$H NMR δ (400 MHz, CDCl$_3$): 7.41-7.15 (m, 10H), 6.67 (d, 1H), 6.49 (d, 1H), 6.03 (d, 1H), 5.50 (d, 1H), 5.15 (d, 1H), 5.09 (d, 1H), 4.75 (s, 1H), 4.61 (d, 1H). 3.83 (s, 3H), 3.23 (d, 1H), 3.19 (dd, 1H), 2.94 (dd, 1H), 2.68 (d, 1H), 2.52 (dd, 1H), 2.49-2.37 (m, 6H), 2.14-2.12 (m, 1H), 2.04-1.97 (m, 1H), 1.86 (dd, 1H), 1.00 (dd, 1H), 0.83 (s, 3H). LC/MS (ESI), m/z=550.2 [M=H]$^+$ (Calc: 549.3). The stereochemistry of compound 27 was also confirmed by X-ray analysis.

3-Benzyloxy-4,5α-epoxy-7α-(ethanon-2-yl)-6-methoxy-17-methyl-6α,14α-ethenomorphinan (25) (CAS#1020267-11-1) can be prepared as described in the literature, for example, in CZ 300995 B6 or WO 2008/048957.

(b) Synthesis of (R)-2-(1-benzyloxy-17-methyl-4,5α-epoxy-6-hydroxy-6α,14α-ethenomorphinan-7α-yl)-1-phenylpropan-2-ol (28):

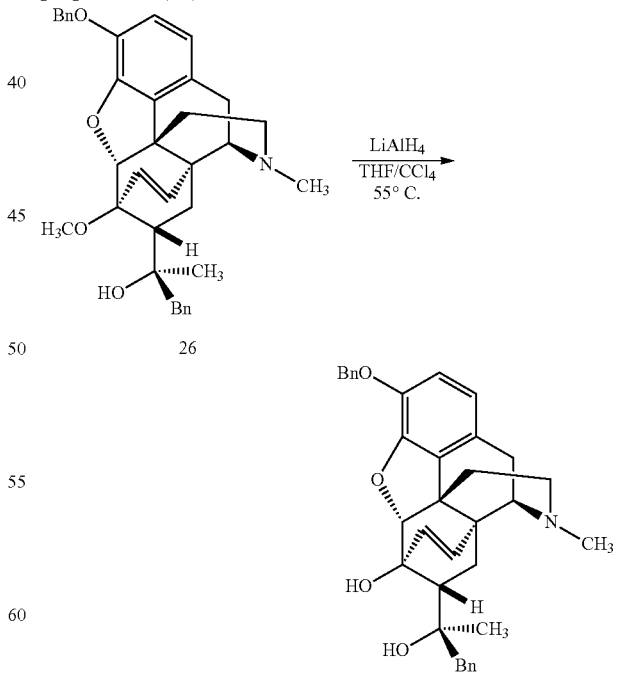

Compound 28 was synthesized similar to the procedure described in Example 1 for the preparation of compound 2 using compound 26 rather than compound 1. After isolation, 4.2 g of compound 28 (97.9%) was obtained with a purity of >99%.

¹H NMR δ (300 MHz, CDCl₃): 7.42-7.24 (m, 10H), 6.64 (d, 1H), 6.48 (d, 1H), 5.66 (d, 1H), 5.32 (d, 1H), 5.15 (d, 1H), 5.07 (d, 1H), 4.30 (d, 1H), 4.11 (bs, 1H), 3.16 (bs, 1H), 3.25-3.17 (m, 2H), 2.98 (dd, 1H), 2.76-2.63 (m, 2H), 2.54-2.50 (m, 1H), 2.44-2.34 (m, 5H), 2.00-1.83 (m, 3H), 1.03 (s, 3H), 0.99-0.93 (m, 1H).

LC/MS (ESI), m/z=536.3 [M=H]⁺ (Calc: 535.3).

(c) The title compound 29 was synthesized similar to the procedure described in Example 1 for preparing compound 3 using compound 28 rather than compound 2. After column chromatography, 0.92 g (23.5% yield) of compound 29 was isolated in a purity of 94.6% as a-white solid.

¹H NMR δ (300 MHz, CDCl₃): 7.45-7.38 (m, 2H), 7.34-7.22 (m, 8H), 6.61 (d, 1H), 6.45 (d, 1H), 5.95 (d, 1H), 5.44 (d, 1H), 5.15 (d, 1H), 5.06 (d, 1H), 5.01 (d, 1H), 4.92 (d, 1H), 4.31 (d, 1H), 3.25-3.17 (m, 2H), 2.91 (dd, 1H), 2.79-2.2.68 (m, 2H), 2.55-2.51 (m, 1H), 2.44-2.34 (m, 5H), 2.00-1.83 (m, 3H), 1.03 (s, 3H), 1.01-0.94 (m, 1H).

LC/MS (ESI), m/z=548.3 [M=H]⁺ (Calc: 547.3).

Example 17

Preparation of (4bS,8R,8aR,9aR,10S,13aR,13bR)-10-benzyl-1-benzyloxy-5,6,7,8,9,9a,10,13b-octahydro-7,10-dimethyl-8a,13a-etheno-4,8-methanobenzofuro[3,2-e][1,3]dioxino[4,5-g]isoquinoline (31)

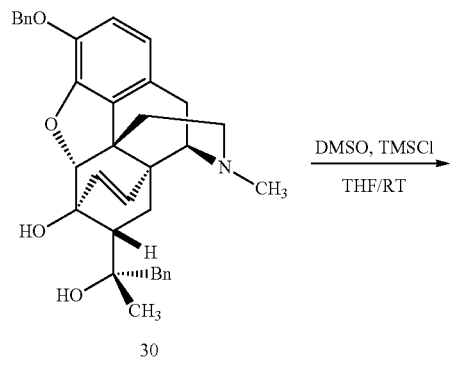

The title compound 31 can be synthesized similar to the procedure described in Example 16 for preparing compound 29 using (S)-2-(1-benzyloxy-17-methyl-4,5α-epoxy-6-hydroxy-6α,14α-ethenomorphinan-7α-yl)-1-phenylpropan-2-ol (30) rather than compound 28.

Compound 30 can be synthesized similar to the procedure described in Example 16 for the preparation of compound 28 using compound 27 rather than compound 26.

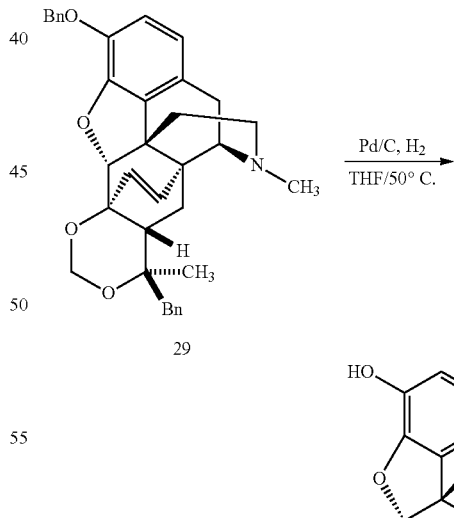

Example 18

Preparation of (4bS,8R,8aR,9aR,10R,13aR,13bR)-10-benzyl-5,6,7,8,9,9a,10,13b-octahydro-7,10-dimethyl-8a,13a-ethano-4,8-methanobenzofuro[3,2-e][1,3]dioxino[4,5-g]isoquinolin-1ol (32)

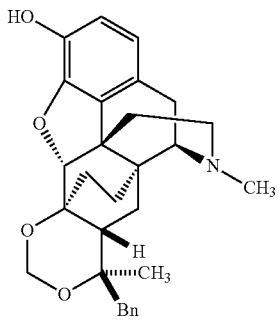

A mixture of compound 29 (500 mg, 1.08 mmol) in THF (5 mL) was hydrogenated at 50° C. on 10% Pd/C (250 mg). The reaction progress was monitored by HPLC and all starting material 29 was consumed after 24 h. The catalyst was removed by filtration. The filtrate was concentrated to residue to afford 0.38 g of crude compound 32. The crude product was purified by column chromatography (hexane/acetone 2:1) to give 0.16 g of the title compound 32 (38.1% yield) in a purity of 95.0%.

$^1$H NMR δ (300 MHz, CDCl$_3$): 7.30-7.26 (m, 5H), 6.71 (d, 1H), 6.55 (d, 1H), 4.99 (d, 1H), 4.79 (d, 1H), 4.17 (d, 1H), 3.13 (d, 1H), 2.88-2.71 (m, 4H), 2.48 (dd, 1H), 2.36-2.22 (m, 5H), 2.17-1.84 (m, 4H), 1.69 (dd, 1H), 1.42-1.32 (m, 4H), 1.25-1.07 (m, 3H), 0.90-0.78 (m, 1H).

LC/MS (ESI), m/z=460.12 [M=H]$^+$ (Calc: 459.6).

Example 19

Preparation of (4bS,8R,8aR,9aR,10S,13aR,13bR)-10-benzyl-5,6,7,8,9,9a,10,13b-octahydro-7,10-dimethyl-8a,13a-ethano-4,8-methanobenzofuro[3,2-e][1,3]dioxino[4,5-g]isoquinolin-1ol (33)

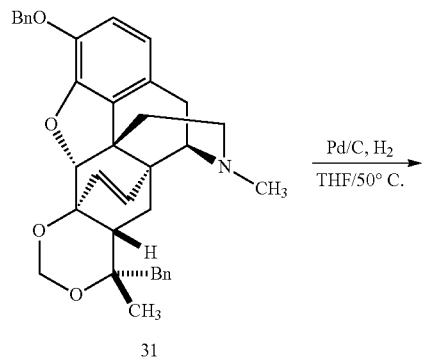

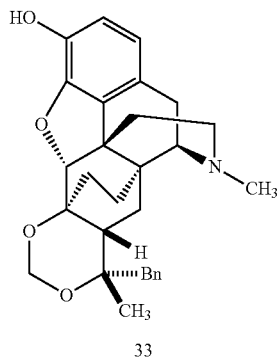

The title compound 33 can be synthesized similar to the procedure described in Example 18 for preparing compound 32 using compound 31 rather than compound 29.

Example 20

The following Table provides results on the efficacy of binding and activity response of representative Compounds of the Invention at the μ- and κ-opioid receptors. The binding affinity (represented as K$_i$ values) and activity response in functional assays (represented as EC$_{50}$ and E$_{max}$ values) were determined as described above. The corresponding values are also provided for buprenorphine for reference.

TABLE 1

| Compound | Structure | μ-opioid receptor | | | κ-opioid receptor | | |
|---|---|---|---|---|---|---|---|
| | | K$_i$ (nM) | EC$_{50}$ (nM) | E$_{max}$ (%) | K$_i$ (nM) | EC$_{50}$ (nM) | E$_{max}$ (%) |
| Buprenorphine: | 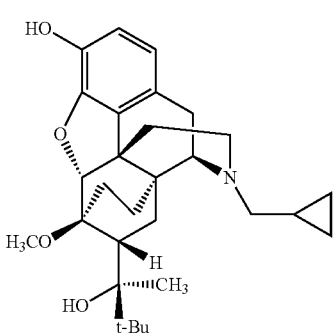 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5] | 0.30 | 0.45 | 11.00 | 0.04 | 0.56 | 11.00 |

TABLE 1-continued

| Compound | Structure | μ-opioid receptor | | | κ-opioid receptor | | |
|---|---|---|---|---|---|---|---|
| | | $K_i$ (nM) | $EC_{50}$ (nM) | $E_{max}$ (%) | $K_i$ (nM) | $EC_{50}$ (nM) | $E_{max}$ (%) |
| 3 | | 0.45 | 0.86 | 46.67 | 0.12 | 22.66 | 16.67 |
| 4 | | 0.35 | 1.40 | 59.67 | 0.19 | 4.42 | 16.00 |
| 5 | | 0.54 | 3.54 | 50.67 | 0.72 | 9.48 | 13.67 |
| 6 | | 2.26 | 5.35 | 33.33 | 4.61 | >20 | 0.33 |

TABLE 1-continued

| Compound | Structure | μ-opioid receptor | | | κ-opioid receptor | | |
|---|---|---|---|---|---|---|---|
| | | $K_i$ (nM) | $EC_{50}$ (nM) | $E_{max}$ (%) | $K_i$ (nM) | $EC_{50}$ (nM) | $E_{max}$ (%) |
| 11 | HO-... t-Bu | ND | 1.56 | 46 | 0.44 | 7.76 | 25 |
| 12 | H₃CO-... t-Bu | ND | 460 | 36 | 30.1 | 593 | 40 |
| 8 | H₃CO-... t-Bu | ND | 85.4 | 43 | 7.22 | 855 | 31 |
| 7 | BnO-... t-Bu | ND | 950 | 56 | 757 | >20k | 0 |

ND = not determined

The in vitro test results of Table 1 show that Compounds of the Invention generally have high binding affinity for μ- and/or κ-opioid receptors, and that these compounds activate these receptors as partial to full agonists. The Compounds of the Invention are therefore expected to be useful to treat Conditions, particularly pain, that are responsive to the activation of μ- and κ-opioid receptors.

Compounds 3, 11, 17, 18, 22, 23, and 32 have also shown δ-opioid receptor activity and compounds 3, 11, 17, 22, 23 and 32 have shown ORL-1 receptor activity in PerkinElmer® ligand binding and cellular assays.

Having now fully described this invention, it will be understood by those of ordinary skill in the art that the same can be performed within a wide and equivalent range of conditions,

What is claimed is:

1. A compound of Formula I:

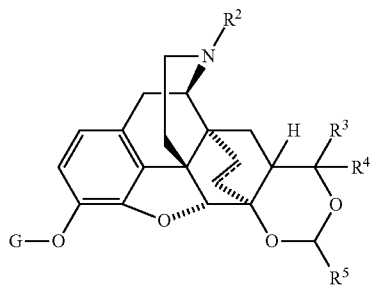

I or a pharmaceutically acceptable salt thereof, wherein:

G is $R^1$ or a hydroxyl protecting group PG;

$R^1$ is hydrogen, $C_{1-6}$ alkyl, $C_{2-4}$ alkenyl, $C_{2-4}$ alkynyl, $C_{3-6}$ cycloalkyl($C_{1-4}$)alkyl, or $C_{6-10}$ aryl ($C_{1-4}$)alkyl, wherein the $C_{3-6}$ cycloalkyl, and $C_{6-10}$ aryl, portions thereof are optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl;

PG is selected from the group consisting of methyl, tert-butyl, benzyl, benzoyl, acetyl, trimethyl silyl, tert-butyldimethyl silyl, tert-butyldiphenyl silyl, and tri-isopropyl silyl;

$R^2$ is (a) hydrogen; or (b) $C_{1-6}$ alkyl, $C_{2-6}$ alkenyl, $C_{2-6}$ alkynyl, $C_{3-7}$ cycloalkyl ($C_{1-4}$)alkyl, $C_{3-7}$ cycloalkenyl($C_{1-4}$)alkyl, or $C_{6-10}$ aryl ($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl;

$R^3$ and $R^4$ are each independently selected from the group consisting of hydrogen, $C_{1-6}$ alkyl, $C_{2-6}$ alkenyl, and $C_{2-6}$ alkynyl, wherein any of which, when other than hydrogen, is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl;

$R^5$ is selected from the group consisting of hydrogen, $C_{1-6}$ alkyl, $C_{2-6}$ alkenyl, $C_{2-6}$ alkynyl, $C_{3-7}$ cycloalkyl, $C_{3-7}$ cycloalkenyl, phenyl, and naphthyl wherein any of which, when other than hydrogen, is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$alkoxycarbonyl; and ⫽ is a single bond or a double bond.

2. The compound of claim 1, having the Formula II:

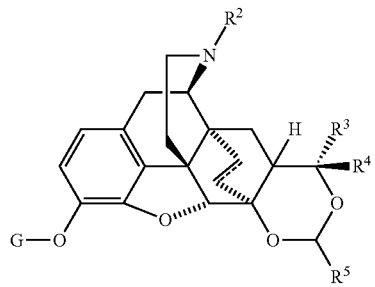

II or a pharmaceutically acceptable salt, prodrug, or solvate thereof, wherein $R^3$ is selected from the group consisting of hydrogen, $C_{1-6}$ alkyl, $C_{2-6}$ alkenyl, and $C_{2-6}$ alkynyl, wherein any of which, when other than hydrogen, is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl;

$R^4$ is selected from the group consisting of hydrogen, $C_{1-6}$ alkyl, $C_{2-6}$ alkenyl, and $C_{2-6}$ alkenyl, wherein any of which, when other than hydrogen, is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl; and G, $R^1$, $R^2$, $R^5$ and ⫽ are as defined in claim 1.

3. The compound of claim 1, having the Formula III:

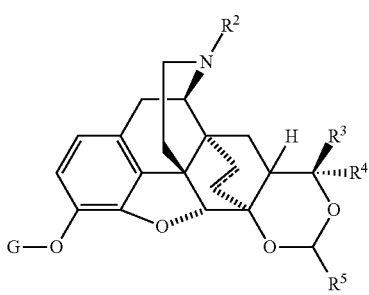

III or a pharmaceutically acceptable salt thereof, wherein $R^3$ is selected from the group consisting of hydrogen, $C_{1-6}$ alkyl, $C_{2-6}$ alkenyl, and $C_{2-6}$ alkynyl, wherein any of which, when other than hydrogen, is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl;

$R^4$ is selected from the group consisting of hydrogen, $C_{1-6}$ alkyl, $C_{2-6}$ alkenyl and $C_{2-6}$ alkenyl, wherein any of which, when other than hydrogen, is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl; and G, $R^1$, $R^2$, $R^5$ and ⫽ are as defined in claim 1.

4. The compound of claim 1, having the Formula IV:

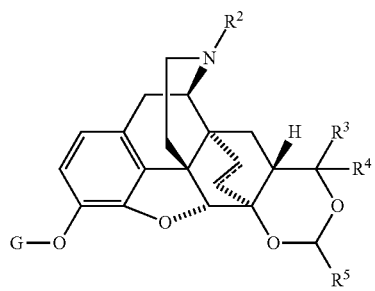

or a pharmaceutically acceptable salt thereof, wherein G, $R^1$-$R^5$ and ⫽ are as defined in claim 1.

5. The compound of claim 2, having the Formula V:

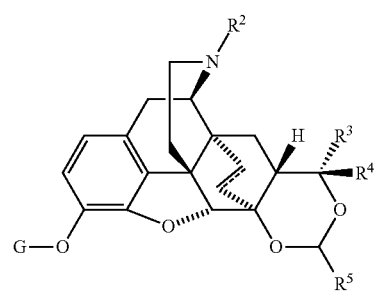

or a pharmaceutically acceptable salt, thereof, wherein G, $R^1$-$R^5$ and ⫽ are as defined in claim 2.

6. The compound of claim 3, having the Formula VI:

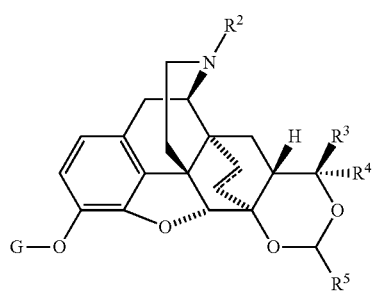

or a pharmaceutically acceptable salt, thereof, wherein G, $R^1$-$R^5$ and ⫽ are as defined in claim 3.

7. The compound of claim 1, having the Formula VII:

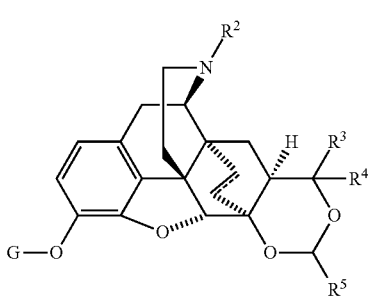

or a pharmaceutically acceptable salt thereof, wherein G, $R^1$-$R^5$ and ⫽ are as defined in claim 1.

8. The compound of claim 2, having the Formula VIII:

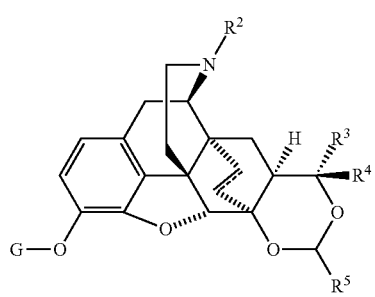

or a pharmaceutically acceptable salt thereof, wherein G, $R^1$-$R^5$ and ⫽ are as defined in claim 2.

9. The compound of claim 3, having the Formula IX:

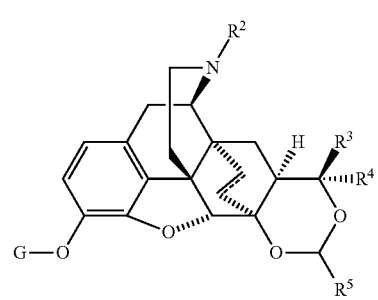

or a pharmaceutically acceptable salt thereof, wherein G, $R^1$-$R^5$ and ⫽ are as define in claim 3.

10. The compound of claim 1, wherein G is $R^1$.

11. The compound of claim 10, wherein $R^1$ is hydrogen.

12. The compound of claim 10, wherein $R^1$ is $C_{1-4}$ alkyl, $C_{2-4}$ alkenyl or $C_{2-4}$ alkynyl.

13. The compound of claim 10, wherein $R^1$ is $C_{3-6}$ cycloalkyl ($C_{1-4}$)alkyl, or $C_{6-10}$ aryl($C_{1-4}$)alkyl, wherein the $C_{3-6}$ cycloalkyl and $C_{6-10}$ aryl portions are optionally substituted with 1,2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl.

14. The compound of claim 1, wherein G is PG.

15. The compound of claim 1, wherein $R^2$ is hydrogen.

16. The compound of claim 1, wherein $R^2$ is $C_{1-6}$ alkyl, $C_{2-6}$ alkenyl, or $C_{3-7}$ cycloalkyl ($C_{1-4}$)alkyl any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl.

17. The compound of claim 16, wherein $R^2$ is $C_{3-7}$ (cycloalkyl)($C_{1-4}$) alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl.

18. The compound of claim 1, wherein ⫽ is a single bond.

19. The compound of claim 1, wherein ⫽ is a double bond.

20. The compound of claim 1, wherein G is $R^1$, $R^3$ is methyl and $R^4$ is tert-butyl having the Formula X:

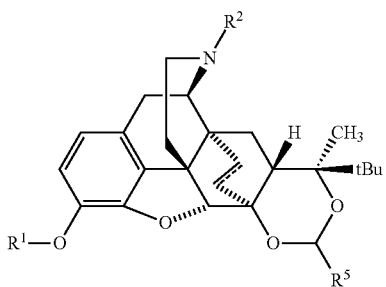

or a pharmaceutically acceptable salt thereof, wherein $R^1$, $R^2$, $R^5$ and ⫽ are as defined in claim 1.

21. The compound of claim 20, having the Formula XI:

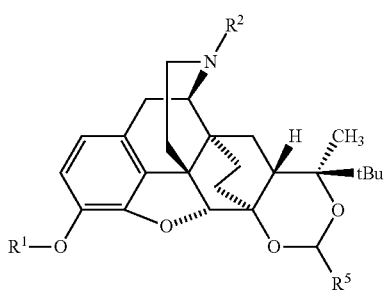

or a pharmaceutically acceptable salt thereof.

22. The compound of claim 20, having the Formula XII:

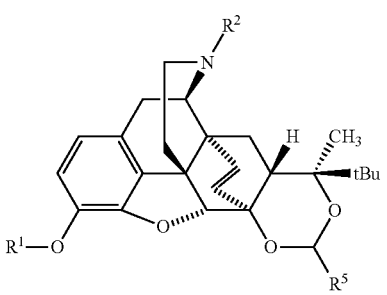

or a pharmaceutically acceptable salt thereof.

23. The compound of claim 20, wherein
$R^1$ is hydrogen, $C_{1-6}$ alkyl, or benzyl;
$R^2$ is $C_{2-6}$ alkenyl, cyclopropyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, and $C_{1-4}$ alkoxycarbonyl; and
$R^5$ is hydrogen, $C_{1-6}$ alkyl, or phenyl.

24. The compound of claim 23, wherein $R^2$ is unsubstituted $C_{2-6}$ alkenyl or unsubstituted cyclopropyl($C_{1-4}$)alkyl.

25. The compound of claim 1, selected from the group consisting of

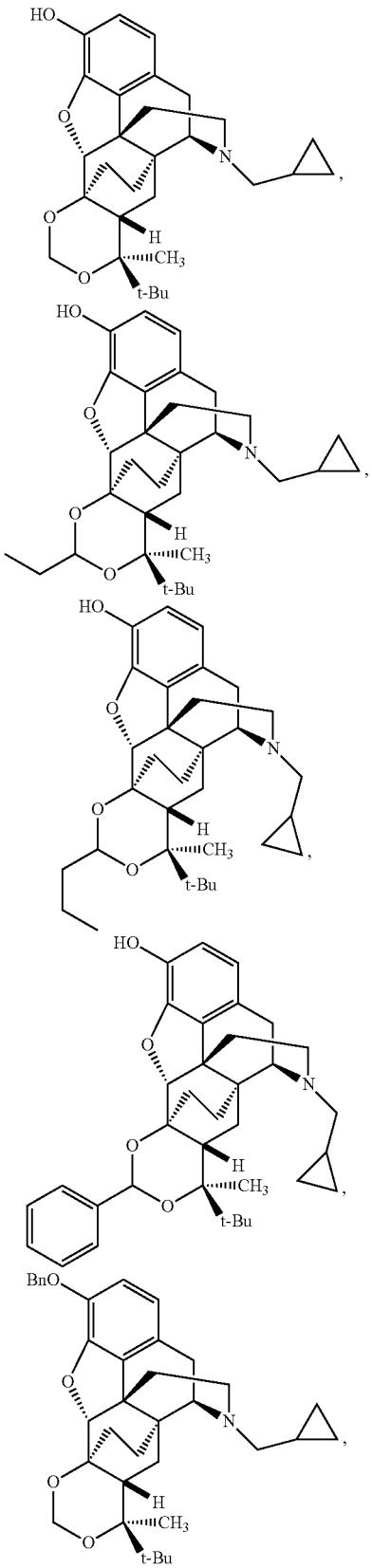

-continued

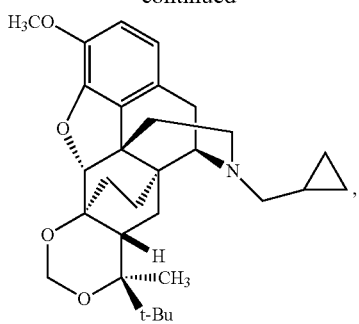

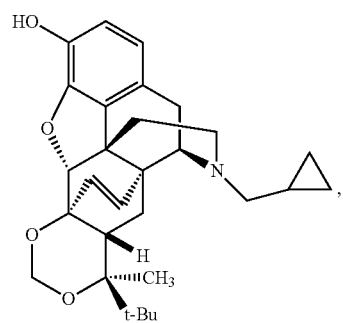

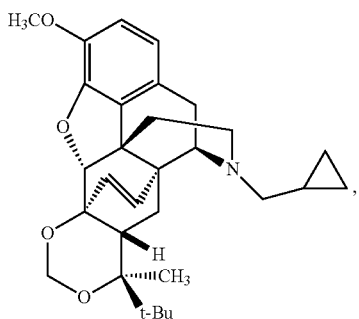

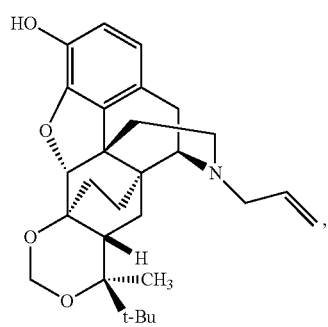

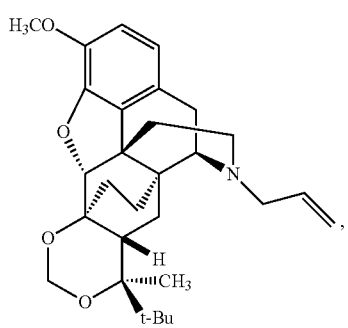

-continued

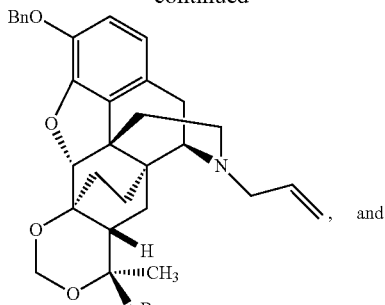
, and

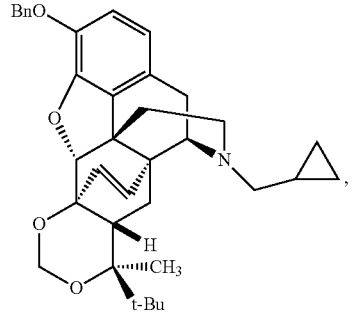
, or a pharmaceutically acceptable salt thereof.

26. A composition, comprising a therapeutically effective amount of the compound of claim 1, or a pharmaceutically acceptable salt thereof, and one or more pharmaceutically acceptable carriers.

27. A method of treating pain in a patient, comprising administering an effective amount of a compound of claim 1, or a pharmaceutically acceptable salt thereof, to the patient in need of such treatment.

28. The method of claim 27, wherein said pain is acute pain, chronic pain or surgical pain.

29. The method of claim 28, wherein said pain is chronic pain.

30. The method of claim 29, wherein said chronic pain is neuropathic pain, postoperative pain, or inflammatory pain.

31. A method of modulating one or more opioid receptors in a patient, comprising administering to the patient an effective amount of at least one compound as claimed in claim 1, or a pharmaceutically acceptable salt thereof.

32. The method of claim 31, wherein the µ- or κ-opioid receptor, or both, are modulated.

33. The compound as claimed in claim 1, or a pharmaceutically acceptable salt, thereof, wherein the compound is $^3$H, $^{11}$C, or $^{14}$C radiolabeled.

34. A method of preparing a pharmaceutical composition, comprising admixing a therapeutically effective amount of a compound of claim 1, or a pharmaceutically acceptable salt thereof, with a pharmaceutically acceptable carrier.

35. A kit, comprising a container containing an effective amount of the compound of claim 1, or a pharmaceutically acceptable salt thereof, and instructions for therapeutic use.

36. A process for preparing a compound of claim 1 having Formula I

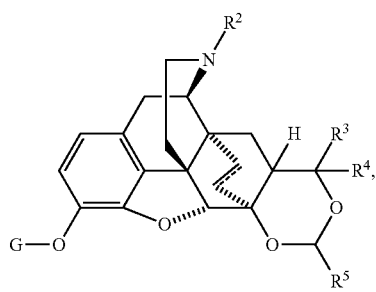

I comprising:
reacting a compound of Formula XIX

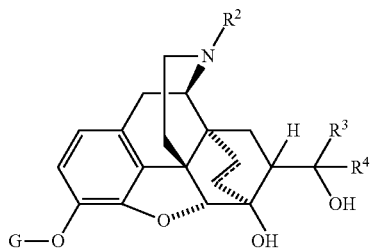

XIX with (R⁵CH₂)₂SO, wherein
R⁵ is as defined in claim 1,
in the presence of a trialkylsilyl halide and an aprotic solvent to give a compound of Formula I.

37. The process of claim 36, wherein said (R⁵CH₂)₂SO is selected from the group consisting of dimethyl sulfoxide, di(n-propyl) sulfoxide, di(n-butyl) sulfoxide, and dibenzyl sulfoxide.

38. The process of claim 36, wherein the trialkylsilyl halide is selected from the group consisting of trimethylsilyl chloride, trimethylsilyl bromide, trimethylsilyl iodide, or a combination thereof.

39. The process of claim 36, wherein the process gives a compound of Formula XV:

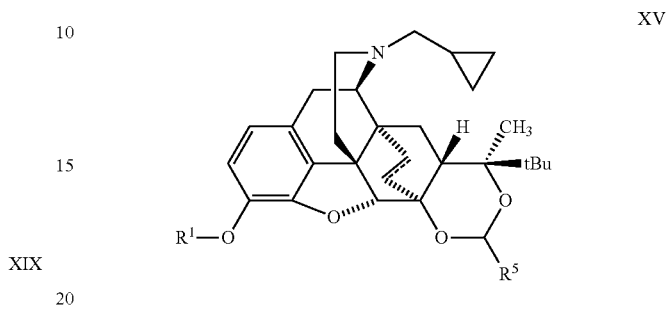

XV wherein $R^1$ is hydrogen, $C_{1-4}$ alkyl, $C_{2-4}$ alkenyl, $C_{2-4}$ alkynl, $C_{3-6}$ cycloalkyl($C_{1-4}$)alkyl, or $C_{6-10}$ aryl($C_{1-4}$) alkyl, wherein the $C_{3-6}$ cycloalkyl, and $C_{6-10}$ aryl, portions thereof are optionally substituted with 1, 2, or 3 substituents, each independently selected from the group consisting of hydroxy, halo, halo ($C_{1-4}$)alkyl, amino, $C_{1-4}$ alkylamino, di($C_{1-4}$)alkylamino, carboxy, and $C_{1-4}$ alkoxycarbonyl; and $R^5$ is as defined in claim 36.

40. The compound of claim 5, wherein $R^5$ is hydrogen, $C_{1-6}$ alkyl, or phenyl.

41. The compound of claim 6, wherein $R^5$ is hydrogen, $C_{1-6}$ alkyl, or phenyl.

* * * * *